(12) United States Patent
Poliakov et al.

(10) Patent No.: US 6,290,950 B1
(45) Date of Patent: Sep. 18, 2001

(54) MYCOSIS VACCINES

(75) Inventors: Igor Dimitrievich Poliakov; Ludmilla Ivanova, both of Ringelhauser Allee 73, D-88471 Laupheim (DE)

(73) Assignees: Igor Dimitrievich Poliakov; Ludmilla Ivanova, both of Laupheim (DE)

( * ) Notice: Subject to any disclaimer, the term of this patent is extended or adjusted under 35 U.S.C. 154(b) by 0 days.

(21) Appl. No.: 09/269,342

(22) PCT Filed: Sep. 22, 1997

(86) PCT No.: PCT/EP97/05181

§ 371 Date: May 5, 1999

§ 102(e) Date: May 5, 1999

(87) PCT Pub. No.: WO98/15284

PCT Pub. Date: Apr. 16, 1998

(30) Foreign Application Priority Data

Oct. 4, 1996 (EP) ................................................. 96115954

(51) Int. Cl.⁷ .................................................. A01N 63/00
(52) U.S. Cl. .................. 424/93.5; 424/93.51; 424/274.1; 435/7.31; 435/254.1; 435/254.2; 435/254.22; 435/255.1; 435/255.7
(58) Field of Search ............................. 424/274.1, 184.1, 424/93.5, 93.51; 435/254.1, 69.1, 69.3, 7.31, 254.2, 254.22, 255.1, 255.7

(56) References Cited

U.S. PATENT DOCUMENTS 5,277,904   1/1994   Pier ........................................ 424/88

FOREIGN PATENT DOCUMENTS 0 393 371   10/1990   (EP) .
WO 93/07894   4/1993   (WO) .
WO 96/07426   3/1996   (WO) .

OTHER PUBLICATIONS

Stoughton R.B. Chapter 208: Dermatophytosis In: Medical Microbiology and Infectious Diseases Ed: Braude et al. 1981, pp. 1568–1573.*
Hernando, Fernando L. et al, Mycopathologia, 134 91), pp 1–6, Apr. (See Abstract), 1996.*
The Merck Index, 11th edition, Susan Budavari, Merck & Co., Inc, p4722 and P 7636, 1989.*
Baldry MG, J. Applied Bacteriology, Jun., 54(3): pp417–23 (See Abstract), 1983.*
Wharton, M.L. et al., "Active Immunization Against Trichophyton Purpureum Infection in Rabbits," *J. Invest. Derm.* 14:291:303 (Apr. 1950).
English language abstract of WO 93/07894 (Document AM1), Derwent World Patents Index, WPI Accession No. 93–152184/199318.
International Search Report for International Application No. PCT/EP97/05181, mailed Apr. 22, 1998.

* cited by examiner

*Primary Examiner*—Jeffrey Stucker
*Assistant Examiner*—Ulrike Winkler
(74) *Attorney, Agent, or Firm*—Norris McLaughlin & Marcus

(57) ABSTRACT

The present invention pertains to vaccines comprising homogenised inactivated yeast blastospores and homogenised inactivated dermatophyte microconidia or antigenic material of said spores, methods for their production and their use for the prophylaxis and/or treatment of mycoses in mammals, preferably humans. The vaccines according to the present invention are especially useful for the prophylaxis and/or treatment of skin mycosis, preferably Dermatomycosis and/or Candidosis and/or Onychomycosis.

32 Claims, 10 Drawing Sheets

MYCOSIS VACCINES

The present invention is in the field of mycology and pertains to vaccines comprising homogenised inactivated dermatophyte microconidia and inactivated homogenised yeast blastospores or antigenic material of said spores, methods for their production and their use for the prophylaxis and/or treatment of mycoses in mammals, preferably humans. The vaccines according to the present invention are especially useful for the prophylaxis and/or treatment of skin mycoses, preferably Dermatomycosis and/or Candidosis and/or Onychomycosis.

Recently, the percentage of fungal infections (mycoses) has increased dramatically. Specifically, the percentage of fungal infections of the skin (skin mycoses) has increased to 4–8% of all skin diseases in humans. This percentage is increased up to 15–20% under tropical conditions. The most common pathogens associated with skin mycoses are dermatophytes of the genus Trichophyton, like *Trichophyton rubrum, Trichophyton mentagrophytes* and/or *Trichophyton verrucosum*. Other fungal pathogens associated with skin mycoses are yeasts, for example the genus Candida, i.e. *Candida albicans*.

A typical example for skin mycosis is Onychomycosis, i.e. *Tinea unguium*. Onychomycosis afflicts about 2–8% of the human population. Major pathogens associated with Onychomycosis in European countries are dermatophytes of the species *Trichophyton rubrum* and *Trichophyton mentagrophytes* as well as yeasts of the species *Candida albicans*. *Candida albicans* is found much more frequently in infected finger nails than toe nails. Unlike other skin mycoses, Onychomycoses never heal spontaneously and always lead in the terminal state to Onychodystrophy, if left untreated.

Skin mycoses are normally treated using a topical therapy with antimycotic chemical substances. However, these chemical substances have considerable side effects (e.g. hepatotoxicity, potential teratogenicity, gastrointestinal and central nervous system irritations as well as allergic reactions) and/or reach the target site only insufficiently, like in case of Onychomycosis, where the infected site is covered by the nail. Especially in chronic infections, where hair roots or nails are infected, these chemical therapies are lengthy and frustrating, for both the physician and the patient. Further, the rate of recurrence of infection is extremely high.

Skin mycoses can develop into systemic fungal infections (systemic mycosis), i.e. in immune compromised individuals. Systemic infections usually need to be treated with chemical agents for weeks or months. Treatment sometimes can last up to one year. Compliance of the patients often suffers when side-effects appear, and the benefit-risk-relation has become a special issue.

According to current knowledge, chronic fungal infections occur in otherwise healthy individuals, i.e. non immune deficient individuals, because in these individuals only an antibody response is triggered against the fungus, i.e. IgE mediated immunological response, but no cell-mediated immune response. However, the antibody-mediated immunological response alone is not sufficient to fight the fungus infection successfully. Chronic mycosis is the result (Sorensen, G. W., Arch. Dermatol. 112, 1976, 4042; Hay, R. J., Shennan, G., Br. J. Dermatol. 106, 1982, 191–198; Dahl, M. V., Adv. Dermatol. 2, 1987, 305–320).

Vaccines comprising live dermatophytes are well known for their ability to elicit both responses, however, as with all live vaccine preparations, infection of healthy individuals by freshly vaccinated individuals is a permanent risk. Inactivated vaccines often fail to elicit a sufficient cell mediated response and accordingly are not as efficient as live vaccines.

Approaches concerning the use of inactivated dermatophytes as Dermatomycosis vaccines are known from prior art. For example Wharton, M. et al. (1950, J. Invest. Derm. 14, 291–303) teach active immunisation against *Trichophyton purpureum* infection in rabbits with an inactivated suspension of *Trichophyton rubrum* hyphae. EP 393371 and WO 9307894 teach inactivated Dermatomycosis vaccines comprising dermatophytes of the genus Trichophyton and/or Microsporum. To our knowledge, no mycoses vaccines are known from prior art, that comprise homogenised inactivated dermatophyte microconidia and inactivated homogenised yeast blastospores.

It was now surprisingly found, that vaccines comprising homogenised inactivated dermatophyte microconidia and inactivated homogenised yeast blastospores confer good resistance against fungal infections.

The present invention now provides vaccines comprising homogenised inactivated dermatophyte microconidia and inactivated homogenised yeast blastospores or antigenic material of said spores, methods for their production and their use for the prophylaxis and/or treatment of mycosis in mammals, preferably humans. The vaccines according to the present invention are especially useful for the prophylaxis and/or treatment of skin mycoses, preferably Dermatomycosis and/or Candidosis and/or Onychomycosis.

The vaccines of the present invention have excellent immunogenic-properties in the absence of adverse side effects. In particular, the vaccines of the present invention do not provoke allergic reactions.

In one embodiment, the vaccines of the present invention comprise inactivated yeast blastospores and/or yeast blastospores that are in a swollen condition and/or have germ tubes and/or dermatophyte microconidia and/or dermatophyte microconidia that are in a swollen condition and/or have germ tubes, or antigenic material of said spores. Preferably, the yeast blastospores belong to the genus Candida, more preferably the species *Candida albicans* and/or the dermatophyte microconidia belong to the genus Trichophyton and/or Microsporum, i.e. the species *Trichophyton rubrum* and/or *Trichophyton mentagrophytes* and/or *Microsporum canis*. Highly preferred are the strains *Candida albicans* DSM-9456, and/or *Candida albicans* DSM-9457 and/or *Candida albicans* DSM-9458 and/or *Candida albicans* DSM-9459 and/or *Trichophyton rubrum* DSM-9469 and/or *Trichophyton rubrum* DSM-9470 and/or *Trichophyton rubrum* DSM-9471 and/or *Trichophyton rubrum* DSM-9472 and/or *Trichophyton mentagrophytes* DSM-7279 and/or *Microsporum canis* DSM-7281. Highly preferred are combinations of strains according to the examples. Preferably, 50% of the yeast blastospores and/or the dermatophyte microconidia are in swollen condition and/or have germ tubes. Preferably, the concentration of the spores is 40 to 90 million per ml, highly preferred is a concentration of about 60 million spores per ml. For inactivation of the spores, preferably thiomersal, formaldehyde or 2-propiolactone are used.

In another embodiment of the present invention, the yeast blastospores and/or dermatophyte microconidia are modified by chemical treatment, preferably by treatment with $H_2O_2$ and/or sodium permanganate and/or potassium permanganate.

The vaccines of the present invention can modulate the immune system, i.e. they have immunostimulatory properties and can be administered in the absence of additional immunostimmulatory substances. Therefore, in one embodiment, the vaccines of the present invention do not comprise adjuvants or other immunomodulatory or immunostimulatory substances.

To further increase their immunogenic properties, in another embodiment, the vaccines of the present invention further comprise at least one substance with immunomodulatory activity, preferably an adjuvant, preferably selected from the group of vitamin-E acetate, o/w-emulsion, aluminium phosphate, aluminium oxide, aluminium hydroxide/methyl cellulose gel, an oil-emulsion, muramil-dipeptides, Freund's adjuvants and saponins and/or at least one cytokine, preferably selected from the group of IL 2, IL 12, INF-Gamma.

In one embodiment, the vaccines of the present invention are used for the treatment and/or prophylaxis of mycoses, preferably skin mycosis, preferably Dermatomycosis and/or Candidosis and/or Onychomycosis in mammals, preferably humans.

In another embodiment, the vaccines of the present invention are used as immunomodulators, preferably immunostimulators.

In another embodiment, the vaccines of the present invention are used for stimulating the immune response in an immunocompromised animal.

The vaccines of the present invention can be administered parenterally, preferably by intramuscular injection and/or intraperitoneal injection and/or intracutaneous injection and/or percutaneous injection and/or topically, preferably cutaneously.

In another embodiment, the present invention provides processes for the preparation of the vaccines of the present invention. Said vaccines are preparable from dermatophytes and yeasts, preferably elected from the genera and/or species and/or strains indicated above, according to the following methods:

The first cultivation step for all of the below described processes is carried out according to the following:

Dermatophyte cultures, preferably of the genus Trichophyton and/or Microsporum, more preferably of the species *Trichophyton mentagrophytes* and/or *Trichophyton rubrum* or the strains *Trichophyton rubrum* DSM-9469 and/or *Trichophyton rubrum* DSM-9470 and/or *Trichophyton rubrum* DSM-9471 and/or *Trichophyton rubrum* DSM-9472 and/or *Trichophyton mentagrophyes* DSM-7279 and/or *Microsporum canis* DSM-7281, are cultivated separately on agar/wort, for example in 3–10 Roux flasks. Each culture is cultivated for 15–30 days at 26–28° C.

Yeast cultures, preferably of the genus Candida, more preferably of the species *Candida albicans* or the strains *Candida albicans* DSM-9456, and/or *Candida albicans* DSM-9457 and/or *Candida albicans* DSM-9458 and/or *Candida albicans* DSM-9459, are cultivated separately in, for example 2–8 Roux flasks on agar Sabouraud or malt extract agar or other suitable media at 26–37° C. for 1–7 days.

Fungal material obtainable according to this process is then preferably processed according to the following:

Method 1 (Exemplified in Examples 1–7)

The fungal masses of the dermatophytes are lifted off and separately homogenised in an aqueous solution (for example 100–500 ml) of 0.1–0.3% fermented hydrolyzed muscle protein or 0.1–1% soy or pork peptone in combination with 5–6% glucose and 0.1–1% yeast extract. The concentration of microconidia is adjusted to 30–90 million per ml for each homogenate. Then each suspension of microconidia is fermented for 1–2 days at 28° C., to yield 50 to 100% germ tubes. After fermentation the cell suspensions can be washed with distilled water, physiological salt solution, for example sodium chloride or another suitable solution.

The blastospores of *Candida albicans* are washed off with a physiological solution of sodium chloride or another suitable solution. The concentration of blastospores in suspension is adjusted to 10–90 million per ml.

Equal volumes of each culture in suspension are mixed in a single container. The homogenate is inactivated by adding thiomersal in a ratio of 1:11000 to 1:25000 (w/v) directly to the cell suspension. The mixture is incubated for 1–3 days at room temperature.

The resulting vaccine is bottled, checked for sterility, safety and immunogenic properties in accordance with accepted methods and can be stored refrigerated at 4–10° C. Vaccines preparable according to this method can be used for the prophylaxis and treatment of mycoses in mammals, preferably humans.

Method 2 (Exemplified in Examples 8–11)

The fungal masses of the dermatophytes are lifted off and separately homogenised in an aqueous solution (for example 100–500 ml) of 0.1–0.3% fermented hydrolyzed muscle protein, 5–6% glucose and 0.1–1% yeast extract. The concentration of microconidia is adjusted to 30–90 million per ml for each homogenate. To yield 50 to 100% germ tubes, each suspension of microconidia is fermented for 1–2 days at 28° C. Equal volumes of each dermatophyte culture in suspension are mixed in a single container. The homogenate is inactivated by adding thiomersal in a ratio of 1:10000 to 1:25000 (w/v) directly to the cell suspension. The mixture is incubated at room temperature for 1–2 days.

Each yeast culture is harvested and homogenised in 5000 ml medium RPMI No. 1640 comprising L-glutamine (Serva), medium No. 199 (Serva) or other suitable cell culture media. The concentration of the blastospores is adjusted to 10–30 million per ml. The fungi cell suspensions are incubated in cell culture flasks containing one of the above mentioned media in a $CO_2$ atmosphere of 5–6% at 36–38° C. After 24 hours incubation 50–100% of the blastospores commonly display germ tubes and a swollen condition. The blastospores are harvested and washed 3–5 times, for example by centrifugation (4000–6000 rpm) for 25–45 minutes for[]each centrifugation step at 4–10° C.

Then the concentration of the cells is adjusted to 10–90 million per ml. The homogenate is inactivated by adding thiomersal in a ratio of 1:10000 to 1:25000 (w/v) directly to the cell suspension. The mixture is incubated at room temperature for 2 days. Equal volumes of each *Candida albicans* culture in suspension are mixed in a single container.

The dermatophyte and yeast cell suspensions are then mixed. The resulting vaccine is bottled, checked for sterility, safety and immunogenic properties in accordance with accepted methods and kept refrigerated at 4–10° C. Vaccines preparable according to this method can be used for the prophylaxis and treatment of mycoses in mammals, preferably humans.

Method 3 (Exemplified in Examples 12–15)

The fungal masses of the dermatophytes are lifted off and separately homogenised in an aqueous solution (for example 100–500 ml) of 0.1–0.3% fermented hydrolyzed muscle protein, 5–6% glucose and 0.1–1% yeast extract. The concentration of microconidia is adjusted to 30–90 million per ml for each homogenate. To yield 50–100% germ tubes, each suspension of microconidia is fermented for 1–2 days at 28° C.

The yeast blastospores are lifted off by washing with a physiological solution of sodium chloride or another suitable solution. The concentration of blastospores in suspension is adjusted to 10–90 million per ml.

Equal volumes of each culture in suspension are mixed in a single container. The homogenate is inactivated by adding thiomersal in a ratio of 1:11000 to 1:25000 (w/v) directly to the cell suspension. The mixture is then incubated at room temperature for 1–3 days.

Following the inactivation the cell suspension is treated with $H_2O_2$. For this purpose substances containing $H_2O_2$ are added to yield a final concentration of 1–3% of $H_2O_2$. The cell suspension is mixed for 14–48 hours. Treated cells are washed 3–5 times by centrifugation (4000 to 6000 rpm) for 20–50 minutes with destined water or a physiological solution of sodium chloride. The final suspension of spores is adjusted to 30–90 million per ml. Alternatively to $H_2O_2$ treatment, the cell suspensions can be treated with sodium or potassium permanganate. For this purpose a concentration of 1:10000 to 1:30000 (w/v) of sodium or potassium permanganate is added and the suspension is mixed for 10–48 hours. Treated cells are washed 3–5 times, for example with destined water by centrifugation for 2545 minutes for each centrifugation step (4000 rpm–6000 rpm). The final concentration of the spores is adjusted to 30–90 million per ml.

The dermatophyte and yeast cell suspensions are then mixed. The resulting vaccine is bottled, checked for sterility, safety and immunogenic properties in accordance with accepted methods and kept refrigerated at 4–10° C. Vaccines preparable according to this method can be used for the prophylaxis and treatment of mycoses in mammals, preferably humans.

Method 4 (Exemplified in Examples 16–19)

The fungal masses of the dermatophytes are lifted off and separately homogenised in an aqueous solution (for example 100–500 ml) of 0.1–0.3% fermented hydrolyzed muscle protein, 5–6% glucose and 0.1–1% yeast extract. The concentration of microconidia is adjusted to 30–90 million per ml for each homogenate. To yield 50–100% germ tubes each suspension of microconidia is fermented for 1–2 days at 28° C. Equal volumes of each dermatophyte culture in suspension are mixed in a single container. The homogenate is inactivated by adding thiomersal in a ratio of 1:10000 to 1:25000 (w/v) directly to the cell suspension. This mixture is incubated at room temperature for 1–2 days.

Following the inactivation, the cell suspension is treated with $H_2O_2$. For this purpose substances containing $H_2O_2$ are added to yield a final concentration of 1–3% of $H_2O_2$. The cell suspension is mixed for 14–48 hours. Treated cells are washed 3–5 times by centrifugation (4000 to 6000 rpm) for 20–50 minutes with destined water or a physiological solution of sodium chloride. The final concentration of spores is adjusted to 30–90 million per ml.

Alternatively to $H_2O_2$ treatment, the cell suspensions can be treated with sodium or potassium permanganate. For this purpose a concentration of 1:10000 to 1:30000 (w/v) of sodium or potassium permanganate is added and the suspension is mixed for 10–48 hours. Treated cells are washed 3–5 times, for example with destined water by centrifugation for 25–45 minutes for each centrifugation step (4000 rpm–6000 rpm). The final concentration of the spores is adjusted to 30–90 million per ml.

Each yeast culture is harvested and homogenised in 5000 ml medium RPMI No.1640 comprising L-glutamine (Serva), medium No. 199 (Serva) or other types of medium for cell cultures. The concentration of the blastospores is adjusted to 10–30 million per ml. The fungi cell suspensions are incubated in cell culture flasks containing one of the above mentioned media in a $CO_2$ atmosphere of 5–6% at 36–38° C. After 24 hours incubation 50–100% of the blastospores commonly display germ tubes and a swollen condition. The blastospores are harvested and washed for 3–5 times by centrifugation (4000–6000 rpm) for 25–45 minutes at 4–10° C. The concentration of the spores is adjusted to 10–90 million per ml. The homogenate is inactivated by adding thiomersal in a ratio of 1:10000 to 1:25000 (w/v) directly to the cell suspension. The mixture is incubated at room temperature for 2 days.

Following the inactivation the cell suspension is treated with $H_2O_2$. For this is purpose substances containing $H_2O_2$ are added to yield a final concentration of 1–3% of $H_2O_2$. Then the cell suspension is mixed for 1448 hours. Treated cells are washed 3–5 times by centrifugation (4000–6000 rpm) for 20–50 minutes with destined water or a physiological solution of sodium chloride. The final concentration of spores is adjusted to 30–90 million per ml.

Alternatively to $H_2O_2$ treatment, the cell suspensions can be treated with sodium or potassium permanganate. For this purpose a concentration of 1:10000 to 1:30000 (w/v) of sodium or potassium permanganate is added and the suspension is mixed for 10–48 hours. Treated cells are washed 3–5 times by centrifugation (4000–6000 rpm) for 25–45 minutes with destined water. The final concentration of spores is adjusted to 30–90 million per ml. Then equal volumes of each yeast culture in suspension are mixed in a single container. The dermatophyte and yeast cell suspensions are then mixed. The resulting vaccine is bottled, checked for sterility, safety and immunogenic properties in accordance with accepted methods and kept refrigerated at 4–10° C. Vaccines preparable according to this method can be used for the prophylaxis and treatment of mycoses in mammals, preferably humans.

Method 5 (Exemplified in Examples 20–23)

The fungal masses of the dermatophytes are lifted off and separately homogenised in an aqueous solution (for example 100–500 ml) of 0.1–0.3% fermented hydrolyzed muscle protein, 5–6% glucose and 0.1–1% yeast extract. The concentration of microconidia is adjusted to 30–90 million per ml for each homogenate.

The yeast blastospores are lifted off by washing with a physiological solution of sodium chloride or another suitable solution. The concentration of blastospores in suspension is adjusted to 10–90 million per ml.

Equal volumes of each culture in suspension are combined and mixed in a single container. The homogenate is inactivated by adding thiomersal in a ratio of 1:11000 to 1:25000 (w/v) directly to the cell suspension. The mixture is incubated at room temperature for 1–3 days.

The resulting vaccine is bottled, checked for sterility, safety and immunogenic properties in accordance with accepted methods and kept refrigerated at 4–10° C. Vaccines preparable according to this method can be used for the prophylaxis and treatment of mycoses in mammals, preferably humans.

Method 6 (Exemplified in examples 24–27)

The fungal masses of the dermatophytes are lifted off and separately homogenised in an aqueous solution (for example 100–500 ml) of 0.1–0.3% fermented hydrolyzed muscle protein, 5–6% glucose and 0.1–1% yeast extract. The concentration of microconidia is adjusted to 30–90 million per ml for each homogenate.

The yeast blastospores are lifted off by washing with a physiological solution of sodium chloride or another suitable solution. The concentration of blastospores in suspension is adjusted to 10–90 million per ml.

Equal volumes of each culture in suspension are combined and mixed in a single container. The homogenate is inactivated by adding thiomersal in a ratio of 1:11000 to 1:25000 (w/v) directly to the cell suspension. The mixture is then incubated at room temperature for 1–3 days.

Following the inactivation, the cell suspension is treated with $H_2O_2$. For this purpose substances containing $H_2O_2$ are added to yield a final concentration of 1–3% of $H_2O_2$. Then the cell suspension is mixed for 1448 hours. Treated cells are washed 3–5 times by centrifugation (4000–6000 rpm) for 20–50 minutes for each centrifugation step with destined water or a physiological solution of sodium chloride. The final concentration of cells is adjusted to 30–90 million per ml.

Alternatively to $H_2O_2$ treatment, the cell suspensions can be treated with sodium or potassium permanganate. For this purpose a concentration of 1:10000 to 1:30000 (w/v) of sodium or potassium permanganate is added and the suspension is mixed for 10–48 hours. Treated cells are washed 3–5 times, for example with destined water by centrifugation for 25–45 minutes for each centrifugation step (4000–6000 rpm). The final concentration of the spores is adjusted to 30–90 million per ml.

The dermatophyte and yeast cell suspensions are then mixed. The resulting vaccine is bottled, checked for sterility, safety and immunogenic properties in accordance with accepted methods and kept refrigerated at 4–10° C. Vaccines preparable according to this method can be used for the prophylaxis and treatment of mycosis in mammals, preferably humans.

The vaccines preparable according to methods 1 to 6, can be combined with a carrier, comprising a substance with immunomodulatory activity, preferably an adjuvant, preferably selected from the group of vitamin-E acetate, o/w-emulsion, aluminium phosphate, aluminium oxide, aluminium hydroxide/methyl cellulose gel, an oil-emulsion, muramil-dipeptides, Freund's adjuvants and saponins and/or at least one cytokine, preferably selected from the group of IL 2, IL 12, INF-Gamma, to further increase the immunogenic activity of the vaccines of the present invention.

1. Process for the Preparation of an Increased Number of Swollen Microconidia and Microconidia with Germ Tubes of Dermatophytes Dermatophyte cultures are grown for 15–20 days in Roux flasks on solid agar surfaces (malt extract-agar, agar Sabouraud). The cultures are lifted off and homogenised with a sterile liquid medium of, for example, 0.3–1.0% crude extract or peptone from meat or soya, containing 5–6% glucose and 0.1–1.0% yeast extract or malt-extract broth or meat-glucose broth or others. The pH of the medium is maintained at 6.2–7.2. The concentration of microconidia in the fungal suspension is adjusted to 30–90 million per ml. For the second cultivation step (deep cultivation) the spore suspension is placed in a separate vessel containing the medium mentioned above. The deep cultivation is accomplished in 10–48 hours. 10–15 hours after beginning the cultivation, microscopical controls of the cell suspensions are made in order to count the number of swollen and germinated cells. Such controls are repeated every 5–6 hours. The cultivation is stopped when no less than 50% of the microconidia display a swollen or germinating condition and no more than 7–10% of the cells display a second mycelial branch. The diameter of swollen and germinated microconidia increases by 1.2 or more compared to regular microconidia.

2. Process for the Preparation of an Increased Number of Swollen Blastospores and Blastospores with germ Tubes of Yeast Yeast cultures, preferably of Candida species are cultivated for 2–3 days on solid agar surfaces (malt extract-agar, agar Sabouraud). The cultures are lifted off and homogenised with a sterile liquid medium, preferably, medium No. 1640 (Serva) or medium No. 199 (Serva) or 0.3–1.0% meat extract comprising 5–6% glucose and 0.1–1.0% yeast extract adjusted to pH 6.8–7.0. The concentration of blastospores of the fungal suspension is adjusted to 1–20 million per ml. The resulting spore suspension is then placed in cell culture flasks or Petri dishes (2–5 mm height of liquid layer) and incubated in a $CO_2$ atmosphere of 5–6% at 36–38° C. for 24 hours. The incubation process is stopped when 50% or more of the cells display germ tubes or a swollen condition. Swollen and germinated blastospores preparable according to this process have an increased diameter of 1.2 or more compared to regular blastospores.

In another embodiment the present invention provides highly immunogenic fungus strains as described below. These strains are especially suitable for the production of the highly immunogenic vaccines according to the present invention. All strains have been deposited by the applicant according to the Budapest Treaty at the 'Deutsche Sammlung von Mikroorganismen und Zellkulturen' (DSM), Mascheroder Weg IB, W-38124 Braunschweig, Germany.

*TRICHOPHYTON RUBRUM*, No. DSM-9469

The strain was deposited at the DSM on Oct. 26, 1994 under Ser. No. DSM-9469.

The strain was obtained by directed selection based on spore production and attenuation of the epizootic strain No. 533, which was identified on a skin of man in 1985. The strain was identified using the "Rebell-Taplin" key (Rebell, G., Taplin, D.: Dermatophytes, their recognition and identification, 3rd Print, University of Miami Press. Coral Gables, Fla., USA, 1978).

The biological properties of the strain are described in Table A.

Strain No. DSM-9469 differs from the epidemic strain in its faster growth in nutrient medium, an enormous production of microconidiae and lower virulence.

*TRICHOPHYTON RUBRUM*, No. DSM-9470

The strain was deposited at the DSM on Oct. 26, 1994 under Serial No. DSM-9470.

The strain was obtained by directed selection based on spore production and attenuation of the epizootic strain No. 535, which was identified on a skin of man in 1990. The strain was identified using the "Rebell-Taplin" key (Rebell, G., Taplin, D.: Dermatophytes, their recognition and identification, 3rd Print, University of Miami Press. Coral Gables, Fla., USA, 1978).

The biological properties of the strain are described in Table B. Strain No. DSM-9470 differs from the epidemic strain in its faster growth in nutrient medium, an enormous production of microconidiae and lower virulence.

*TRICHOPHYTON RUBRUM*, No. DSM-9471

The strain was deposited at the DSM on Oct. 26, 1994 under Ser. No. DSM-9471.

The strain was obtained by directed selection based on spore production and attenuation of the epizootic strain No. 620, which was identified on a nail of man in 1989. The strain was identified using the "Rebell-Taplin" key (Rebell, G., Taplin, D.: Dermatophytes, their recognition and identification, 3rd Print, University of Miami Press. Coral Gables, Fla., USA, 1978).

The biological properties of the strain are described in Table C. Strain No. DSM-9471 differs from the epidemic strain in its faster growth in nutrient medium, an enormous production of microconidiae and lower virulence.

TRICHOPHYTON RUBRUM, No. DSM-9472

The strain was deposited at the DSM on Oct. 26, 1994 under Serial No. DSM-9472.

The strain was obtained by directed selection based on spore production and attenuation of the epizootic strain No. 754, which was identified on a nail of man in 1990. The strain was identified using the "Rebell-Taplin" key (Rebell, G., Taplin, D.: Dermatophytes, their recognition and identification, 3rd Print, University of Miami Press. Coral Gables, Fla., USA, 1978).

The biological properties of the strain are described in Table D.

Strain No. DSM-9472 differs from the epidemic strain in its faster growth in nutrient medium, an enormous production of microconidiae and lower virulence.

CANDIDA ALBICANS, No. DSM-9456

The strain was deposited at the DSM on Oct. 26, 1994 under Serial No. DSM-9456.

The strain was obtained by directed selection based on stabilisation of cultural-morphological characteristics and attenuation of epidemic strain No. 008-L, which was identified on man in 1990. The strain was identified using the Lodder's key (Lodder,J: The yeast: A Taxonomic Study. North-Holland Publ. Co., Amsterdam-London (1970).

The biological properties of the strain are described in Table E.

Strain No. DSM-9456 differs from the epidemic strain in its faster growth in nutrient medium, stabile biological properties, an enormous production of biomass and lower virulence.

CANDIDA ALBICANS. No. DSM-9457

The strain was deposited at the DSM on Oct. 26, 1994 under Serial No. DSM-9457.

The strain was obtained by directed selection based on stabilisation of cultural-morphological characteristics and attenuation of epidemic strain No. 012, which was identified on man in 1992. The strain was identified using the Lodder's key (Lodder,J: The yeast: A Taxonomic Study. North-Holland Publ. Co., Amsterdam-London (1970).

The biological properties of the strain are described in Table F.

Strain No. DSM-9457 differs from the epidemic strain in its faster growth in nutrient medium, stabile biological properties, an enormous production of biomass and lower virulence.

CANDIDA ALBICANS. No. DSM-9458

The strain was deposited at the DSM on Oct. 26, 1994 under Serial No. DSM-9458.

The strain was obtained by directed selection based on stabilisation of cultural-morphological characteristics and attenuation of epidemic strain No. 047, which was identified on man in 1989. The strain was identified using the Lodder's key (Lodder,J: The yeast: A Taxonomic Study. North-Holland Publ. Co., Amsterdam-London (1970).

The biological properties of the strain are described in Table G.

Strain No. DSM-9458 differs from the epidemic strain in its faster growth in nutrient medium, stabile biological properties, an enormous production of biomass and lower virulence.

CANDIDA ALBICANS, No. DSM-9459

The strain was deposited at the DSM on Oct. 26, 1994 under Serial No. DSM-9459.

The strain was obtained by directed selection based on stabilisation of cultural-morphological characteristics and attenuation of epidemic strain No. 158, which was identified on man in 1990. The strain was identified using the Lodder's key (Lodder,J: The yeast: A Taxonomic Study. North-Holland Publ. Co., Amsterdam-London (1970).

The biological properties of the strain are described in Table H.

Strain No. DSM-9459 differs from the epidemic strain in its faster growth in nutrient medium, stabile biological properties, an enormous production of biomass and lower virulence.

Strains Trichophyton mentagrophytes DSM-7279 and Microsporum canis DSM-7281 have been deposited at the DSM by the applicant on Oct. 1, 1992 under the Budapest Treaty and are described for example in applicant's Patent Application No. PCT/EP92/02391, published as WO 93/07894 on Apr. 29, 1993.

Strains Deposited by Basotherm GmbH, 88396 Biberach an der Riss, Germany

The strains:

Trichophyton rubrum, strain No. 533 (DSM No. 9469),
Trichophyton rubrum, strain No. 535 (DSM No. 9470),
Trichophyton rubrum, strain No. 620 (DSM No. 9471)
Trichophyton rubrum, strain No. 754 (DSM No. 9472)
Candia albicans, strain No. 008-L (DSM No. 9456)
Candia albicans, strain No. 012 (DSM No. 9457)
Candia albicans, strain No. 047 (DSM No. 9458)
Candia albicans, strain No. 158 (DSM No. 9459)

have been deposited by the Basotherm GmbH, Germany. The depositor has authorized the applicant to refer to the deposited biological material in the application and has given his unreserved and irrevocable consent to the deposited material being made available to the public in accordance with Rule 28 EPC.

TABLE A

| Properties and characteristics of the strains | Strain No. DSM-9469 | Epidemic Strain No. 533 |
|---|---|---|
| Description of the culture | Mature 15-day colony on agar Sabouraud: white, velvety, flat margin of colony fringed, under surface yellow, in centre deep purple, diameter of colony 60–63 mm | 20-day colony on agar Sabouraud: white, downy, elevated, margin of colony regular, under surface purple, diameter of colony 30–35 mm |
| Morphological characteristics | Mature 15-day culture with septate branching hyphae 1–3 $\mu$m wide, numerous obovate oval microconidia measuring 2–3 × 3–5 $\mu$m, macroconidia long clavate pencil-shaped with 4–5 cross walls measuring 4–6 × 15–40 $\mu$m. | 20-day culture with septate branching hyphae 1–3 $\mu$m wide, microconidia clavate to round in small open clusters and along the hyphae measuring 2–3 × 3–6 $\mu$m; macroconidia are rare, long and pencil-shaped with 3–5 cross walls measuring 4–7 × 15–50 $\mu$m. |
| Pathogenic characteristics | The strain is weakly virulent. 9–10 days after application of a dose of 500–600 thousand cells of fungal material per $cm^2$ on scarified skin of guinea pigs, scales are formed. Spontaneous recovery after 18-14 20 days. | The strain is virulent. 9–10 days after application of a dose of 500 –600 thousand cells of fungal material per $cm^2$ on scarified skin of guinea pigs, thin necrotic scabs are formed. Spontaneous recovery after 25–30 days. |

TABLE A-continued

| Properties and characteristics of the strains | Strain No. DSM-9469 | Epidemic Strain No. 533 |
|---|---|---|
| Reaction response | Result of intramuscular infection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

TABLE B

| Properties and characteristics of the strains | Strain No. DSM-9470 | Epidemic Strain No. 535 |
|---|---|---|
| Description of the culture | Mature 15-day colony on agar Sabouraud: white velvety-fluffy in centre, folded, margin of colony regular, under surface colourless or rose, diameter of colony 25–30 mm | 20-day colony on agar Sabouraud: white, fluffy, margin of colony regular, under surface yellow, 20 mm in diameter |
| Morphological characteristics | Mature 15-day culture with septate branching hyphae 1–3 μm wide, round oval puriform microconidia measuring 2–3 × 3–7 μm. | 20-day culture with septate branching hyphae 1–3 μm wide, microconidia clavate to round in small open clusters and along the hyphae measuring 2–3 × 6 μm; macroconidia are absent. |
| Pathogenic characteristics | The strain is weakly virulent. 9–10 days after application of a dose of 500–600 thousand cells of fungal material per cm² on scarified skin of guinea pigs, necrotic scabs are formed. Spontaneous recovery after 22–25 days. | The strain is virulent. 9–10 days after application of a dose of 500–600 thousand cells of fungal material per cm² on scarified skin of guinea pigs, thin necrotic scabs are formed. Spontaneous recovery after 25–30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

TABLE C

| Properties and characteristics of the strains | Strain No. DSM-9471 | Epidemic Strain No. 620 |
|---|---|---|
| Description of the culture | Mature 15-day colony on agar Sabouraud: white, velvety, elevated, margin of colony regular, under surface yellow, in centre deep purple, diameter of colony 32–35 mm | 20-day colony on agar Sabouraud: white, downy, elevated, margin of colony regular, under surface purple, diameter of colony 20–25 mm |
| Morphological characteristics | Mature 15-day culture with septate branching hyphae 1–3 μm wide, round oval puriform microconidia measuring 2–3 × 3–7 μm. | 20-day culture with septate branching hyphae 1–3 μm wide, microconidia clavate to round in small open clusters and along the hyphae measuring 2–3 × 3–6 μm; macroconidia are rare, long and pencil-shaped with 3–5 cross walls measuring 4–7 × 15–50 μm. |
| Pathogenic characteristics | The strain is weakly virulent. 9–10 days after application of a dose of 500–600 thousand cells of fungal materials per cm² on scarified skin of guinea pigs, scales are formed. Spontaneous recovery after 18–20 days. | The strain is virulent. 9–10 days after application of a dose of 500–600 thousand cells of fungal materials per cm² on scarified skin of guinea pigs, thin necrotic scabs are formed. Spontaneous recovery after 25–30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

TABLE D

| Properties and characteristics of the strains | Strain No. DSM-9472 | Epidemic Strain No. 754 |
|---|---|---|
| Description of the culture | Mature 15-day colony on agar Sabouraud: white velvety, in centre folded, margin of colony regular, under surface yellow in centre purple, diameter of colony 35–40 mm | 20-day colony onDn agar Sabouraud: white-rose, downy, margin of colony regular, under surface purple, diameter of colony 20–25 mm |
| Morphological characteristics | Mature 15-day culture with septate branching hyphae 1–3 μm wide, round oval puriform microconidia measuring 2–3 × 3–7 μm. | 20-day culture with septate branching hyphae 1–3 μm wide, microconidia clavate to round in small open clusters and along the hyphae measuring 2–3 × 3–6 μm; macroconidia are rare, long and pencil-shaped with 3–5 cross walls measuring 4–7 × 15–50 μm. |
| Pathogenic | The strain is weakly virulent. 9–10 days after application of a dose of 500–600 thousand cells of fungal materials per cm² on scarified skin of guinea | The strain is virulent. 9–10 days after application of a dose of 500–600 thousand cells of fungal materials per cm² on scarified skin of guinea pigs, thin necrotic scabs |

TABLE D-continued

| Properties and characteristics of the strains | Strain No. DSM-9472 | Epidemic Strain No. 754 |
|---|---|---|
| | pigs, scales are formed. Spontaneous recovery after 18–20 days. | are formed. Spontaneous recovery after 25–30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

TABLE E

| Properties and characteristics of the strains | Strain No. DSM-9456 | Epidemic Strain No. 008-L |
|---|---|---|
| Description of the culture | 10-day single-spore colony on agar Sabouraud: cream smooth and pasty glistening, elevated, margin of colony regular, diameter of colony 20–30 mm | 10-day single-spore colony on agar Sabouraud: cream soft and smooth with feathery offshots at the edges, diameter of colony 10–15 mm |
| Morphological characteristics | 10-day culture with spherical oval blastospores measuring 3.5–6 × 6–10 $\mu$m, chlamidospores 12–15 $\mu$m wide, pseudohyphae 5/14 8 $\mu$m wide, hyphae 1.5–3 $\mu$m wide | 10-day single-spore culture on agar Sabouraud with spherical oval budding blastospores measuring 3–5 × 5–8 $\mu$m, chlamidospores 10–15 $\mu$m diameter, pseudohyphae 5–8 $\mu$m wide, hyphae 1.5–3 $\mu$m wide. |
| Pathogenic characteristics | The strain is weakly virulent. 30 days after intraperitoneal injection of a dose of 10–100 million fungal cells to white mice, granuloma in abdominal organs of 50% of animals are formed. Lethal effect was not observed. | The strain is weakly virulent. 30 days after intraperitoneal injection of a dose of 10–100 million fungal cells to white mice, granuloma in abdominal organs of 80–100% of animals are formed. Lethal effect in 50–70% was observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Result of immunisation of a group of white mice with inactivated antigen from cultures (repeated not less than 10 times): establishes immunity | Result of immunisation of a group of white mice with inactivated antigen from cultures (repeated not less than 10 times): establishes immunity |

TABLE F

| Properties and characteristics of the strains | Strain No. DSM-9457 | Epidemic Strain No. 012 |
|---|---|---|
| Description of the culture | 10-day single-spore colony on agar Sabouraud: cream rough elevated, margin of colony lobulated, diameter of colony 20–23 mm | 10-day single-spore colony on agar Sabouraud: cream rough elevated, margin of colony fringed and lobulated, diameter of colony 15–20 mm |
| Morphological characteristics | 10-day single-spore culture with spherical oval blastospores measuring 3.5–5 × 5–10 $\mu$m, chlamidospores 12 . $\mu$m wide, pseudohyphae 4–7 $\mu$m wide, hyphae 2–3 $\mu$m wide | 10-day single-spore culture with spherical oval budding blastospores measuring 3–5 × 5–8 $\mu$m, chlamidospores 10 . $\mu$m diameter, pseudohyphae 5–8 $\mu$m wide, hyphae-1.5–3 $\mu$m wide |
| Pathogenic characteristics | The strain is weakly virulent. 30 days after intraperitoneal injection of a dose of 10–100 million fungal cells to white mice, granuloma in abdominal organs in 30% of animals are formed. Lethal effect was not observed. | The strain is weakly virulent. 30 days after intraperitoneal injection of a dose of 10–100 million fungal cells to white mice, granuloma in abdominal organs of 50% of animals are formed. Lethal effect not more 50% were observed. |
| Reaction response | Result of intramuscular injection of inactivated corpuscular antigens from cultures: no observed changes in clinical state of animals | Result of intramuscular injection of inactivated corpuscular antigens from cultures: no observed changes in clinical state of animals |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

TABLE G

| Properties and characteristics of the strains | Strain No. DSM-9458 | Epidemic Strain No. 047 |
|---|---|---|
| Description of the culture | 10-day single-spore colony on agar Sabouraud: cream smooth and pasty glistening, elevated, margin of colony regular, diameter of colony 16–18 mm | 10-day single-spore colony on agar Sabouraud: cream soft and smooth with feathery offshots at the edges, diameter of colony 10–15 mm |
| Morphological characteristics | 10-day culture with spherical oval blastospores measuring 3.6–6 × 6–11 $\mu$m, chlamidospores 12–15 $\mu$m wide, pseudohyphae 4–8 $\mu$m wide, hyphae 1.5–3 $\mu$m wide | 10-day single-spore culture on agar Sabouraud with spherical oval budding blastospores measuring 3–5 × 5–8 $\mu$m, chlamidospores 10–15 $\mu$m diameter, pseudohyphae 5–8 $\mu$m wide, hyphae 1.5–3 $\mu$m wide. |
| Pathogenic characteristics | The strain is weakly virulent. 30 days after intraperitoneal injection of a dose of 10–100 million fungal cells to white mice, granuloma in abdominal organs of 50–100% of animals are | The strain is weakly virulent. 30 days after intraperitoneal injection of a dose of 10–100 million fungal cells to white mice, granuloma in abdominal organs of 80–100% of animals are formed. |

TABLE G-continued

| Properties and characteristics of the strains | Strain No. DSM-9458 | Epidemic Strain No. 047 |
|---|---|---|
| | formed. Lethal effect in 50% were observed. | Lethal effect in 70–100% were observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

TABLE H

| Properties and characteristics of the strains | Strain No. DSM-9459 | Epidemic Strain No. 158 |
|---|---|---|
| Description of the culture | 10-day single-spore colony on agar Sabouraud: cream smooth pasty glistening, elevated, margin of colony regular, diameter of colony 16–18 mm | 10-day single-spore colony on agar Sabouraud: cream smooth pasty, margin of colony lobulated and with feathery offshots at the edges, diameter of colony 10–15 mm |
| Morphological characteristics | 10-day culture with spherical oval blastospores measuring 3.6–6 × 6–11 $\mu$m, chlamidospores 12–15 $\mu$m wide, pseudohyphae 4–8 $\mu$m wide, hyphae 1.5–3 $\mu$m wide | 10-day single-spore culture on agar Sabouraud with spherical oval budding blastospores measuring 3–5 × 5–8 $\mu$m, chlamidospores 10–15 $\mu$m diameter, pseudohyphae 5–8 $\mu$m wide, hyphae 1.5–3 $\mu$m wide. |
| Pathogenic characteristics | The strain is weakly virulent. 30 days after intraperitoneal injection by dose of 10–100 million fungal cells to white mice, granuloma in abdominal organs of 40% of animals are formed. Lethal effect was not observed. | The strain is weakly virulent. 30 days after intraperitoneal injection by dose of 10–100 million fungal cells to white mice, granuloma in abdominal organs of 50% of animals are formed. Lethal effect in 20–50% was observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

Compared with the severity score values of the control group the efficacy of Complex III-I was 78.2%, 48.0%, 100% and 100%, Complex III-II 72.7%, 50.0%, 100% and 100%, Complex III-III 36.4%, 20.0%, 50.0% and 0%, Complex III-IV 9.1%, 20.0%, 43.8% and 37.5%, Complex III-V 34.5%, 36.0%, 35.0% and 20.0% after 7, 16, 21 and 28 days respectively. Note the low severity score value and fast healing process in animals vaccinated with Complexes III-I and III-II.

Figure 4:
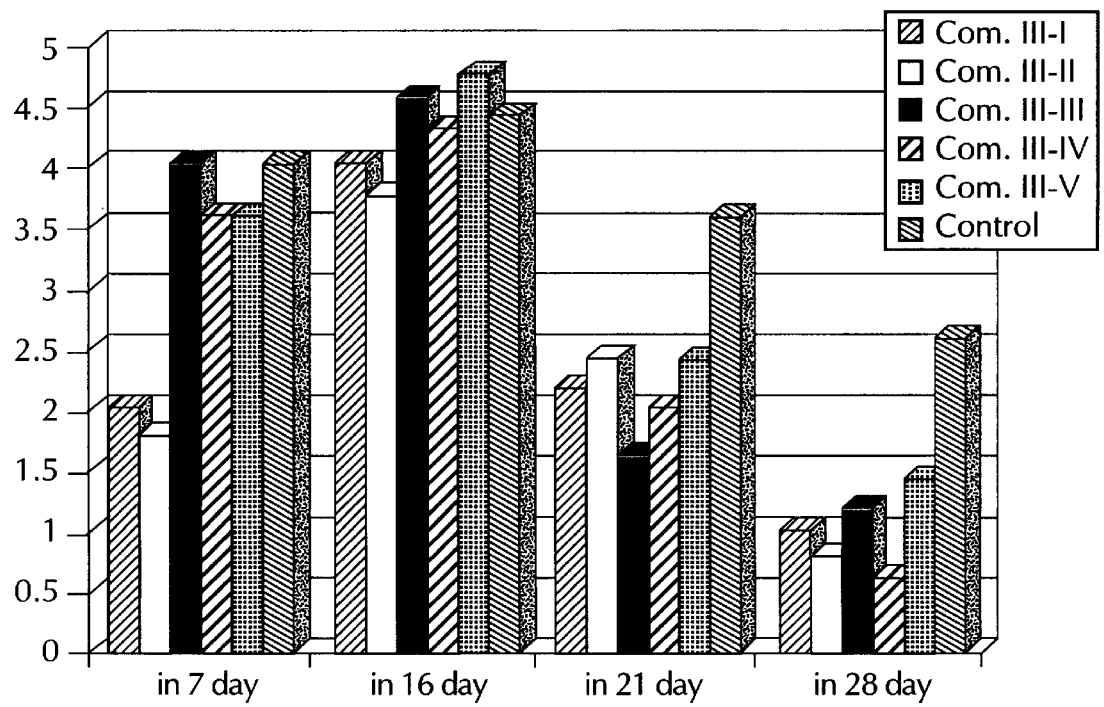

FIG. 4. The dynamics of clinical symptoms of *Trichophyton mentagrophytes* infections in guinea pigs (3rd experiment, Complex III-I, III-II, III-III, III-IV and III-V).

Compared with the severity score values of the control group the efficacy of Complex III-I was 50.0%, 9.1%, 37.5% and 71.5%, Complex III-II 55%, 13.6%, 33.3% and 69.2%, Complex III-III 0%, 0%, 65.6% and 63.9%, Complex III-IV 10.0%, 2.3%, 44.4% and 76.9%, Complex III-V 10.0%, 0%, 33.3% and 46.2% after 7, 16, 21 and 28 days respectively.

In guinea pigs vaccinated with complex III-I and III-II severity scores of clinical symptoms, when compared with values obtained from control animals, were lower during the complete observation period. Guinea pigs vaccinated with complex III-III, III-IV or II-V had intensive symptoms of a *Trichophyton mentagrophytes* infection on days 7 and 16 but in comparison with control animals these symptoms were markedly reduced at the following observation dates.

Figure 5:
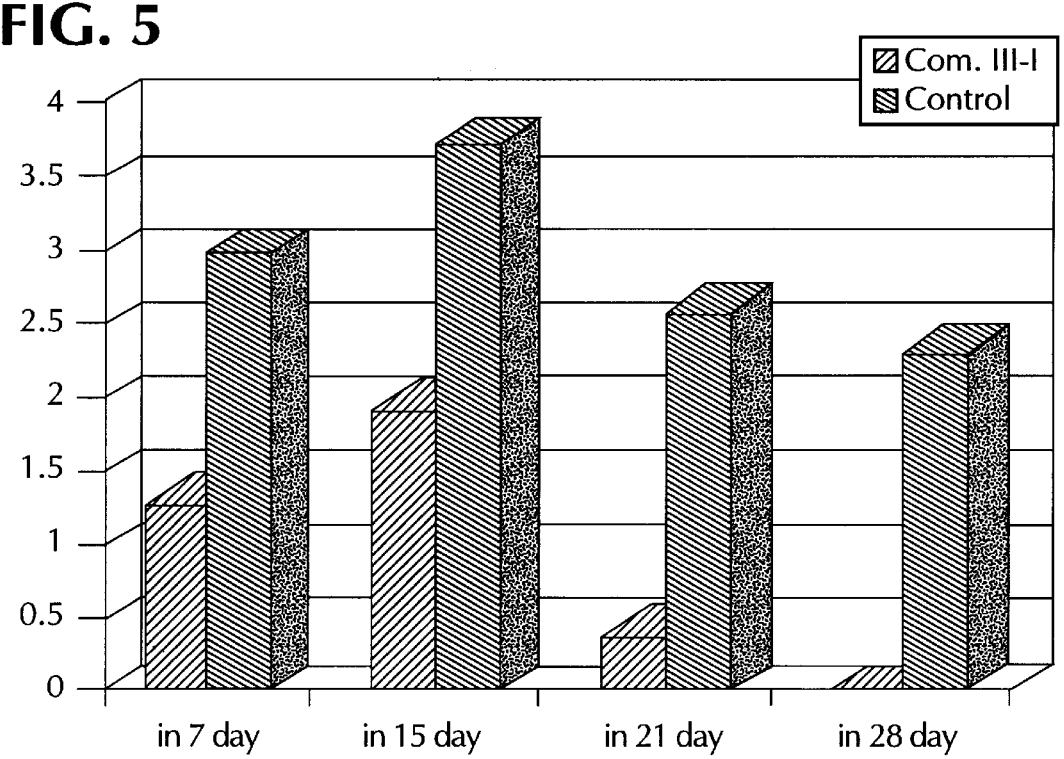

FIG. 5. The dynamics of clinical symptoms of *Trichophyton rubrum* infections in rabbits (1st experiment, Complex II-I).

Compared with the severity score values of the control group the efficacy of Complex II-I was 53.3%, 47.4%, 84.6% and 100% after 7, 15, 21 and 28 days respectively.

Figure 6:
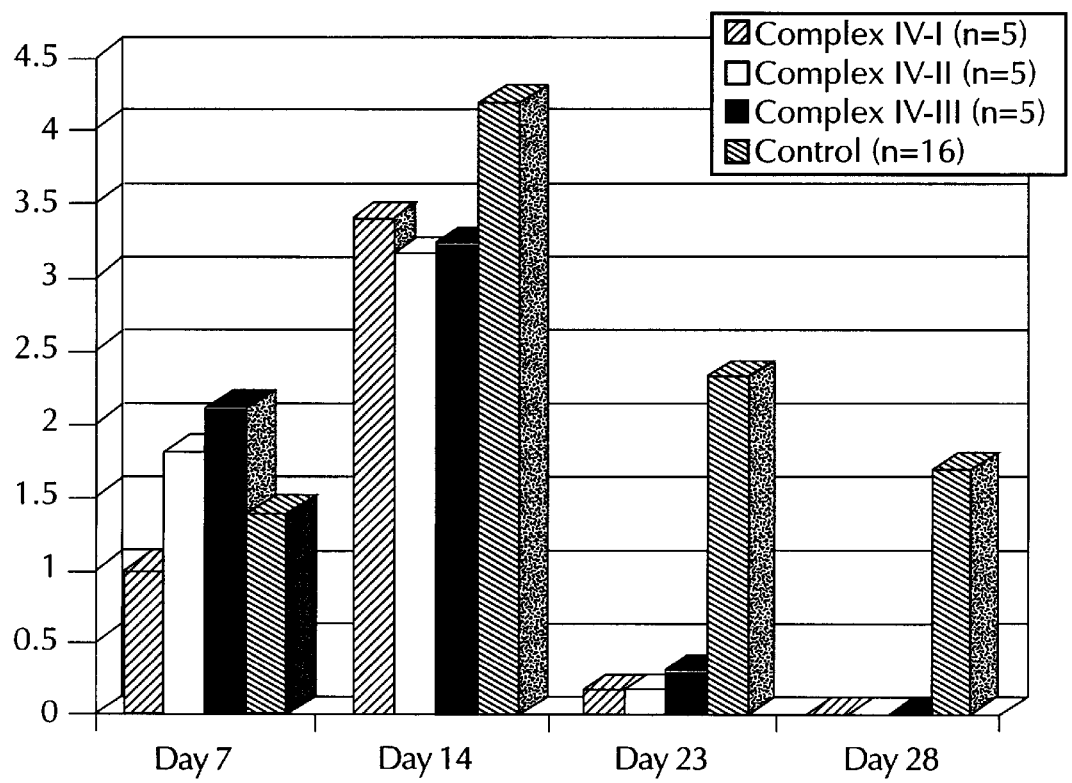

FIG. 6. The dynamics of clinical symptoms of *Trichophyton rubrum* infections in guinea pigs (Complex IV-I, IV-II and IV-II).

Compared with the severity score values of the control group the efficacy of Complex IV-I was 28.6%, 19.1%, 91.3% and 100%, Complex IV-II–28.6%, 23.8%, 91.3% and 100%, Complex IV-III–50%, 21.4%, 87.0% and 100% after 7, 14, 23 and 28 days respectively.

The clinical symptoms of trichophytosis after 7 days were more intensive for animals vaccinated by Complexes IV-II and IV-III than for unvaccinated controls but severity score values (mean) of vaccinated guinea pigs (Complex IV-I, IV-II, and IV-III) were significantly less than the values of the control group after 14, 23 and 28 days respectively.

Figure 7:
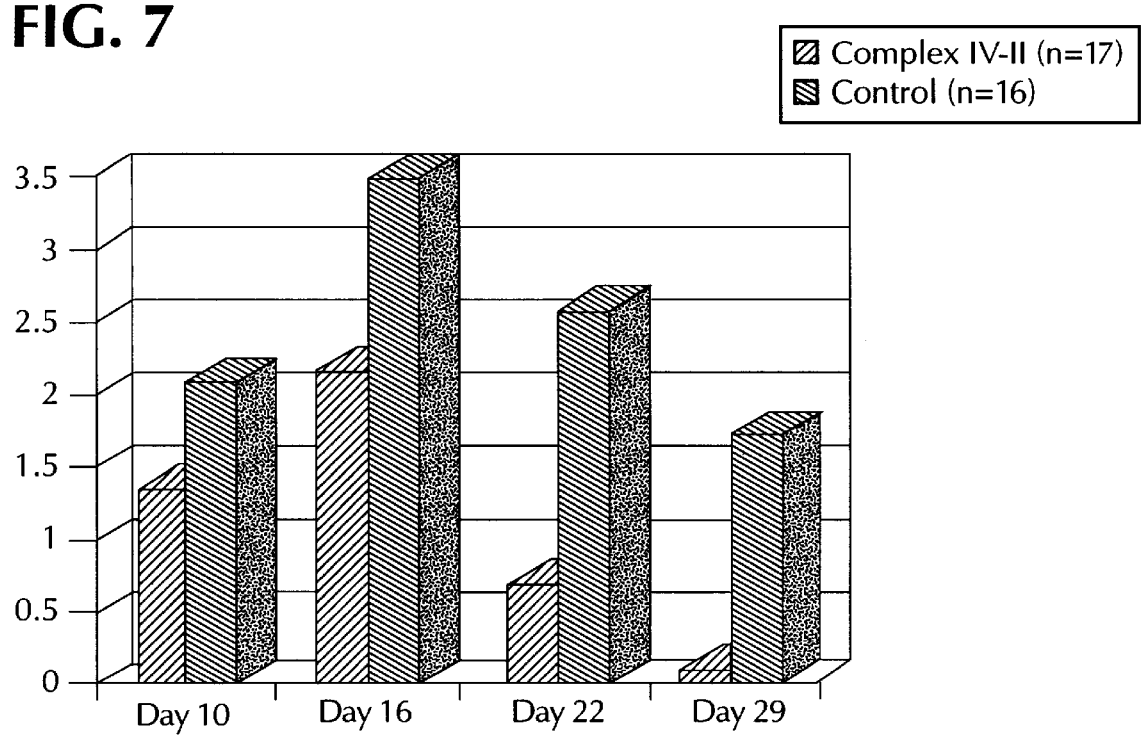

FIG. 7. The dynamics of clinical symptoms of *Trichophyton rubrum* infections in guinea pigs (Complex IV-II).

Compared with the severity score values of the control group the efficacy of Complex IV-II was 33.3%, 37.1%, 73,1% and 94.1% after 10, 16, 22 and 29 days respectively.

Figure 8:
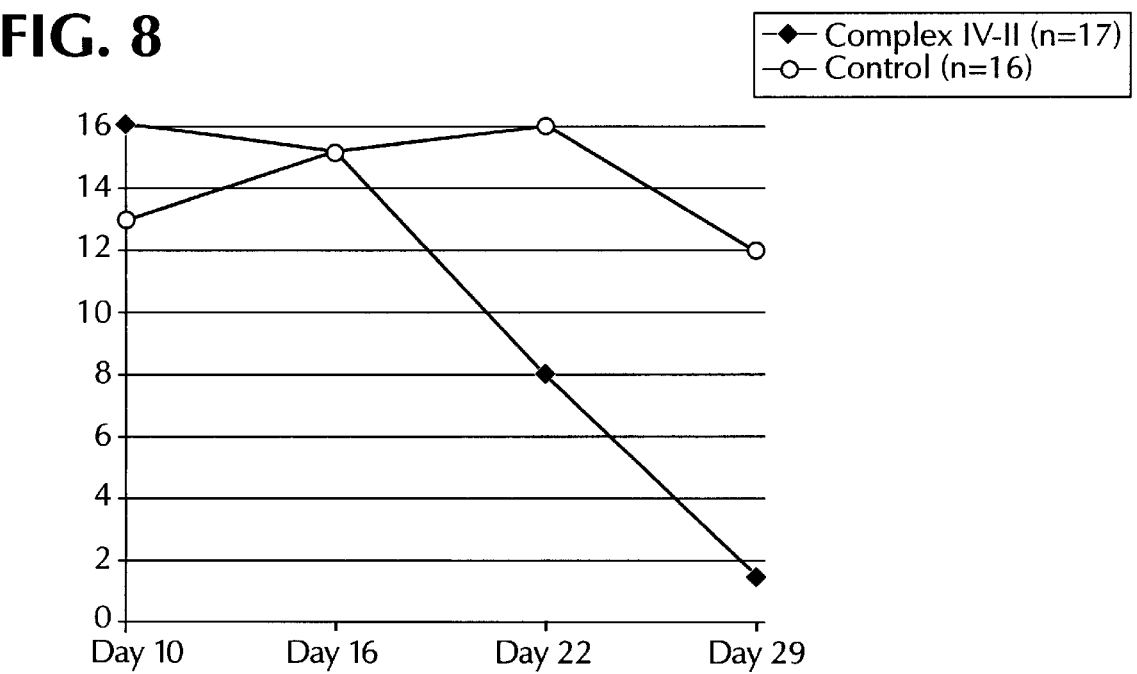

FIG. 8. The dynamics of the number of guinea pigs with clinical symptoms of *Trichophyton rubrum* infections (Complex IV-II).

The number of guinea pigs vaccinated with Complex IV-II with clinical symptoms of *Trichophyton rubrum* infections is compared to the number of unvaccinated controls after different observation periods.

Figure 9:
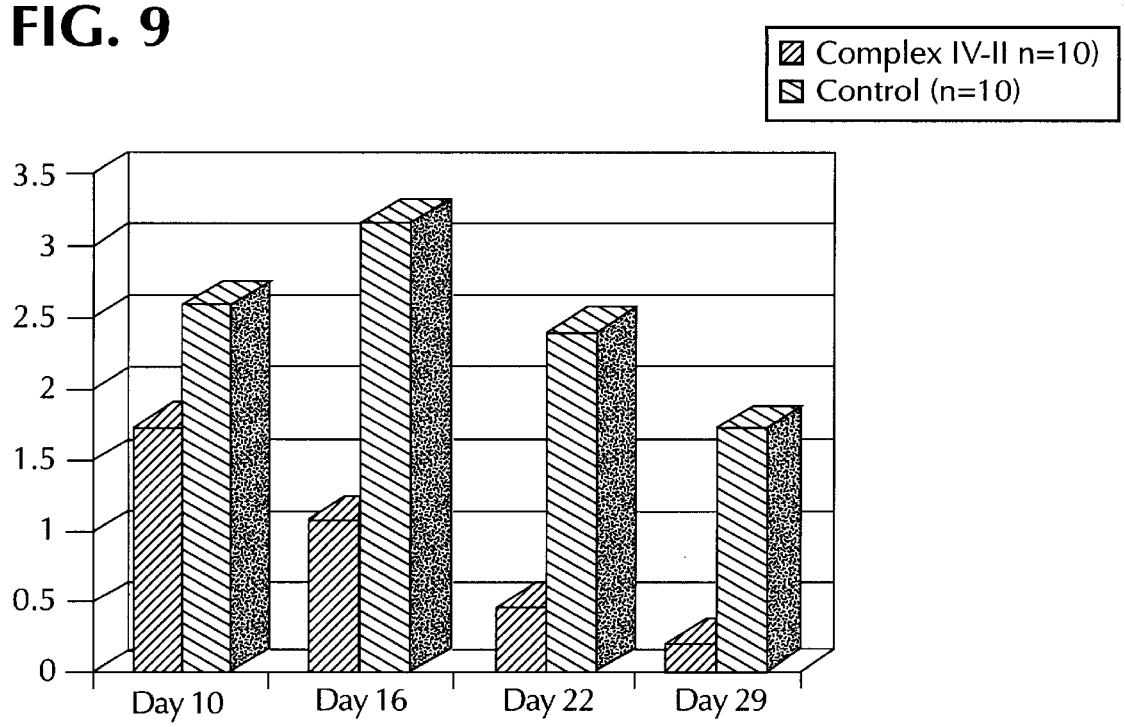

FIG. 9. The dynamics of clinical symptoms of *Trichophyton rubrum* infections in rabbits (Complex IV-II).

Compared with the severity score values of the control group the efficacy of Complex IV-II was 30.8%, 65.6%, 79.2% and 88.9% after 10, 16, 22 and 29 day respectively.

Figure 10:
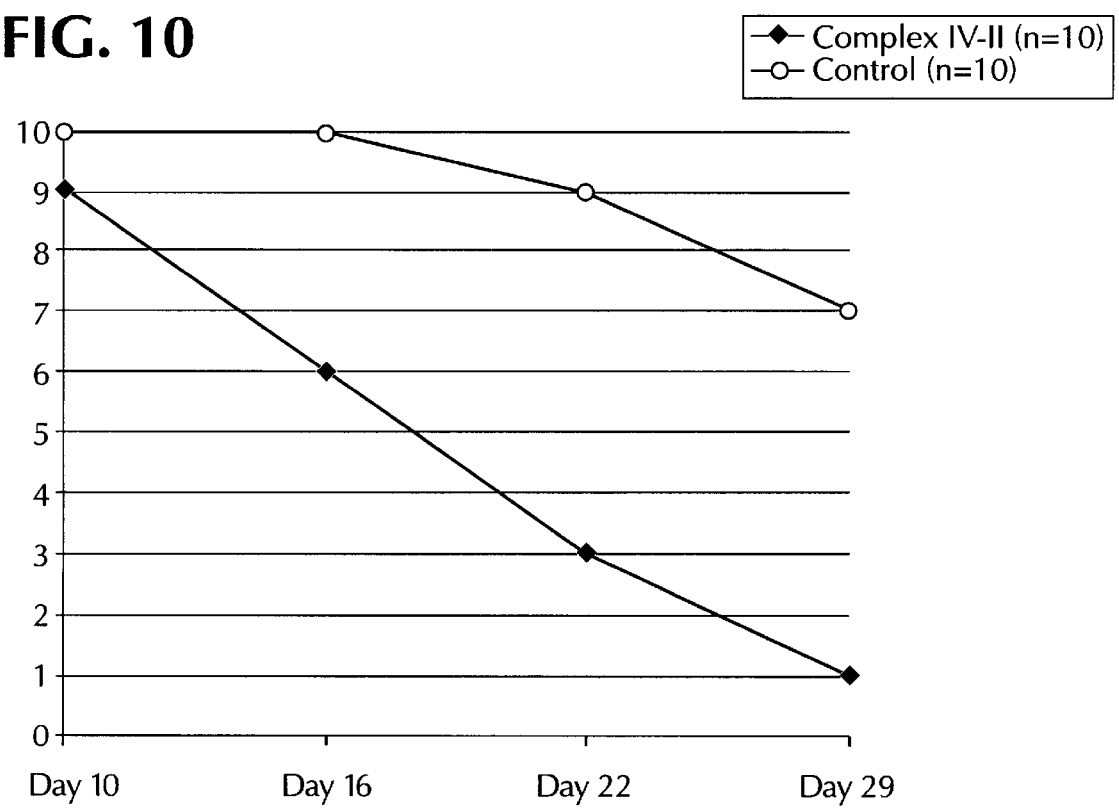

FIG. 10. The dynamics of the number of rabbits with clinical symptoms of *Trichophyton rubrum* infection.

The number of rabbits vaccinated with Complex IV-II with clinical symptoms of *Trichophyton rubrum* infections is compared to the number of unvaccinated controls after different observation periods.

Figure 11:
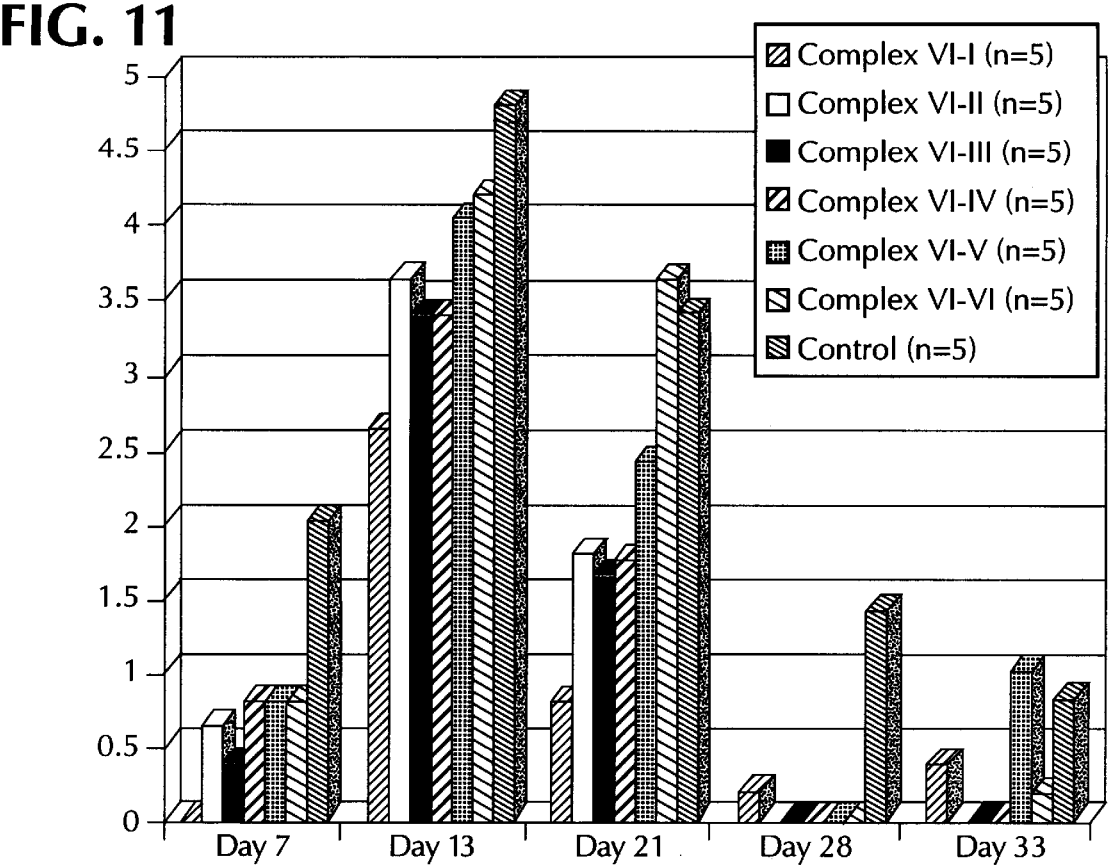

FIG. 11. The dynamics of clinical symptoms of *Trichophyton rubrum* infections in guinea pigs (Complex VI-I, VI-II, VI-III, VI-IV, VI-V, VI-VI).

Compared with the severity score values of the control group the efficacy of Complex VI-I was 100%, 45.8%, 76.5%, 85.7% and 50.0%, Complex VI-I 70.0%, 25.0%, 47.1%, 100% and 100%, Complex VI-III 80.0%, 29.2%, 52.9%, 100% and 100%, Complex VI-IV 60.0%, 29.2%, 48.5%, 100% and 100%, (Complex VI-V 60.0%, 16.7%, 29.4%, 100% and −25%, Complex VI-VI 60.0%, 12.5%, 100% and 75.0% after 7, 13, 21, 28 and 33 days respectively.

Figure 12:
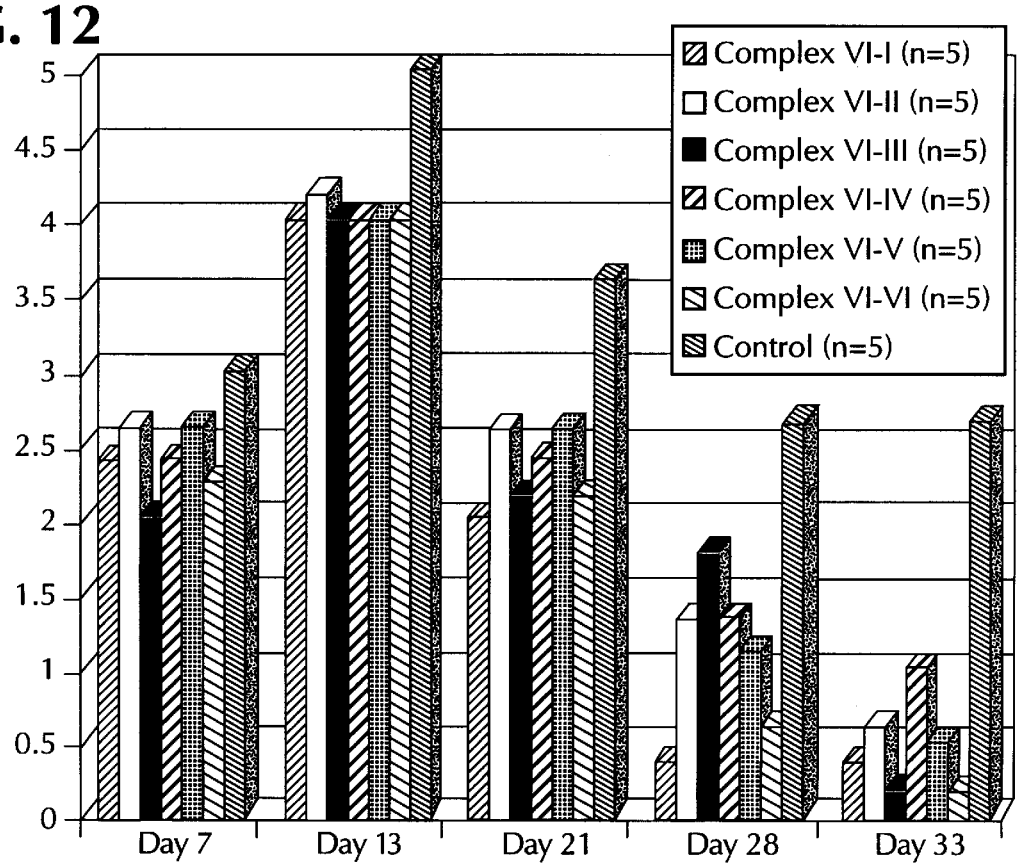

FIG. 12. The dynamics of clinical symptoms of *Trichophyton mentagrophytes* infections in guinea pigs (Complex VI-I, VI-II, VI-III, VI-IV, VI-V, VI-VI).

Compared with the severity score values of the control group the efficacy of Complex VI-I was 20.0%, 20.0%, 44.4%, 84.6 and 84.6%, Complex VI-II 13.3%, 16.0%, 27.8%, 46.2% and 76.9%, Complex VI-III 33.3%, 20.0%, 38.9%, 30.8% and 92.3%, Complex VI-IV 20.0%, 20.0%, 33.3%, 46.2% and 61.5%, Complex VI-V 13.3%, 20.0%, 27.8%, 53.8% and 80.8%, Complex VI-VI 26.7%, 20.0%, 38.9%, 76.9% and 92.3% after 7, 13, 21, 28 and 33 days respectively.

Figure 13:
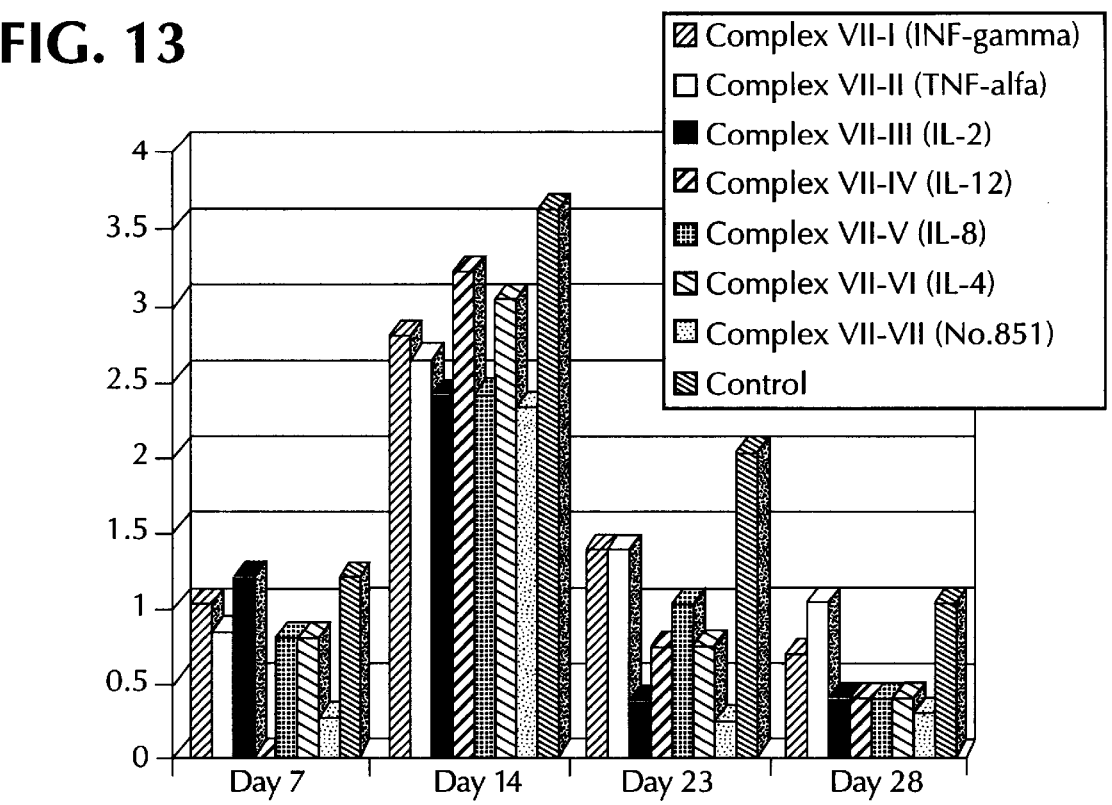

FIG. 13. The dynamics of clinical symptoms of *Trichophyton rubrum* infections in guinea pigs (Complex VII-I, VII-II, VII-II, VII-IV, VII-V, VII-VI, VII-VII).

Compared with the severity score values of the control group the efficacy of Complex VII-I was 16.7%, 22.2%, 30.0% and 40.0%, Complex VII-II 33.3%, 27.8%, 30.0% and 0%, Complex VII-III 0.0%, 33.3%, 80.0% and 60.0%, Complex VII-IV 100%, 11.1%, 60.0% and 60.0%, Complex VII-V 33.3%, 33.3%, 50.0% and 60.0%, Complex VII-VI 33.3%, 16.7%, 60.0% and 60.0%, Complex VII-VII 75.0%, 36.1%, 85.0% and 70.0% after 7, 14, 23 and 28 days respectively.

Figure 14:
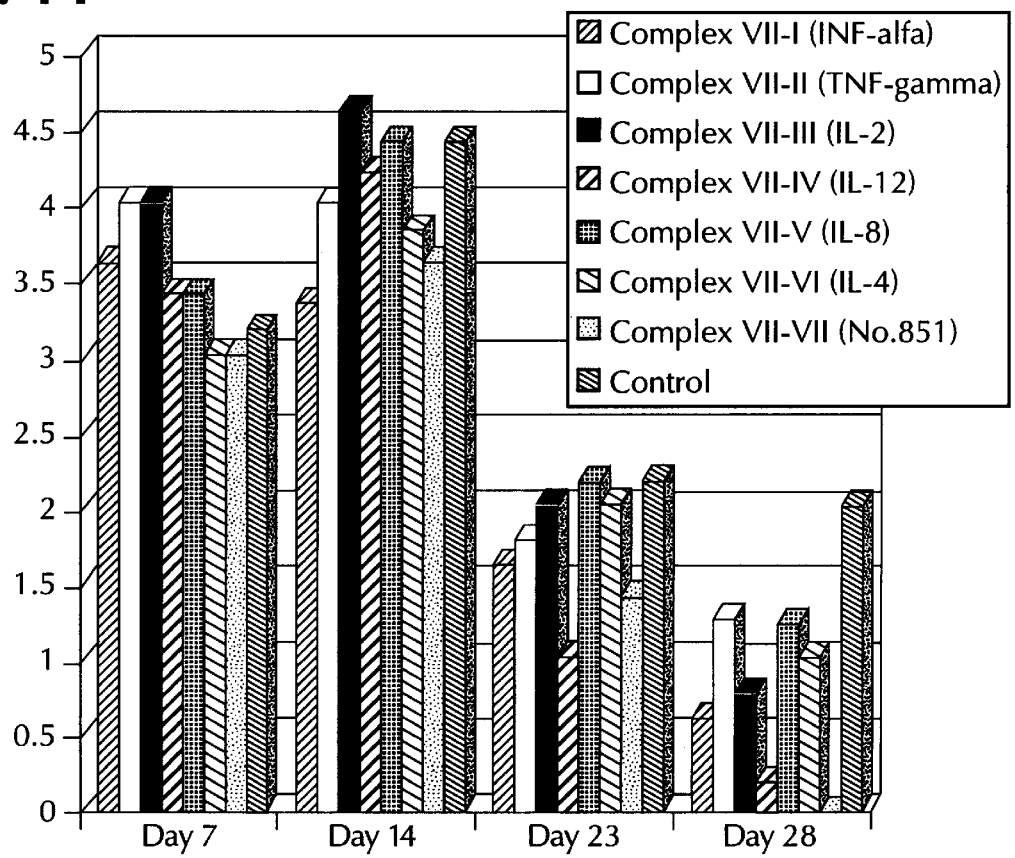

FIG. 14. The dynamics of clinical symptoms of *Trichophyton mentagrophytes* infections in guinea pigs (Complex VII-I, VII-II, VII-III, VII-IV, VII-V, VII-VI, VII-VII).

Compared with the severity score values of the control group the efficacy of Complex VII-I was −12.5%, 22.7%, 27.3% and 70.0%, Complex VII-II−25%, 9.1%, 18.2% and 37.5%, Complex VII-III−25%, 4.5, 9.1% and 60.0%, Complex VII-IV 6.3%, 4.5%, 54.5% and 90.0%, Complex VII-V −6.3%, 0%, 0%, and 40.0%, Complex VII-VI 6.3%,13.6%, 9.1% and 50.0%, Complex VII-VII 6.3%, 18.2%, 36.4% and 100% after 7, 14, 23 and 28 days respectively.

Figure 15:
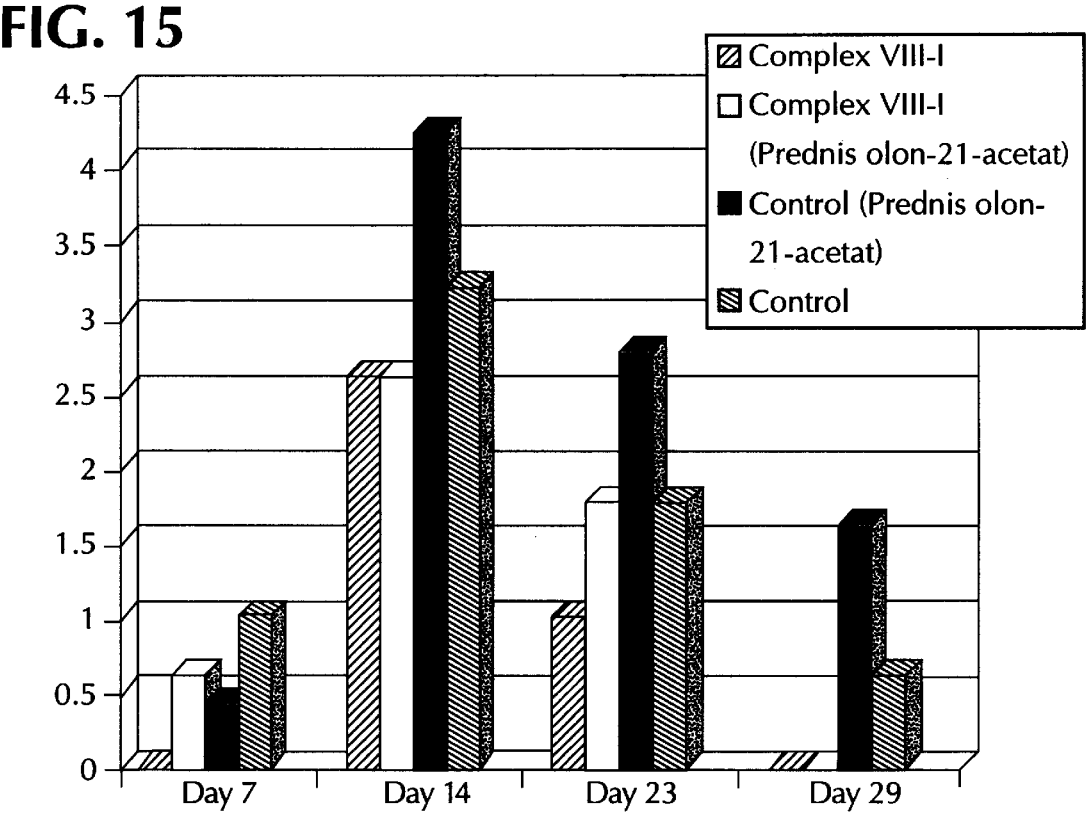

FIG. 15: The dynamics of clinical symptoms of *Trichophyton rubrum* infections in guinea pigs (Complex VII-I, VIII-I+H, Control+H; H refers to animals treated with Hostacortin H(Prednisolon-acetate)).

Compared with the severity score values of the untreated control group the efficacy of Complex VIII-I was 100%, 27.8%, 33.3% and 100%, Complex VIII-+H 40.0%, 27.8%, 0% and 100% after 7, 14, 20 and 29 days respectively. Compared with the severity score values of the control group treated with Hostacortin H(Prednisolon-acetate) the efficacy of Complex VII-I was 100%, 38.1%, 57.1% and 100%, Complex VIII-I+H −50%, 38.1%, 35.7% and 100% after 7,14, 20 and 29 days respectively.

Figure 16:
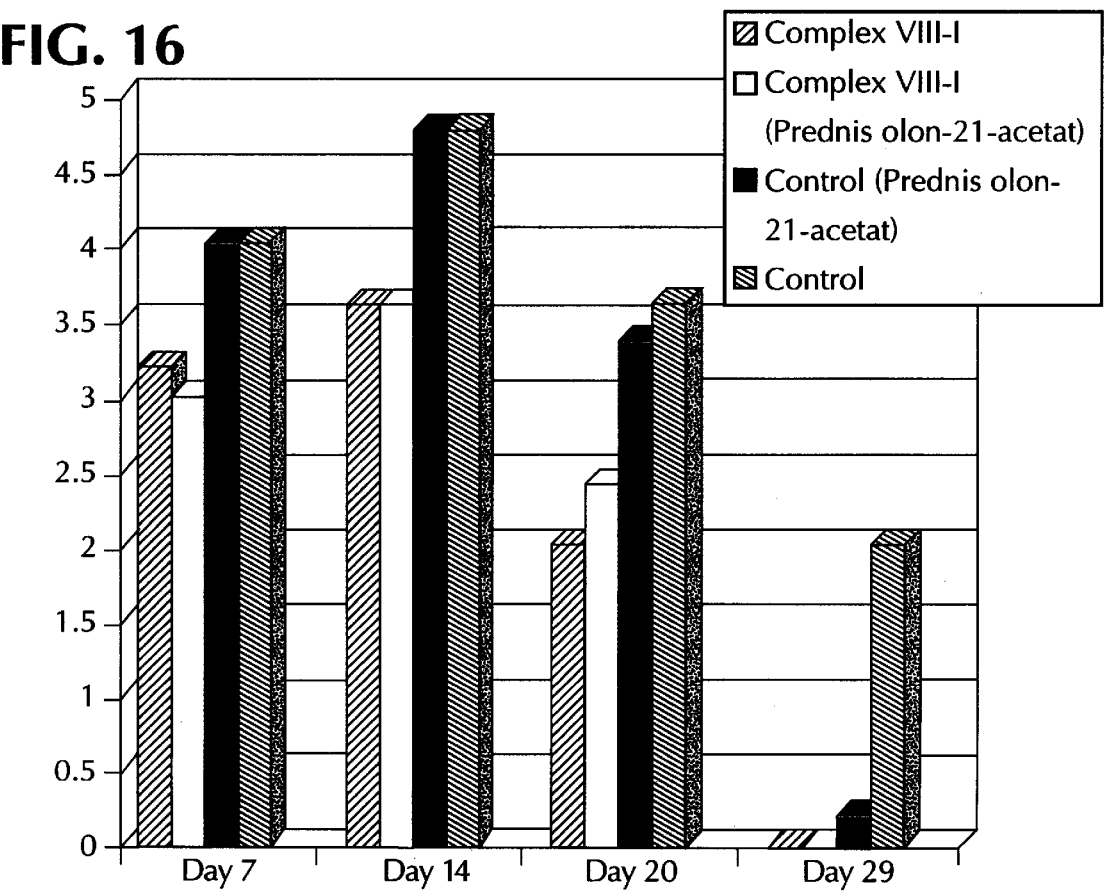

FIG. 16. The dynamics of clinical symptoms of *Trichophyton mentagrophytes* infections in guinea pigs (Complex VII-I, VIII-I+H, Control+H; H refers to animals treated with Hostacbrtin H(Prednisolon-acetate)).

Compared with the severity score values of the untreated control group the efficacy of Complex VIII-I was 20.0%, 25.0%, 44.4% and 100%, Complex VIII-I+H 25.0%, 25.0%, 33.3% and 100% after 7, 14, 20 and 29 days respectively. Compared with the severity score values of the control group treated with Hostacortin H(Prednisolon-acetate) the efficacy of Complex VII-I was 20.0%, 25.0%, 41.2% and 100%, Complex VIII-I+H 25.0%, 25.0%, 29.4 and 100% after 7, 14, 20 and 29 days respectively.

Figure 17:
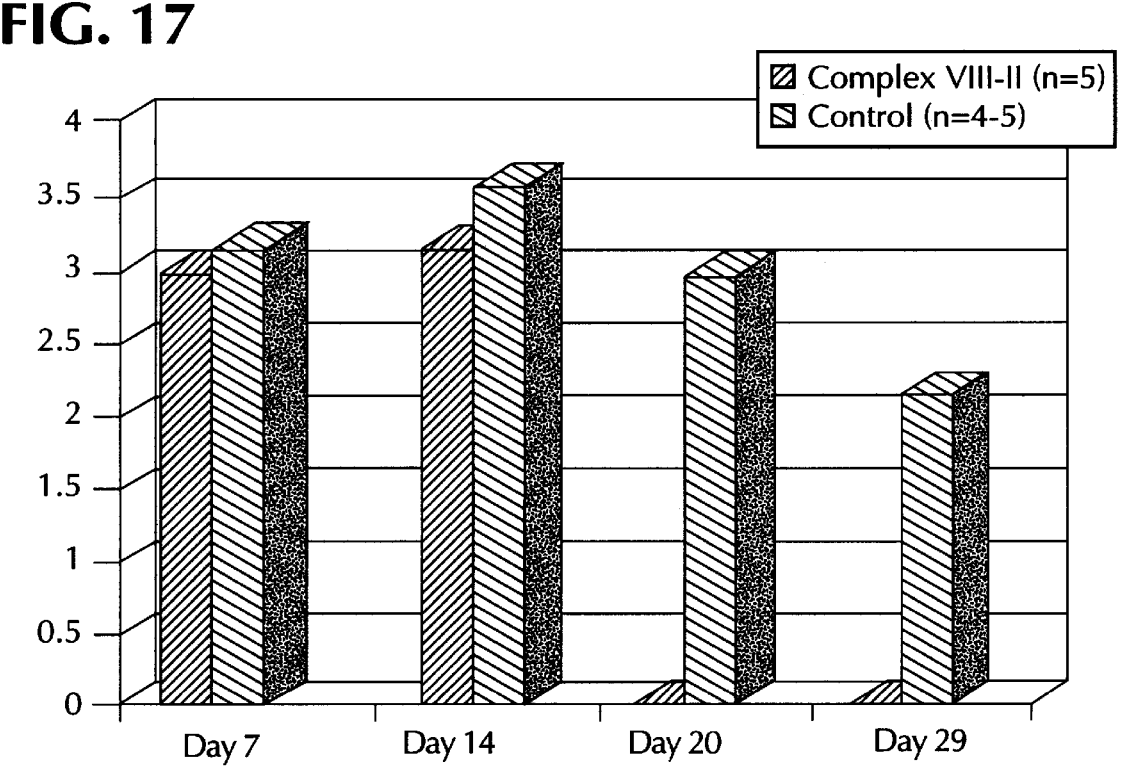

FIG. 17. The dynamics of clinical symptoms of *Candida albicans* infections in guinea pigs (Complex VIII-I).

Compared with the severity score values of the untreated control group the efficacy of Complex VIII-I was 6.3%, 11.1%, 100% and 100% after 7, 14, 20 and 29 days respectively.

Figure 18:
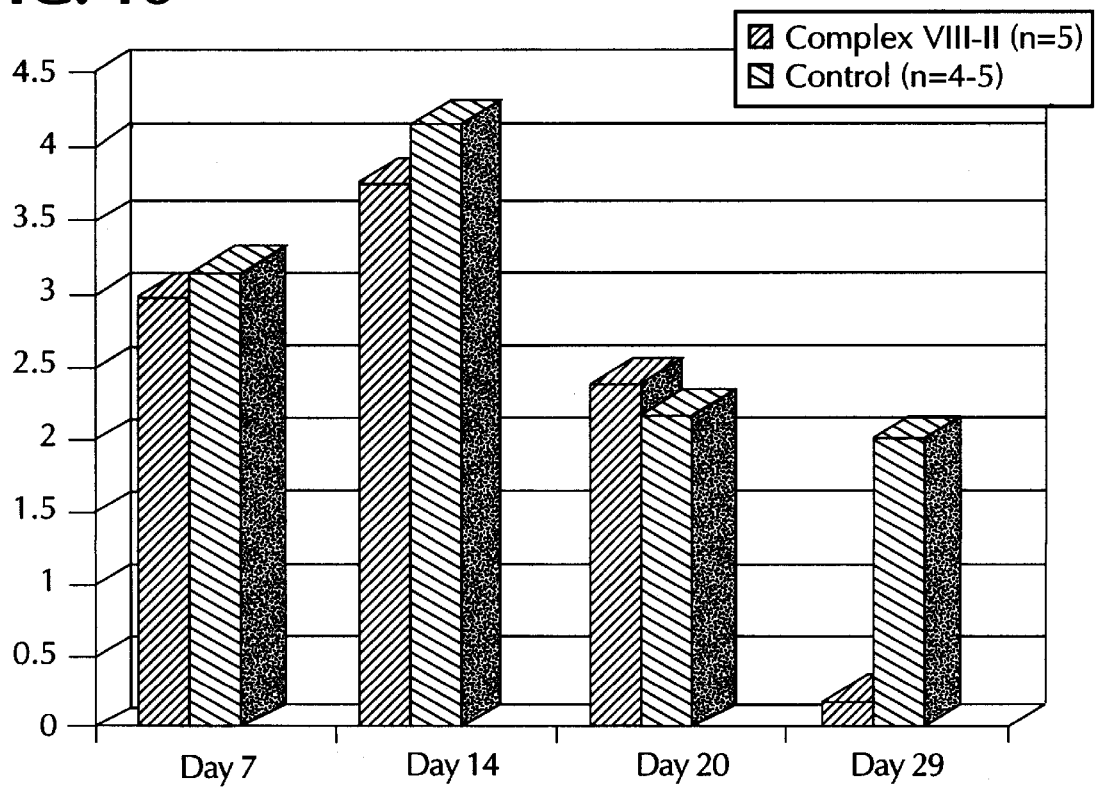

FIG. 18. The dynamics of clinical symptoms of *Microsporum canis* infections in guinea pigs (Complex VIII-II).

Compared with the severity score values of the untreated control group the efficacy of Complex VII-II was 6.3%, 9.5%, −9.1% and 90.0% after 7, 14, 20 and 29 days respectively.

Figure 19:
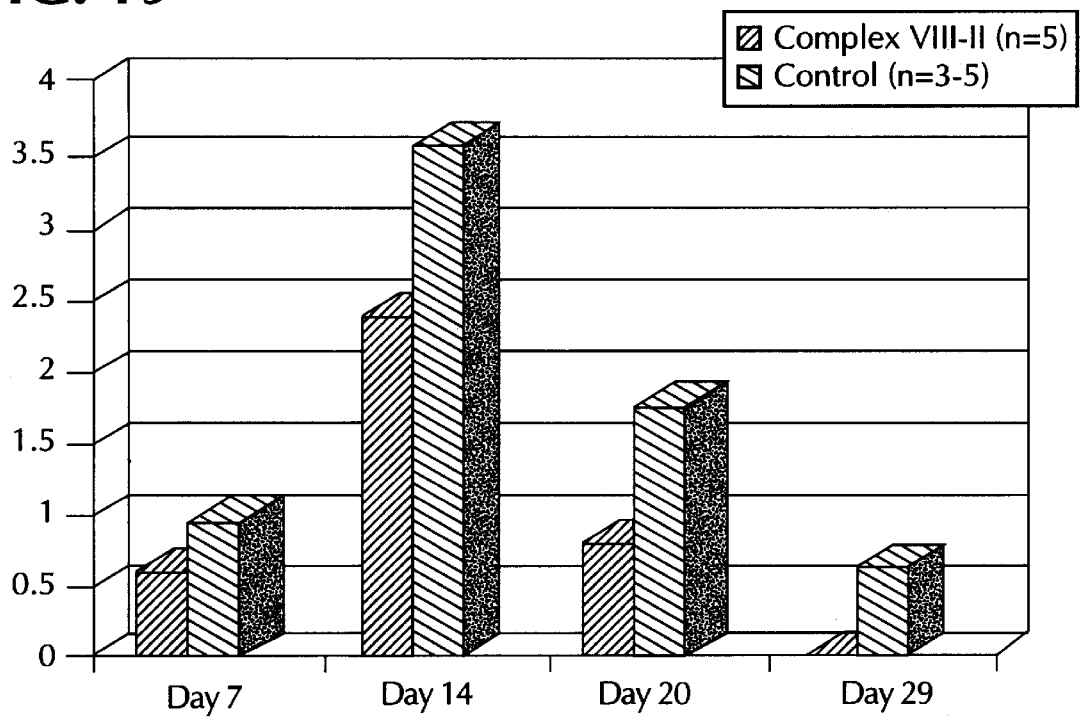

FIG. 19. The dynamics of clinical symptoms of *Trichophyton rubrum* infections in guinea pigs (Complex VII-II).

Compared with the severity score values of the untreated control group the efficacy of Complex VIII-II was 40.0%, 33.3%, 55.6% and 100% after 7, 14, 20 and 29 days respectively.

Figure 20:
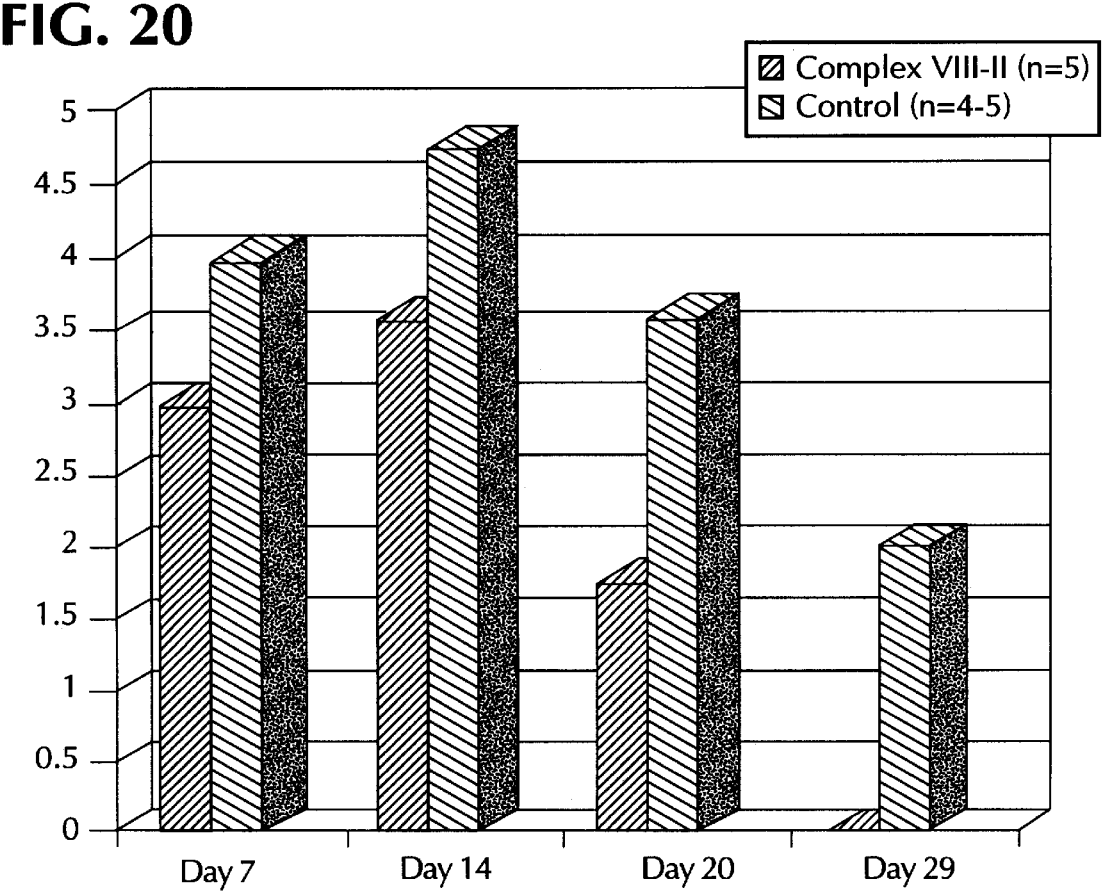

FIG. 20. The dynamics of clinical symptoms of *Trichophyton mentagrophytes* infections in guinea pigs (Complex VII-III).

Compared with the severity score values of the untreated control group the efficacy of Complex VII-II was 25.0%, 25.0%, 50.0% and 100% after 7, 14, 20 and 29 days respectively.

EXAMPLES

Example 1

Cultures of the strains *Trichophyton mentagrophytes* DSM-7279, *Trichophyton rubrum* DSM-9472 and *Candida albicans* DSM-9456 were used to prepare 1.5 liters of vaccine. *Trichophyton mentagrophytes* DSM-7279 and *Trichophyton rubrum* DSM-9472 were cultivated separately on malt extract agar in 3 Roux flasks for each culture for 20 days at 28° C. *Candida albicans* DSM-9456 was cultivated in 2 Roux flasks on agar Sabouraud at 28° C. for 3 days. The fungal masses of the strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml for each homogenate. To yield 50 to 100% germ tubes each suspension of microconidia was fermented for 1–2 days at 28° C.

The blastospores of strain DSM-9456 were lifted off by washing with 500 ml of a physiological solution of sodium chloride. The concentration of blastospores in suspension was adjusted to 60 million per ml. 500 ml of each culture in suspension were combined and mixed in a single container. The homogenate was inactivated by adding thiomersal in a ratio of 1:20000 (w/v) directly to the cell suspension. For this purpose 75 mg of thiomersal were added to 1.5 liters of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine after Trichophyton challenge in guinea pigs and rabbits is shown in tables 9, 10, 11, 12, 13, 14, 15, 16, 17, 18 and FIGS. 2, 3, 4, 5 (Complex II-I, III-I, VI-I).

Example 2

Cultures of the strains *Trichophyton mentagrophytes* DSM-7279, *Trichophyton rubrum* DSM-9472 and *Candida albicans* DSM-9456 were used to prepare 1.5 liters of vaccine. *Trichophyton mentagrophytes* DSM-7279 and *Trichophyton rubrum* DSM-9472 were cultivated separately on malt extract agar in 3 Roux flasks for each culture for 20 days at 28° C. The *Candida albicans* DSM-9456 was cultivated in 2 Roux flasks on agar Sabouraud at 28° C. for 3 days.

The fungal masses of the strains DSM-7279 and 9472 were lifted off and separately homogenised in 500 ml of an aqueous solution 0.3% fermented hydrolyzed muscle protein, 5% glucose and 0.1% yeast extract. The concentration of microconidia was adjusted to 60 million per ml for each homogenate. To yield 50 to 100% germ tubes each suspension of microconidia was fermented for 1–2 days at 28° C. Then the cell suspensions were washed with a physiological solution of sodium chloride 5 times by centrifugation (4000 rpm) at 10° C. for 25 minutes for each centrifugation step.

The blastospores of strain DSM-9456 were lifted off by washing with 500 ml of a physiological solution of sodium chloride. The concentration of blastospores in suspension was adjusted to 60 million per ml.

Then 500 ml of each culture in suspension were combined and mixed in a single container. The homogenate was inactivated by adding thiomersal in a ratio of 1:20000 (w/v) directly to the cell suspension. For this purpose 75 mg of thiomersal were added to 1.5 liters of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine after Trichophyton challenge in guinea pigs is shown in tables 11, 12, 13, 14 and FIGS. 3, 4 (Complex III-II).

Example 3

Cultures of the strains *Trichophyton mentagrophytes* DSM-7279, *Trichophyton rubrum* DSM-9472 and *Candida albicans* DSM-9456 were used to prepare 1.5 liters of the vaccine. *Trichophyton mentagrophytes* DSM-7279 and *Trichophyton rubrum* DSM-9472 were cultivated separately on malt extract agar in 3 Roux flasks for each culture for 20 days at 28° C. The *Candida albicans* DSM-9456 was cultivated in 2 Roux flasks on agar Sabouraud at 28° C. for 3 days.

The fungal masses of the strains DSM-7279 and 9472 were lifted off and separately homogenised in 500 ml of an aqueous solution of 0.5% soy peptone, 5% glucose and 0.1% yeast extract. The concentration of microconidia was adjusted to 65 million per ml for each homogenate. To yield 50 to 100% germ tubes each suspension of microconidia was fermented for 1–2 days at 28° C. The blastospores of strain DSM-9456 were lifted off by washing with 500 ml of physiological solution of sodium chloride. The concentration of blastospores in suspension was adjusted to 60 million per ml. 500 ml of each culture in suspension were combined and mixed in a single container. The homogenate was inactivated by adding thiomersal in a ratio 1:20000 (w/v) directly to the cell suspension. For this purpose 75 mg of thiomersal were added to 1.5 liters of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine after Trichophyton challenge in guinea pigs is shown in tables 11, 12, 13, 14 and FIGS. 3, 4 (Complex II-II).

Example 4

Cultures of the strains *Trichophyton mentagrophytes* DSM-7279, *Trichophyton rubrum* DSM-9472 and *Candida albicans* DSM-9456 were used to prepare 1.5 liters of the vaccine. *Trichophyton mentagrophytes* DSM-7279 and *Trichophyton rubrum* DSM-9472 were cultivated separately on malt extract agar in 3 Roux flasks for each culture for 20 days at 28° C. The *Candida albicans* DSM-9456 was cultivated in 2 Roux flasks on agar Sabouraud at 28° C. for 3 days.

The fungal masses of the strains DSM-7279 and 9472 were lifted off and separately homogenised in 500 ml of an aqueous solution of 0.5% soya peptone, 5% glucose and 0.1% yeast extract. The concentration of microconidia was adjusted to 55 million per ml for each homogenate. To yield 50 to 100% germ tubes each suspension of microconidia was fermented for 1–2 days at 28° C. The cell suspensions were washed with a physiological solution of sodium chloride 5 times by centrifugation (4000 rpm) at 10° C. for 25 minutes for each centrifugation step.

The blastospores of strain DSM-9456 were lifted off by washing with 500 ml of a physiological solution of sodium chloride. The concentration of blastospores in suspension was adjusted to 60 million per ml.

500 ml of each culture in suspension were combined and mixed in a single container. The homogenate was inactivated by adding thiomersal in a ratio of 1:20000 (w/v) directly to the cell suspension. For this purpose 75 mg of thiomersal were added to 1.5 liters of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine after Trichophyton challenge in guinea pigs is shown in tables 11, 12, 13, 14 and FIGS. 3, 4 (Complex III-IV).

Example 5

Cultures of the strains *Trichophyton mentagrophytes* DSM-7279, Trichophyton rubrum DSM-9469, *Trichophyton* rubrum DSM-9470, Trichophyton rubrum DSM-9471, Trichophyton rubrum DSM-9472 and Candida albicans DSM-9456, Candida albicans DSM-9457, Candida albicans DSM-9458, Candida albicans DSM-9459 were used to prepare 1.5 liters of the vaccine. Cultures of strains DSM-7279, 9469, 9470, 9471,9472 were cultivated separately on malt extract agar in 3 Roux flasks for each culture for 20 days at 28° C. Cultures of Candida albicans strains DSM-9456, 9457, 9458, 9459 were cultivated in 1 Roux flask for each culture on agar Sabouraud at 28° C. for 3 days.

The fungal masses of strains DSM-9469, 9470, 9471 and 9472 were lifted off and separately homogenised in 100 ml of a solution of 0.3% fermented hydrolyzed muscle protein, 5% glucose and 0.1% yeast extract. Then the fungal mass of strain DSM-7279 was homogenised in 500 ml of a solution of 0.3% fermented hydrolyzed muscle protein, 5% glucose and 0.1% yeast extract. The concentration of microconidia was adjusted to 60 million per ml for each homogenate. To yield 50 to 100% germ tubes in suspensions of microconidia each dermatophyte culture was fermented for 1 day at 28° C. After cultivation 150 ml of each suspension of Trichophyton rubrum DSM-9469, 9470, 9471, 9472 were mixed in a single container.

The blastospores of strains DSM-9456, 9457, 9458, 9459 were lifted off by washing with 200 ml of a physiological solution of sodium chloride. The concentration of blastospores in each suspension was adjusted to 60 million per ml. 150 ml of each suspension were mixed in a single container.

500 ml of the Trichophyton mentagrophytes DSM-7279 suspension were mixed with 500 ml of the Trichophyton rubrum DSM-9469, 9470, 9471, 9472 mixture suspension and with 500 ml of the Candida albicans DSM-9456, 9457, 9458, 9459 mixture suspension in a single container. The homogenate was inactivated by adding thiomersal in a ratio of 1:12500 (w/v) directly to the cell suspension. For this purpose 80 mg of thiomersal were added to 1 liter of homogenate. The mixture was incubated at room temperature for 1 day. The resulting vaccine was bottled, checked for sterility, safety and immunogenic properties in accordance with accepted methods and kept refrigerated at 4° C. The vaccine prepared in this manner was used to immunise animals by intramuscular injection.

Example 6

Cultures of the strains Trichophyton mentagrophytes DSM-7279, Trichophyton rubrum DSM-9469, Trichophyton rubrum DSM-9471, Trichophyton rubrum DSM-9472 and Candida albicans DSM-9456, Candida albicans DSM-9457 were used to prepare 1.5 liters of the vaccine. Cultures of strains DSM-7279, 9469, 9471, 9472 were cultivated separately on malt extract agar in 4 Roux flasks for each culture for 20 days at 28° C. Cultures of Candida albicans strains DSM-9456, 9457 were cultivated in 1 Roux flask for each culture on agar Sabouraud at 28° C. for 3 days.

The fungal masses of strains DSM-9469, 9471 and 9472 were lifted off and each culture separately homogenised in 200 ml of a solution of 0.3% fermented hydrolyzed muscle protein, 5% glucose and 0.1% yeast extract. The fungal mass of strain DSM-7279 was homogenised in 500 ml of a solution a 0.3% fermented hydrolyzed muscle protein, 5% glucose and 0.1% yeast extract. The concentration of microconidia was adjusted to 60 million per ml of the homogenate for each culture. To yield 50 to 100% germ tubes in suspensions of microconidia each of dermatophyte strains was fermented for 1 day at 28° C. After cultivation 200 ml of Trichophyton rubrum DSM-9469, 9471, 9472 suspensions were mixed in a single container.

The blastospores of strain DSM-9456, 9457 were lifted off by washing with 250 ml of a physiological solution of sodium chloride. The concentration of blastospores in suspension was adjusted to 60 million per ml. 250 ml of the of each culture suspension were combined and mixed in a single container. 500 ml of the Trichophyton mentagrophytes DSM-7279 suspension were mixed with 500 ml of the Trichophyton rubrum DSM-9469, 9471, 9472 mixture suspension and with 500 ml of the suspensions of cultures DSM-9456, 9457 in a single container. The homogenates were inactivated by adding thiomersal in a ratio of 1:25000 (w/v) directly to the cell suspension. For this purpose 60 mg of thiomersal were added to 1.5 liters of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection. The efficacy after Trichophyton challenge is shown in tables 24–27 and FIGS. 11 and 12 and for Candida albicans challenge in table 44.

Example 7

Cultures of the strains Trichophyton mentagrophytes DSM-7279, Trichophyton rubrum DSM-9472 and Candida albicans DSM-9456, Candida albicans DSM-9457 were used to prepare 1.5 liters of the vaccine. Cultures of strains DSM-7279, 9472 were cultivated separately on malt extract agar in 8 Roux flasks for each culture for 20 days at 28° C. Cultures of Candida albicans strains DSM-9456, 9457 were cultivated in 1 Roux flask for each culture on agar Sabouraud at 28° C. for 3 days.

Fungal masses of strain DSM-9472 were lifted off and homogenised in 500 ml of a solution of 0.3% fermented hydrolyzed muscle protein, 5% glucose and 0.1% yeast extract. The fungal mass of strain DSM-7279 was homogenised in 500 ml of a solution of 0.3% fermented hydrolyzed muscle protein, 5% glucose and 0.1% yeast extract. The concentration of microconidia was then adjusted to 50 million per ml of homogenate for each culture. To yield 50 to 100% germ tubes in suspensions of microconidia each strain of dermatophytes was fermented for 2 days at 28° C.

The blastospores of strain DSM-9456, 9457 were lifted off by washing with 250 ml of a physiological solution of sodium chloride. The concentration of blastospores in suspension was adjusted to 60 million per ml. 250 ml of each culture suspension were combined and mixed in a single container.

500 ml of the Trichophyton mentagrophytes DSM-7279 suspension were mixed with 500 ml of the Trichophyton rubrum DSM-9472 suspension and with 500 ml of the suspensions of cultures DSM-9456, 9457 in a single container. The homogenates were inactivated by adding thiomersal in a ratio of 1:12500 (w/v) directly to the cell suspension. For this purpose 120 mg of thiomersal were added to 1.5 liters of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection.

Example 8

Cultures of the strains Trichophyton mentagrophytes DSM-7279, Trichophyton rubrum DSM-9472 and Candida

*albicans* DSM-9456 were used to prepare 1.5 liters of the vaccine. Cultures of strains DSM-7279, 9472 were cultivated separately on malt extract agar in 6 Roux flasks for each culture for 20 days at 28° C. Cultures of *Candida albicans* strain DSM-9456 were cultivated in 2 Roux flasks on agar Sabouraud at 28° C. for 3 days.

Fungal masses of strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml for each homogenate. To yield 50 to 100% germ tubes both suspensions of microconidia were fermented for 2 days at 28° C. 500 ml of the *Trichophyton mentagrophytes* DSM-7279 suspension were mixed with 500 ml of the *Trichophyton rubrum* DSM-9472 suspension in a single container. The homogenates were inactivated by adding thiomersal in a ratio of 1:25000 (w/v) directly to the cell suspension. For this purpose 40 mg of thiomersal were added to 1 liter of homogenate. The mixture was incubated at room temperature for 2 days.

The culture of strain DSM-9456 was harvested and homogenised in 5000 ml medium RPMI No. 1640 with L-glutamine (Serva). The concentration of the blastospores was adjusted to 20 million per ml. 5000 ml of this cell suspension was incubated in cell culture flasks containing medium No. 1640 in a $CO_2$ atmosphere of 5% at 36–38° C. After 4 hours incubation period 50% to 100% of the blastospores commonly displayed germ tubes and a swollen condition. The blastospores were harvested and washed 3 times by centrifugation (4000 rpm) at 4–10° C. for 25 minutes for each centrifugation step. The concentration of the cells was adjusted to 60 million per ml. The homogenates were inactivated by adding thiomersal in a ratio of 1:20000 (w/v) directly to the cell suspension. For this purpose 80 mg of thiomersal were added to 1 liter of homogenate. The mixture was incubated at room temperature for 2 days. 750 ml of the suspension of culture of DSM-9456 were combined and mixed with 750 ml of the mixture of DSM-7279 and 9472 culture suspension. The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine in mice after *Candida albicans* challenge is shown in tables 1, 2, 5 (Complex 1-I, 3-I) and after *Trichophyton rubrum* challenge in guinea pigs in tables 7, 8 and FIG. 1 (Complex I-I).

Example 9

Cultures of the strains *Trichophyton mentagrophytes* DSM-7279, *Trichophyton rubrum* DSM-9469, *Trichophyton rubrum* DSM-9470, *Trichophyton rubrum* DSM-9471, *Trichophyton rubrum* DSM-9472 and *Candida albicans* DSM-9456, *Candida albicans* DSM-9457, *Candida albicans* DSM-9458, *Candida albicans* DSM-9459 were used to prepare 1.5 liters of the vaccine. Cultures of strains DSM-7279, 9469, 9470, 9471, 9472 were cultivated separately on malt extract agar in 3 Roux flasks for each culture for 20 days at 28° C. Cultures of *Candida albicans* strains DSM-9456, 9457, 9458, 9459 were cultivated in 1 Roux flask for each culture on agar Sabouraud at 28° C. for 3 days.

Fungal masses of strains DSM-9469, 9470, 9471 and 9472 were lifted off and separately homogenised in 100 ml of a solution of 0.3% fermented hydrolyzed muscle protein, 5% glucose and 0.1% yeast extract. The fungal mass of strain DSM-7279 was homogenised in 500 ml of a solution of 0.3% fermented hydrolyzed muscle protein, 5% glucose and 0.1% yeast extract. The concentration of microconidia was adjusted to 60 million per ml for each homogenate. To yield 50 to 100% germ tubes in suspensions of microconidia each dermatophyte culture was fermented for 1 day at 28° C. After cultivation 150 ml of each suspension of *Trichophyton rubrum* DSM 9469, 9470, 9471, 9472 were mixed in a single container. The homogenates were inactivated by adding thiomersal in a ratio of 1:16000 (w/v) directly to the cell suspensions. For this purpose 62.5 mg of thiomersal were added to 1 liter of homogenate. The mixture was incubated at room temperature for 2 days.

The culture of strain DSM-9456, 9457, 9458, 9459 were harvested and homogenised in medium No. 1640 (Serva). The concentration of the blastospores was adjusted to 20 million per ml. 1500 ml of cell suspensions of each culture were incubated in cell culture flasks containing medium No. 1640 in a $CO_2$ atmosphere of 6% at 36–38° C. After 3 hours incubation period 50% to 100% of the blastospores commonly displayed germ tubes and a swollen condition. The blastospores were harvested and washed 3 times by centrifugation (4000 rpm) at 4–10° C. for 25 minutes for each centrifugation step. The concentration of the cells was adjusted to 60 million per ml. The homogenate was inactivated by adding thiomersal in a ratio of 1:25000 (w/v) directly to the cell suspension. For this purpose 40 mg of thiomersal were added to 1 liter of homogenate. The mixture was incubated at room temperature for 1 day. 150 ml of each suspension of the cultures of DSM-9456, 9457, 9458, 9459 were combined and mixed in a single container.

500 ml of the mixture suspensions of cultures DSM-9469, 9470, 9471, 9472 were mixed with 500 ml suspension culture DSM-7279 and 500 ml mixture suspensions of cultures DSM-9456, 9457, 9458, 9459.

The resulting vaccine was bottled, checked for sterility, safety and immunogenic properties in accordance with accepted methods and kept refrigerated at 4° C. The vaccine prepared in this manner was used to immunise animals by intramuscular injection.

Example 10

Cultures of the strains *Trichophyton mentagrophytes* DSM-7279, *Trichophyton rubrum* DSM-9469, *Trichophyton rubrum* DSM-9471, *Trichophyton rubrum* DSM-9472 and *Candida albicans* DSM-9456, *Candida albicans* DSM-9457 were used to prepare 1.5 liters of the vaccine. Cultures of strains DSM-7279, 9469, 9471, 9472 were cultivated separately on malt extract agar in 4 Roux flasks for each culture for 20 days at 28° C. Cultures of *Candida albicans* strains DSM-9456, 9457 were cultivated in 1 Roux flask for each culture on agar Sabouraud at 28° C. for 3 days.

Fungal masses of strains DSM-9469, 9471 and 9472 were lifted off, combined and homogenised in 100 ml of an aqueous solution of 0.3% fermented hydrolyzed muscle protein, 5% glucose and 0.1% yeast extract. The fungal masses of strain DSM-7279 and the mixture of strains DSM-9469, 9471 and 9472 were lifted off and each homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the mixture of *Trichophyton rubrum* DSM-9469, 9471, 9472 suspension in a single container. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

The cultures of strains DSM-9456, 9457 were harvested and homogenised in medium No. 1640 (Serva). The concentration of the blastospores was adjusted to 20 million per ml. 1500 ml of cell suspensions of each cultures were incubated in cell culture flasks containing medium No. 1640 in a $CO_2$ atmosphere of 5% at 36–38° C. After 4 hours incubation period 50 to 100% of the blastospores commonly displayed germ tubes and a swollen condition. The blastospores were harvested and washed 3 times by centrifugation (5000 rpm) at 4–10° C. for 20 minutes for each centrifugation step. The concentration of the cells was adjusted to 50 million per ml. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 1 day. 150 ml of each suspension of cultures DSM-9456, 9457 were combined and mixed in a single container.

500 ml of the mixture suspensions of culture DSM-9469, 9471, 9472 were mixed with 500 ml suspension culture DSM-7279 and with 500 ml mixture suspensions of cultures DSM-9456, 9457.

The resulting vaccine was bottled, checked for sterility, safety and immunogenic properties in accordance with accepted methods and kept refrigerated at 4° C. The vaccine prepared in this manner was used to immunise animals by intramuscular injection.

Example 11

Cultures of the strains *Trichophyton mentagrophytes* DSM-7279, *Trichophyton rubrum* DSM-9472 and *Candida albicans* DSM-9456, *Candida albicans* DSM-9457, *Candida albicans* DSM-9459 were used to prepare 1.5 liters of the vaccine. Cultures of strains DSM-7279, 9472 were cultivated separately on malt extract agar in 6 Roux flasks for each culture for 20 days at 28° C. Cultures of *Candida albicans* strains DSM-9456, 9457, 9459 were cultivated in 1 Roux flask each on agar Sabouraud at 28° C. for 3 days.

The fungal masses of strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1 day at 28° C. 500 ml of the *Trichophyton mentagrophytes* DSM-7279 suspension were mixed with 500 ml of the *Trichophyton rubrum* DSM-9472 suspension in a single container. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

The cultures of *Candida albicans* strains DSM-9456, 9457, 9459 were harvested and separately homogenised in medium No. 1640 (Serva). The concentration of the blastospores was adjusted to 10 million per ml. 2000 ml of each cell suspension was incubated separately in cell culture flasks or in Petri dishes containing medium No. 1640 in a $CO_2$ atmosphere of 6% at 38° C. After 3 hours incubation period 50–100% of the blastospores commonly displayed germ tubes or a swollen condition. The blastospores were harvested and washed 3 times by centrifugation (5000 rpm) at 4–10° C. for 25 minutes for each centrifugation step. The concentration of the cells was adjusted to 20 million per ml. The cell suspensions of each strain were mixed using equal volumes. The mixed suspension was inactivated with thiomersal in a ratio of 1:25000 (w/v).

500 ml of this suspension was mixed with 1000 ml suspension of microconidiae. The resulting vaccine was bottled, checked for sterility, safety and immunogenic properties in accordance with accepted methods and kept refrigerated at 4° C. Vaccine prepared in this manner was used to immunise animals by intramuscular injection.

Example 12

Cultures of the strains *Trichophyton mentagrophytes* DSM-7279, *Trichophyton rubrum* DSM-9472 and *Candida albicans* DSM-9456 were used to prepare 1.5 liters of the vaccine. Cultures of strains DSM-7279, 9472 were cultivated separately on malt extract agar in 6 Roux flasks for each culture for 20 days at 28° C. Cultures of Candida albicans strain DSM-9456 were cultivated in 2 Roux flasks on agar Sabouraud at 28° C. for 3 days.

The fungal masses of strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 2 days at 28° C. 500 ml of the *Trichophyton mentagrophytes* DSM-7279 suspension were mixed with 500 ml of the *Trichophyton rubrum* DSM-9472 suspension in a single container.

The blastospores of strain DSM-9456 were lifted off by washing with 500 ml of destined water. The concentration of blastospores in suspension was adjusted to 56 million per ml.

500 ml of this suspension were mixed with the suspension of microconidiae. The homogenate was inactivated by adding thiomersal in a ratio of 1:20000 (w/v) directly to the cell suspension. For this purpose 50 mg thiomersal were added to 1 liter of homogenate. This mixture was incubated at room temperature for 2 days.

After the inactivating process the cell suspension was treated with $H_2O_2$. A substance containing $H_2O_2$, for example Urea-hydrogen peroxide, was added to a cell suspension to yield a final concentration of 3% of $H_2O_2$. This cell suspension was stirred for 24 hours. Treated cells were washed 5 times for 30 minutes with destined water by centrifugation (4000 rpm). The final concentration of cells was adjusted to 60 million per ml.

The resulting vaccine was bottled, checked for sterility, safety and immunogenic properties in accordance with accepted methods and kept refrigerated at 4° C. Vaccine prepared in this manner was used to immunise animals by intramuscular injection. The efficacy of the vaccine after *Candida albicans* challenge in mice is shown in table 6 (Complex 4–1), and after Trichophyton challenge in guinea pigs in tables 11, 12, 13, 14 and FIGS. 3, 4 (Complex III-V).

Example 13

Cultures of the strains *Trichophyton mentagrophytes* DSM-7279, *Trichophyton rubrum* DSM-9469, *Trichophyton rubrum* DSM-9470, *Trichophyton rubrum* DSM-9471, *Trichophyton rubrum* DSM-9472 and *Candida albicans* DSM- 9456, *Candida albicans* DSM-9457, *Candida albicans* DSM-9458, *Candida albicans* DSM-9459 were used to prepare 1.5 liters of the vaccine. Cultures of strains DSM-7279, 9469, 9470, 9471, 9472 were cultivated separately on malt extract agar in 3 Roux flasks for each culture for 20 days at 28° C. Cultures of Candida albicans strains DSM-9456, 9457, 9458, 9459 were cultivated in 1 Roux flask for each culture on agar Sabouraud at 28° C. for 3 days.

The fungal masses of strains DSM-9469, 9470, 9471 and 9472 were lifted off, combined and homogenised in 100 ml of an aqueous solution of 0.3% fermented hydrolyzed muscle protein, 5% glucose and 0.1% yeast extract. The fungal masses of strain DSM-7279 and the mixture of strains DSM-9469, 9470, 9471 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the mixture of *Trichophyton rubrum* DSM-9469, 9470, 9471, 9472 suspension in a single container.

The blastospores of strain DSM-9456, 9457, 9458, 9459 were lifted off by washing with 200 ml of destined water. The concentration of blastospores in suspension was adjusted to 60 million per ml. 150 ml of each suspension were mixed.

500 ml of the resulting suspension were mixed with the suspension of microconidiae. The homogenate was inactivated by adding thiomersal directly to the cell suspension in a ratio of 1:20000 (w/v). For this purpose 50 mg thiomersal were added to 1 liter of homogenate. This mixture was incubated at room temperature for 2 days. Following inactivation the cell suspension was treated with sodium permanganate in a concentration of 1:10000 (w/v) for 16 hours while stirring. Treated cells were washed 5 times with destined water by centrifugation (4000 rpm) for 25 minutes for each centrifugation step. The final concentration of cells was adjusted to 40 million per ml.

The resulting vaccine was bottled, checked for sterility, safety and immunogenic properties in accordance with accepted methods and kept refrigerated at 4° C. The vaccine prepared in this manner was used to immunise animals by intramuscular injection.

Example 14

Cultures of the strains *Trichophyton mentagrophytes* DSM-7279, *Trichophyton rubrum* DSM-9469, *Trichophyton rubrum* DSM-9471, *Trichophyton rubrum* DSM-9472 and *Candida albicans* DSM-9456, *Candida albicans* DSM-9457 were used to prepare 1.5 liters of the vaccine. Cultures of strains DSM-7279, 9469, 9471, 9472 were cultivated separately on malt extract agar in 4 Roux flasks for each culture for 20 days at 28° C. Cultures of *Candida albicans* strains DSM-9456, 9457 were cultivated in 1 Roux flask for each culture on agar Sabouraud at 28° C. for 3 days.

The fungal masses of strains DSM-9469, 9471 and 9472 were lifted off, combined and homogenised in 100 ml of an aqueous solution of 0.3% fermented hydrolyzed muscle protein, 5% glucose and 0.1% yeast extract. The fungal masses of strain DSM-7279 and the mixture of strains DSM-9469, 9471 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the mixture of *Trichophyton rubrum* DSM-9469, 9471, 9472 suspension in a single container.

The blastospores of strain DSM-9456 and 9457 were lifted off by washing with 200 ml of a physiological sodium chloride solution. The concentration of blastospores in suspension was adjusted to 60 million per ml. 250 ml of each suspension were mixed.

500 ml of the resulting suspension was mixed with a suspension of microconidiae. The homogenate was inactivated by adding thiomersal directly to the cell suspension in a ratio of 1:20000 (w/v). For this purpose 50 mg thiomersal were added to 1 liter of homogenate. This mixture was incubated at room temperature for 2 days.

After the inactivating process the cell suspension was treated with $H_2O_2$. hydrogen peroxide tablets (Wasserstoff-Peroxid Tabletten WDT) were added to cell suspensions to yield a final concentration of 1% of $H_2O_2$. The cell suspension was stirred for 24 hours. Treated cells were washed 5 times for 30 minutes with destilled water by centrifugation (4000 rpm). The final concentration of the cells was adjusted to 50 million per ml.

The resulting vaccine was bottled, checked for sterility, safety and immunogenic properties in accordance with accepted methods and kept refrigerated at 4° C. The vaccine prepared in this manner was used to immunise animals by intramuscular injection.

Example 15

Cultures of the strains *Trichophyton mentagrophytes* DSM-7279, *Trichophyton rubrum* DSM-9472 and *Candida albicans* DSM-9456, *Candida albicans* DSM-9457, *Candida albicans* DSM-9459 were used to prepare 1.5 liters of the vaccine. Cultures of strains DSM-7279, 9472 were cultivated separately on malt extract agar in 6 Roux flasks for each culture for 20 days at 28° C. Cultures of *Candida albicans* strains DSM-9456, 9457, 9459 were cultivated in 1 Roux flask for each culture on agar Sabouraud at 28° C. for 3 days.

The fungal masses of strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the *Trichophyton rubrum* DSM 9472 suspension in a single container.

The blastospores of strain DSM-9456, 9457, 9459 were lifted off by washing with 200 ml of a physiological sodium chloride solution. The concentration of blastospores in suspension was adjusted to 60 million per ml. 250 ml of each suspension were mixed.

500 ml of the resulting suspension were mixed with the suspension of microconidiae. The homogenate was inactivated by adding thiomersal directly to the cell suspension in a ratio of 1:20000 (w/v). For this purpose 50 mg thiomersal were added to 1 liter of homogenate. This mixture was incubated at room temperature for 2 days.

Following the inactivation the cell suspension was treated with sodium permanganate in a concentration of 1:20000

(w/v) for 36 hours while stirring. Treated cells were washed 5 times with destilled water by centrifugation (4000 rpm) for 25 minutes for each centrifugation step.

The final concentration of the cells was adjusted to 60 million per ml. The resulting vaccine was bottled, checked for sterility, safety and immunogenic properties in accordance with accepted methods and kept refrigerated at 4° C. The vaccine prepared in this manner was used to immunise animals by intramuscular injection.

Example 16

Cultures of the strains *Trichophyton mentagrophytes* DSM-7279, *Trichophyton rubrum* DSM-9472 and *Candida albicans* DSM-9456 were used to prepare 1.5 liters of the vaccine. Cultures of strains DSM-7279, 9472 were cultivated separately on malt extract agar in 6 Roux flasks for each culture for 20 days at 28° C. Cultures of *Candida albicans* strain DSM-9456 were cultivated in 2 Roux flasks on agar Sabouraud at 28° C. for 3 days.

The fungal masses of strains DSM-7279 and 9472 were lifted off and separately homogenised in 200 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the *Trichophyton rubrum* DSM-9472 suspension in a single container. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

Following inactivation the cell suspension was treated with $H_2O_2$. A substance containing $H_2O_2$, for example Urea-hydrogen peroxide, was added to the cell suspension to yield a final concentration of 3% of $H_2O_2$. This cell suspension was stirred for 24 hours. Treated cells were washed 5 times for 30 minutes with destilled water by centrifugation (4000 rpm). The final concentration of cells was adjusted to 40 million per ml.

The culture of strain DSM-9456 was harvested and homogenised in medium No. 1640 (Serva). The concentration of the blastospores was adjusted to 20 million per ml. 2000 ml of this cell suspension were incubated in cell culture flasks of medium No. 1640 in a $CO_2$ atmosphere of 5% at 36–38° C. After 3 hours incubation period 50% to 100% of the blastospores commonly displayed germ tubes or a swollen condition. The blastospores were harvested and washed for 3 times by centrifugation (4000 rpm) at 4–10° C. for 25 minutes for each centrifugation step. The concentration of the cells was adjusted to 40 million per ml. The suspension was inactivated using thiomersal in a ratio of 1:25000 (w/v).

Following the inactivation the cell suspension was treated with $H_2O_2$. A substance containing $H_2O_2$, for example Urea-hydrogen peroxide (Wasserstoff-Peroxid Harpstoff zur Synthese $CN_2H_4O\ H_2O_2$), was added to cell suspensions to yield a final concentration of 3% of $H_2O_2$. The cell suspension was stirred for 24 hours. Treated cells were washed 5 times for 30 minutes with destilled water by centrifugation (4000 rpm). The final concentration of cells was adjusted to 120 million per ml. 500 ml of this suspension were mixed with 1000 ml suspension of microconidiae.

Figure 1:
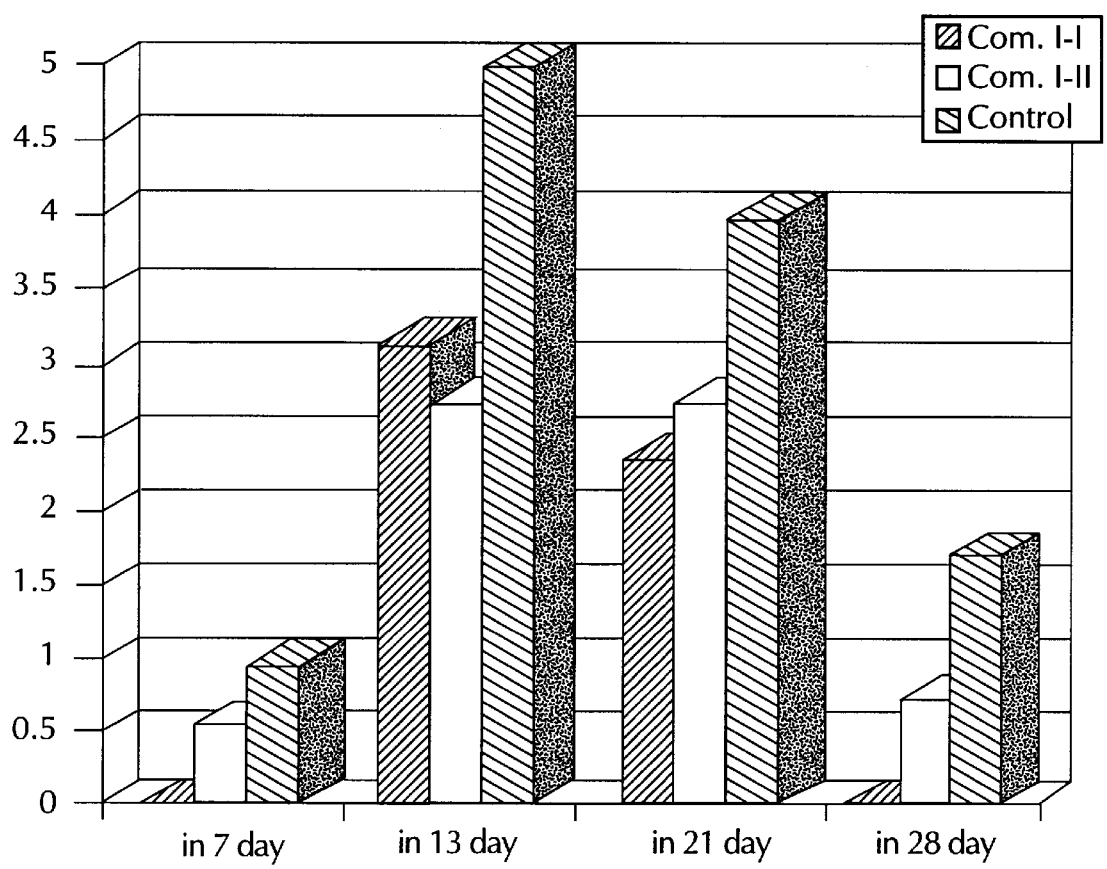
FIG. 1. The dynamics of clinical symptoms of *Trichophyton rubrum* infections in guinea pigs (1st experiment, Complex I-I and I-II). Compared with the severity score values of the control group the efficacy of Complex I-I was 100%, 36.0%, 40.0% and 100%, Complex I-II 40.0%, 44.0%, 30.0% and 55.6% after 7, 13, 21 and 28 days respectively.
Figure 2:
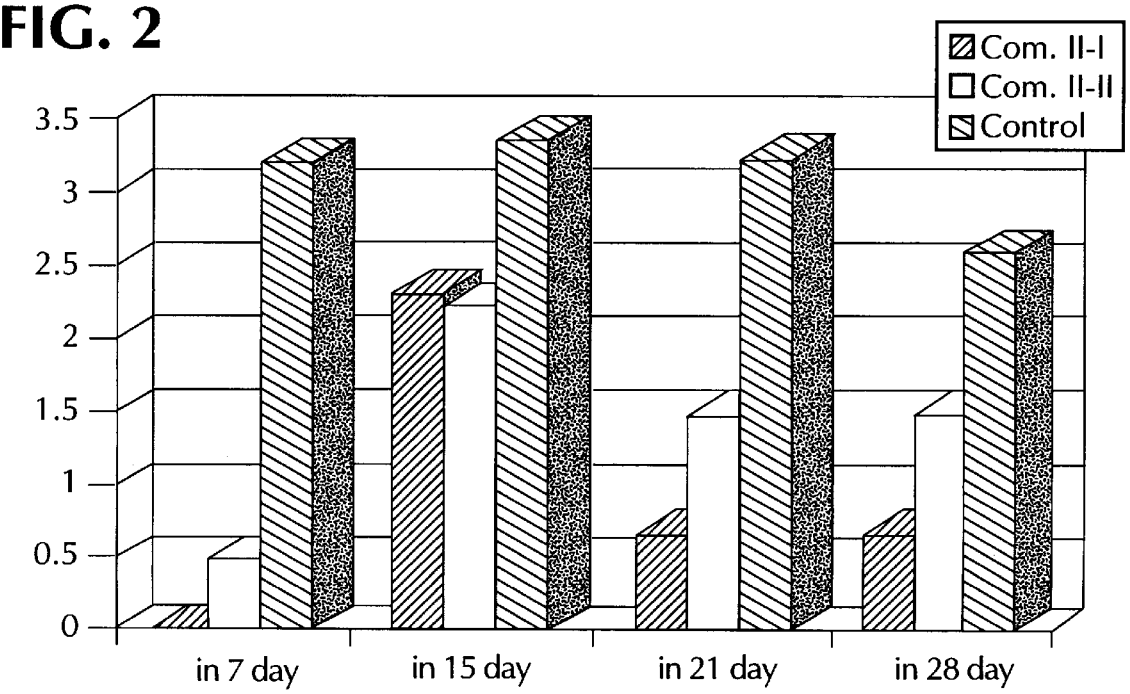
FIG. 2. The dynamics of clinical symptoms of *Trichophyton rubrum* infections in guinea pigs (2nd experiment, Complex II-I and II-II). Compared with the severity score values of the control group the efficacy of Complex II-I was 100%, 32.4%, 79.4% and 74.6%, Complex II-II 84.4%, 33.8%, 53.1% and 42.3% after 7, 15, 21 and 28 days respectively.
Figure 3:
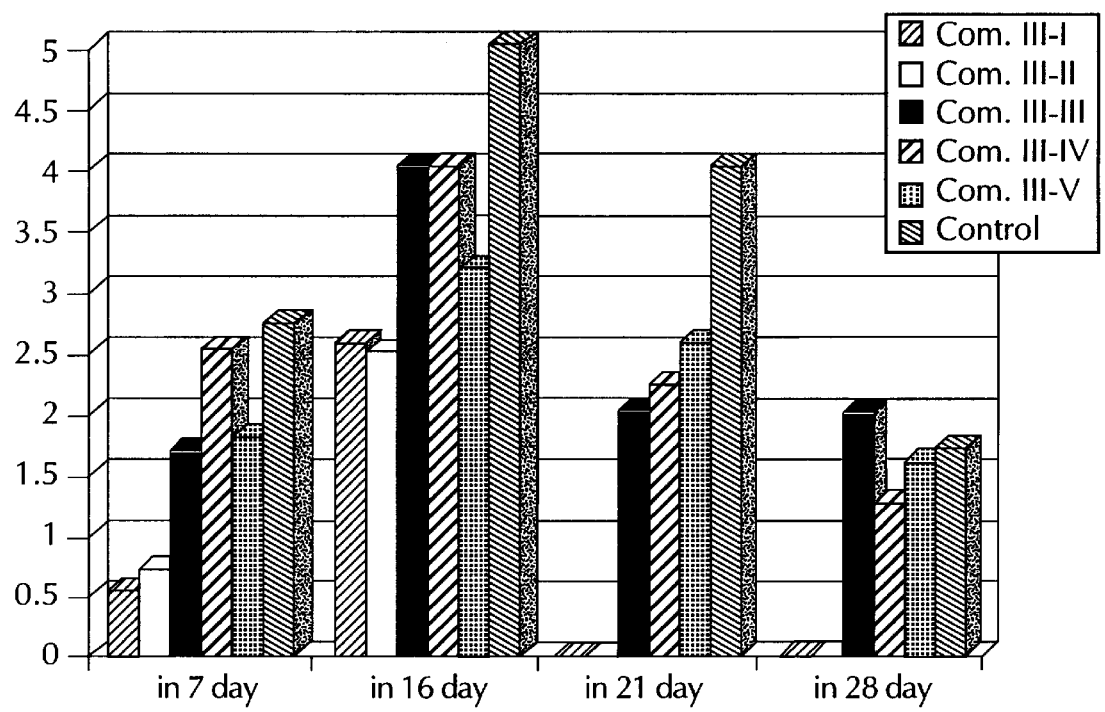
FIG. 3. The dynamics of clinical symptoms of *Trichophyton rubrum* infections in guinea pigs (3rd experiment, Complex III-I, III-II, III-III, III-IV and III-V).

The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine after *Candida albicans* challenge in mice is shown in tables 1, 2, 3, 4, 5 (Complex 1-II, 2-I, 3-II) and after *Trichophyton rubrum* challenge in guinea pigs in tables 7, 8 and FIG. 1 (Complex I-II).

Example 17

Cultures of the strains *Trichophyton mentagrophytes* DSM-7279, *Trichophyton rubrum* DSM-9469, *Trichophyton rubrum* DSM-9470, *Trichophyton rubrum* DSM-9471, *Trichophyton rubrum* DSM-9472 and *Candida albicans* DSM-9456, *Candida albicans* DSM-9457, *Candida albicans* DSM-9458, *Candida albicans* DSM-9459 were used to prepare 1.5 liters of the vaccine. Cultures of strains DSM-7279, 9469, 9470, 9471, 9472 were cultivated separately on malt extract agar in 3 Roux flasks for each culture for 20 days at 28° C. Cultures of *Candida albicans* strains DSM-9456, 9457, 9458, 9459 were cultivated in 1 Roux flask for each culture on agar Sabouraud at 28° C. for 3 days.

The fungal masses of strains DSM-9469, 9470, 9471 and 9472 were lifted off, combined and homogenised in 100 ml of an aqueous solution of 0.3% fermented hydrolyzed muscle protein, 5% glucose and 0.1% yeast extract. The fungal masses of strain DSM-7279 and the mixture of strains DSM-9469, 9470, 9471 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the mixture of *Trichophyton rubrum* DSM-9469, 9470, 9471, 9472 suspension in a single container. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

Following the inactivation the cell suspension was treated with sodium permanganate in a concentration of 1:30000 (w/v) for 24 hours while stirring. Treated cells were washed 5 times with destilled water by centrifugation (4000 rpm) for 25 minutes for each centrifugation step. The final concentration of the cells was adjusted to 60 million per ml.

The cultures of strains DSM-9456, 9457, 9458, 9459 were harvested and separately homogenised in medium No. 1640. The concentration of the blastospores was adjusted to 20 million per ml. 130 ml of the cell suspensions were incubated separately in cell culture flasks containing medium No. 1640 in a $CO_2$ atmosphere of 5% at 36–38° C. After 3 hours incubation period 50% to 100% of the blastospores commonly displayed germ tubes or a swollen condition. The blastospores were harvested and washed for 2–3 times by centrifugation (4000 rpm) at 4–10° C. for 25 minutes for each centrifugation step.

The concentration of the cells was adjusted to 40 million per ml. The suspension was inactivated using thiomersal in a ratio of 1:25000 (w/v). Following the inactivation the cell suspension was treated with $H_2O_2$. Hydrogen peroxide tablets (Wasserstoff-Peroxid Tabletten WDT) were added to cell suspensions to yield a final concentration of 3% of $H_2O_2$. The cell suspension was stirred for 24 hours. Treated cells were washed 5 times for 30 minutes with destined water by centrifugation (4000 rpm). The final concentration of the cells was adjusted to 60 million per ml.

500 ml of this suspension were mixed with 1000 ml suspension of 20 microconidiae. The resulting vaccine was bottled, checked for sterility, safety and immunogenic properties in accordance with accepted methods and kept refrigerated at 4° C. The vaccine prepared in this manner was used to immunise animals by intramuscular injection.

Example 18

Cultures of the strains *Trichophyton mentagrophytes* DSM-7279, *Trichophyton rubrum* DSM-9469, *Trichophyton rubrum* DSM-9471, *Trichophyton rubrum* DSM-9472 and *Candida albicans* DSM-9456, *Candida albicans* DSM-9457 were used to prepare 1.5 liters of the vaccine. Cultures of strains DSM-7279, 9469, 9471, 9472 were cultivated separately on malt extract agar in 4 Roux flasks for each culture for 20 days at 28° C. Cultures of *Candida albicans* strains DSM-9456, 9457 were cultivated in 1 Roux flask for each culture on agar Sabouraud at 28° C. for 3 days.

The fungal masses of strains DSM-9469, 9471 and 9472 were lifted off, combined and homogenised in 100 ml of an aqueous solution of 0.3% fermented hydrolyzed muscle protein, 5% glucose and 0.1% yeast extract. The fungal mass of strain DSM-7279 and the mixture of strains DSM-9469, 9471 and 9472 were lifted off, separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the mixture of *Trichophyton rubrum* DSM-9469, 9471, 9472 suspension in a single container. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

Following the inactivation the cell suspension was treated with $H_2O_2$. Hydrogen peroxide tablets (Wasserstoff-Peroxid Tabletten WDT) were added to the cell suspension to yield a final concentration of 2% of $H_2O_2$. The cell suspension was stirred for 36 hours. Treated cells were washed 5 times for 25 minutes with destined water by centrifugation (4000 rpm). The final concentration of cells was adjusted to 60 million per ml.

The cultures of strains DSM-9456, 9457 were harvested and separately homogenised in medium No. 1640 (Serva). The concentration of the blastospores was adjusted to 10–20 million per ml. 130 ml of the cell suspensions were incubated separately in cell culture flasks containing medium No. 1640 in a $CO_2$ atmosphere of 6% at 36–38° C. After 3 hours incubation period 50% to 100% of the blastospores commonly displayed germ tubes or a swollen condition. The blastospores were harvested and washed for 3 times by centrifugation (4000 rpm) at 4–10° C. for 25 minutes for each centrifugation step. The concentration of the cells was adjusted to 40 million per ml. The suspension was inactivated using thiomersal in a ratio of 1:25000 (w/v). Following the inactivation the cell suspension was treated with $H_2O_2$. Hydrogen peroxide tablets (Wasserstoff-Peroxid Tabletten WDT) were added to the cell suspension to yield a final concentration of 3% of $H_2O_2$. This cell suspension was stirred for 24 hours. Treated cells were washed 5 times for 30 minutes with destined water by centrifugation (4000 rpm). The final concentration of cells was adjusted to 60 million per ml.

500 ml of this suspension were mixed with 1000 ml suspension of microconidiae. The resulting vaccine was bottled, checked for sterility, safety and immunogenic properties in accordance with accepted methods and kept refrigerated at 4° C. The vaccine prepared in this manner was used to immunise animals by intramuscular injection.

Example 19

Cultures of the strains *Trichophyton mentagrophytes* DSM-7279, *Trichophyton rubrum* DSM-9472 and *Candida albicans* DSM-9456, *Candida albicans* DSM-9457, *Candida albicans* DSM-9459 were used to prepare 1.5 liters of the vaccine. Cultures of strains DSM-7279, 9472 were cultivated separately on malt extract agar in 6 Roux flasks for each culture for 20 days at 28° C. Cultures of *Candida albicans* strains DSM-9456, 9457, 9459 were cultivated in 1 Roux flask for each culture on agar Sabouraud at 28° C. for 3 days.

The fungal masses of strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. To yield 50 to 100% germ tubes both suspensions of microconidia were fermented for 1–2 days at 28° C. 500 ml of the *Trichophyton mentagrophytes* DSM-7279 suspension were mixed with 500 ml of the *Trichophyton rubrum* DSM-9472 suspension in a single container. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

Following the inactivation the cell suspension was treated with sodium permanganate in a concentration of 1:30000 (w/v) for 24 hours while stirring. Treated cells were washed 5 times with destilled water by centrifugation (4000 rpm) for 25 minutes for each centrifugation step. The final concentration of cells was adjusted to 40 million per ml. The cultures of *Candida albicans* strains DSM-9456, 9457, 9459 were harvested and separately homogenised in medium No. 1640 (Serva). The concentration of the blastospores was adjusted to 20 million per ml. 130 ml of each cell suspension were incubated separately in cell culture flasks containing medium No. 1640 in a $CO_2$ atmosphere of 6% at 36–38° C. After 4 hours incubation period 50% to 100% of the blastospores commonly displayed germ tubes or a swollen condition. The blastospores were harvested and washed for 3 times by centrifugation (4000 rpm) at 4–10° C. for 30 minutes for each centrifugation step. The concentration of the cells was adjusted to 60 million per ml. The cell suspensions of each strain were mixed using equal volumes. The mixed suspension was inactivated using thiomersal in a ratio of 1:11000 (w/v).

Following the inactivation the cell suspension was treated with sodium permanganate in a concentration of 1:20000 (w/v) for 24 hours while stirring. Treated cells were washed 5 times with destined water by centrifugation (4000 rpm) for 25 minutes for each centrifugation step. The final concentration of the cells was adjusted to 60 million per ml.

500 ml of this suspension were mixed with 1000 ml suspension of microconidiae. The resulting vaccine was bottled, checked for sterility, safety and immunogenic properties in accordance with accepted methods and kept refrigerated at 4° C. The vaccine prepared in this manner was used to immunise animals by intramuscular injection. The efficacy after Trichophyton challenge is shown in tables 24–27 and FIGS. 11 and 12 and after *Candida albicans* challenge in table 44 (Complex VI-VI).

Example 20

Cultures of the strains *Trichophyton mentagrophytes* DSM-7279, *Trichophyton rubrum* DSM-9472 and *Candida albicans* DSM-9456 were used to prepare 1.5 liters of the vaccine. *Trichophyton mentagrophytes* DSM-7279 and *Trichophyton rubrum* DSM-9472 were cultivated separately on malt extract agar in 6 Roux flasks for each culture for 20 days at 28° C. The *Candida albicans* DSM-9456 was cultivated in 2 Roux flasks on agar Sabouraud at 28° C. for 3 days.

The fungal masses of the strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. 500 ml of each suspension were mixed in a single container. The blastospores of strain DSM-9456 were lifted off by washing with 500 ml of destined water. The concentration of blastospores in suspension was adjusted to 60 million per ml.

500 ml of this suspension were mixed with the suspension of microconidiae. The homogen rate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine after *Trichophyton rubrum* challenge in guinea pigs is shown in tables 9, 10 and FIG. 2 (Complex II-II).

Example 21

Cultures of the strains *Trichophyton mentagrophytes* DSM-7279, *Trichophyton rubrum* DSM-9469, *Trichophyton rubrum* DSM-9470, *Trichophyton rubrum* DSM-9471, *Trichophyton rubrum* DSM-9472 and *Candida albicans* DSM-9456, *Candida albicans* DSM-9457, *Candida albicans* DSM-9458, *Candida albicans* DSM-9459 were used to prepare 1.5 liters of the vaccine. Cultures of strains DSM-7279, 9469, 9470, 9471, 9472 were cultivated separately on malt extract agar in 3 Roux flasks for each culture for 20 days at 28° C. Cultures of Candida albicans strains DSM-9456, 9457, 9458, 9459 were cultivated in 1 Roux flask for each culture on agar Sabouraud at 28° C. for 3 days.

The fungal masses of strains DSM-9469, 9470, 9471 and 9472 were lifted off, combined and homogenised in 100 ml of an aqueous solution of 3% fermented hydrolyzed muscle protein, 5% glucose and 1% yeast extract. The fungal masses of strain DSM-7279 and the mixture of strains DSM-9469, 9470, 9471 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. 500 ml of the *Trichophyton mentagrophytes* DSM-7279 suspension were mixed with 500 ml of the *Trichophyton rubrum* DSM-9469, 9470, 9471, 9472 mixture suspension in a single container.

The blastospores of strain DSM-9456, 9457, 9458, 9459 were lifted off by washing with 200 ml of destilled water. The concentration of blastospores in suspension was adjusted to 60 million per ml. 150 ml of each suspension were mixed.

500 ml of the resulting suspension were taken and mixed with the suspension of microconidiae. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

The resulting vaccine was bottled, checked for sterility, safety and immunogenic properties in accordance with accepted methods and kept refrigerated at 4° C. The vaccine prepared in this manner was used to immunise animals by intramuscular injection.

Example 22

Cultures of the strains *Trichophyton mentagrophytes* DSM-7279, *Trichophyton rubrum* DSM-9469, *Trichophyton rubrum* DSM-9471, *Trichophyton rubrum* DSM-9472 and *Candida albicans* DSM-9456, *Candida albicans* DSM-9457 were used to prepare 1.5 liters of the vaccine. Cultures of strains DSM-7279, 9469, 9471, 9472 were cultivated separately on malt extract agar in 4 Roux flasks for each culture for 20 days at 28° C. Cultures of *Candida albicans* strains DSM-9456, 9457 were cultivated in 1 Roux flask for each culture on agar Sabouraud at 28° C. for 3 days.

The fungal masses of strains DSM-9469, 9471 and 9472 were lifted off, combined and homogenised in 100 ml of an aqueous solution of 0.3% fermented hydrolyzed muscle protein, 5% glucose and 0.1% yeast extract. The fungal masses of strain DSM-7279 and the mixture of strains DSM-9469, 9471 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. 500 ml of the *Trichophyton mentagrophytes* DSM-7279 suspension were mixed with 500 ml of the *Trichophyton rubrum* DSM-9469, 9471, 9472 mixture suspension in a single container.

The blastospores of strain DSM-9456, 9457 were lifted off by washing with 200 ml of destilled water. The concentration of blastospores in suspension was adjusted to 60 million per ml. 250 ml of each suspension were mixed.

500 ml of the resulting suspension were mixed with the suspension of microconidiae. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days. The resulting vaccine was bottled, checked for sterility, safety and immunogenic properties in accordance with accepted methods and kept refrigerated at 4° C. The vaccine prepared in this manner was used to immunise animals by intramuscular injection. The efficacy of the vaccine after Trichophyton challenge in guinea pigs is shown in tables 24–27 and FIGS. 11 and 12 and after *Candida albicans* challenge in mice in table 44 (Complex VI-I).

Example 23

Cultures of the strains *Trichophyton mentagrophytes* DSM-7279, *Trichophyton rubrum* DSM-9472 and *Candida albicans* DSM-9456, *Candida albicans* DSM-9457, *Candida albicans* DSM-9459 were used to prepare 1.5 liters of the vaccine. Cultures of strains DSM-7279, 9472 were cultivated separately on malt extract agar in 6 Roux flasks for each culture for 20 days at 28° C. Cultures of *Candida albicans* strains DSM-9456, 9457, 9459 were cultivated in 1 Roux flask for each culture on agar Sabouraud at 28° C. for 3 days.

The fungal masses of strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. 500 ml of the *Trichophyton mentagrophytes* DSM-7279 suspension were mixed with 500 ml of the *Trichophyton rubrum* DSM-9472 suspension in a single container.

The blastospores of strain DSM-9456, 9457, 9459 were lifted off by washing with 200 ml of destined water. The concentration of blastospores in suspension was adjusted to 60 million per ml. 250 ml of each suspension were mixed.

500 ml of the resulting suspension were mixed with the suspension of microconidiae. The homogenate was inactivated by adding thiomersal in a ratio of 1:20000 (w strains DSM-7279, 9469, 9471, 9472 were cultivated separately on malt extract agar in 4 Roux flasks for each culture for 20 days at 28° C. Cultures of *Candida albicans* strains DSM-9456, 9457 were cultivated in 1 Roux flask for each culture on agar Sabouraud at 28° C. for 3 days.

The fungal masses of strains DSM-9469, 9471 and 9472 were lifted off, combined and homogenised in 100 ml of an aqueous solution of 0.3% fermented hydrolyzed muscle protein, 5% glucose and 0.1% yeast extract. The fungal masses of strain DSM-7279 and the mixture of strains DSM-9469, 9471 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. 500 ml of the *Trichophyton mentagrophytes* DSM-7279 suspension were mixed with 500 ml of the *Trichophyton rubrum* DSM-9469, 9471, 9472 mixture suspension in a single container.

The blastospores of strain DSM-9456, 9457 were lifted off by washing with 200 ml of destined water. The concentration of blastospores in suspension was adjusted to 60 million per ml. 250 ml of each suspension were mixed.

500 ml of the resulting suspension were mixed with the suspension of microconidiae. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

Following the inactivation the cell suspension was treated with sodium permanganate in a concentration of 1:10000 (w/v) for 36 hours while stirring. Treated cells were washed 5 times with destined water by centrifugation (4000 rpm) for 25 minutes for each centrifugation step. The final concentration of cells was adjusted to 60 million per ml.

The resulting vaccine was bottled, checked for sterility, safety and immunogenic properties in accordance with accepted methods and kept refrigerated at 4° C. The vaccine prepared in this manner was used to immunise animals by intramuscular injection. The efficacy after Trichophyton challenge is shown in tables 24–27 and FIGS. 11 and 12 and after *Candida albicans* challenge in table 44 (Complex VI-IV).

Example 27

Cultures of the strains *Trichophyton mentagrophytes* DSM-7279, *Trichophyton rubrum* DSM-9472 and *Candida albicans* DSM-9456, *Candida albicans* DSM-9457, *Candida albicans* DSM-9459 were used to prepare 1.5 liters of the vaccine. Cultures of strains DSM-7279, 9472 were cultivated separately on malt extract agar in 6 Roux flasks for each culture for 20 days at 28° C. Cultures of *Candida albicans* strains DSM-9456, 9457, 9459 were cultivated in 1 Roux flask for each culture on agar Sabouraud at 28° C. for 3 days.

The fungal masses of strains DSM-7279 and 9472 were lifted off and separately homogenised in 500 ml of an aqueous solution of 0.3% fermented hydrolyzed muscle protein, 5% glucose and 0.1% yeast extract. The concentration of microconidia was adjusted to 60 million per ml of the homogenate. 500 ml of the *Trichophyton mentagrophytes* DSM-7279 suspension were mixed with 500 ml of the *Trichophyton rubrum* DSM-9472 suspension in a single container.

The blastospores of strain DSM-9456, 9457, 9459 were lifted off by washing with 200 ml of destined water. The concentration of blastospores in suspension was adjusted to 60 million per ml. 250 ml of each suspension were and mixed. 500 ml of the resulting suspension were mixed with the suspension of microconidiae. The homogenate was inactivated by adding thiomersal in a ratio of 1:20000 (w/v) directly to the cell suspension. For this purpose 50 mg of thiomersal were added to 1 liter of homogenate. The mixture was incubated at room temperature for 2 days.

Following the inactivation the cell suspension was treated with $H_2O_2$. A substance containing $H_2O_2$, for example Urea-hydrogen peroxide, was added to the cell suspension to yield a final concentration of 3% of $H_2O_2$. The cell suspension was stirred for 36 hours. Treated cells were washed 5 times for 25 minutes with destined water by centrifugation (4000 rpm). The final concentration of the cells was adjusted to 60 million per ml.

The resulting vaccine was bottled, checked for sterility, safety and immunogenic properties in accordance with accepted methods and kept refrigerated at 4° C. The vaccine prepared in this manner was used to immunise animals by intramuscular injection.

Example 28

Efficacy of the Vaccines after $LD_{50}$ *Candida albicans* Challenge in Mice

The challenge was applied through intraperitoneal injection of 45 million *Candida albicans* blastospores per mouse. A single dose of 0.3 ml of the vaccine was applied subcutaneously on the same day as the challenge and a second dose after 7 days. The observation was continued for 4 weeks after the initial injection of vaccine. Complexes 1-I, 1-II, 2-I were tested in this manner (see tables 1, 2, 3, 4).

Example 29

Efficacy of the Vaccines after $ID_{100}$ *Candida albicans* Challenge in Mice

The challenge was applied through intraperitoneal injection of 10 million *Candida albicans* blastospores per mouse. A single dose of 0.3 ml of the vaccine was applied subcutaneously on the same day as the challenge and a second dose after 7 days. The observation was continued for 4 weeks after the initial injection of vaccine. Complexes 3-I, 3-II, 4-I were tested in this manner (see tables 5, 6, 23, 44, 45).

Example 30

Efficacy of the Vaccines after Trichophyton Challenge in Guinea Pigs

The challenge of *Trichophyton rubrum* microconidiae consisted of 500 thousand microconidia per $cm^2$ (1.5 million microconidia) applied topically for each animal.

The challenge of *Trichophyton mentagrophytes* microconidia consisted of 100–200 thousand microconidia per $cm^2$ (300–600 thousand microconidia) applied topically for each animal.

A single dose of 1.0 ml of the vaccine was applied through intramuscular injection on the same day as the challenge and a second dose after 7 days. The observation was continued for 4 weeks after the initial injection of vaccine. Complexes I-I, I-II, II-I, II-II, III-I, III-II, III-III, III-IV, III-V (see tables 7, 8, 9, 10, 11, 12, 13, 14 and FIGS. 1, 2, 3, 4) were tested.

The clinical symptoms of Trichophyton infection in guinea pigs were evaluated using the following severity scores:
0=no symptoms
1=hyperaemia of the skin at the place of fungi application
2=single spots of scaling
3=scaling of the skin at the place of fungi application 4=thin small crusts at the place of fungi application
5=scab-like crusts at the place of fungi application Example 31

Efficacy of the Vaccines after Trichophyton Challenge in Rabbits

The challenge of *Trichophyton rubrum* microconidiae consisted of 500 thousand microconidia per cm² (1.5 million microconidia) applied topically for each animal.

A single dose of 2.0 ml of the vaccine was applied through by intramuscular injection on the same day as the challenge and a second dose after 7 days. The observation was continued for 4 weeks after the initial injection of vaccine. Complex II-I (see tables 15, 16 and FIG. 5) was tested. The clinical symptoms of a Trichophyton infection in rabbits were evaluated using the same severity scores cited in example 30.

Example 32

Cultures of the strains *Trichophyton mentagrophytes* DSM-7279, *Trichophyton rubrum* DSM-9472 and *Candida albicans* DSM-9456 were used to prepare 1.5 liters of vaccine. *Trichophyton mentagrophytes* DSM-7279 and *Trichophyton rubrum* DSM-9472 were cultivated separately on agar/wort in 3 Roux flasks for each culture for 20 days at 28° C. *Candida albicans* DSM-9456 was cultivated in 2 Roux flasks on agar Sabouraud at 28° C. for 3 days. The fungal masses of the strains DSM-7279 and 9472 were then lifted off and separately homogenised in 500 ml of an aqueous solution containing 0.3% pork peptone (Oxoid), 5% glucose and 0.1% yeast extract. The concentration of microconidia was adjusted to 60 million per ml for each homogenate. To yield 50 to 100% germ tubes each suspension of microconidia was fermented for 1 to 2 days at 28° C. Then the cell suspensions were washed with a physiological solution of sodium chloride 5 times by centrifugation (4000 rpm) at 10° C. for 25 minutes each centrifugation step.

The blastospores of strain DSM-9456 were lifted off by washing with 500 ml of physiological solution of sodium chloride. The concentration of blastospores in suspension was adjusted to 60 million per ml.

500 ml of each culture in suspension were combined and mixed in a single container.

To inactivate the homogenate mixture, thiomersal in the ratio 1:20000 was added directly to the cell suspension. For this purpose 75 mg of thiomersal were added to 1.5 liters of homogenate. The mixture was then allowed to stand at room temperature for 2 days.

The resulting vaccine was bottled, checked for sterility, safety and immunogenic properties in accordance with accepted methods and kept refrigerated at 4° C.

Vaccine produced in this manner was used to immunise animals. The resulting suspension was packaged and ready for use in mammals. Efficacy of the vaccine after *Trichophyton rubrum* and *Trichophyton mentagrophytes* challenge in guinea pigs and rabbits are shown in tables 17, 18, 19, 20, 21, 22 and FIGS. 6, 7, 8, 9, 10 (Complex IV-II) and after *Candida albicans* challenge in mice in table 23.

Example 33

To produce 1.5 liters vaccine cultures of the strains *Trichophyton mentagrophytes* DSM-7279, *Trichophyton rubrum* DSM-9472 and *Candida albicans* DSM-9456 were used. *Trichophyton mentagrophytes* DSM-7279 and *Trichophyton rubrum* DSM-9472 were cultivated separately on agar/wort in 3 Roux flasks each culture for 20 days at 28° C. The *Candida albicans* DSM-9456 was cultivated in 2 Roux flasks on agar Sabouraud at 28° C. for 3 days. The fungal masses of the strains DSM-7279 and 9472 were then lifted off, separately homogenised in 500 ml of an aqueous solution containing 0.3% pork peptone (Biteck, Difco), 5% glucose and 0.1% yeast extract. The concentration of microconidia was adjusted to 60 million per ml for each homogenate. To yield 50 to 100% of germ tubes each suspension of microconidia was fermented for 1 to 2 days at 28° C.

Then the cell suspensions were washed with a physiological solution of sodium chloride 5 times by centrifugation (4000 rpm) at 10° C. for 25 minutes each centrifugation step.

The blastospores of strain DSM-9456 were lifted off by washing with 500 ml of a physiological solution of natrium chloride. The concentration of blastospores in suspension was adjusted to 60 million per ml.

500 ml of each culture in suspension was then taken and mixed in a single container.

To inactivate the homogenate mixture, thiomersal in the ratio 1:20000 was added directly to the cell suspension. For this purpose 75 mg of thiomersal were added to 1.5 liters of homogenate. The mixture was then allowed to stand at room temperature for 2 days.

The resulting vaccine was bottled, checked for sterility, safety and immunogenic properties in accordance with accepted methods and kept refrigerated at 4° C.

Vaccine produced in this manner was used to immunise animals. The resulting suspension was packaged and ready for use in mammals. Efficacy of the vaccine after *Trichophyton rubrum* and *Trichophyton mentagrophytes* challenge in guinea pigs were shown in tables 17, 18 and FIGS. 6 (Complex IV-III).

Example 34

Efficacy of the Vaccines after Trichophyton, Microsporum and Candida Challenge in Guinea Pigs The challenge of *Trichophyton rubrum* microconidiae consisted of 500 thousand microconidia per cm² (1.5 million microconidia) applied topically to each animal.

The challenge of *Trichophyton mentagrophytes* microconidiae consisted of 100–200 thousand microconidia per cm² (300–600 thousand microconidia) applied topically to each animal.

The challenge of *Microsporum canis* microconidiae consisted of 500 thousand microconidia per cm² (1.5 million microconidia) applied topically to each animal.

The challenge of 0.3 ml of past-like suspension *Candida albicans* blastospores obtain from the surface of 2 days old culture was applied topically to each animal.

A single dose of 1.0 ml of the vaccine was applied by intramuscular injection on the same day as the challenge and a second dose after 7 days. The observation was continues for 4 weeks after the initial injection of the vaccine. Complexes IV-I, IV-II, IV-III (see tables 17, 18, 19, 20 and FIGS. 6, 7, 8) were tested.

A single dose of 0.75 ml of the vaccine was applied through intramuscular injection on the same day as the challenge and a second dose after 7 days. The observation was continued for 4 weeks after the initial injection of vaccine. Complex VIII-II (see tables 38, 39, 40, 41, 42, 43 and FIGS. 18, 19, 20) were tested.

A single dose of 0.5 ml of the vaccine was applied by intramuscular injection on the same day as the challenge and a second dose after 7 days. The observation was continued for 4 weeks after the initial injection of vaccine. Complexes VI-I, VI-II, VI-III, VI-IV, VI-V, VI-VI, VII-I, VII-II, VII-III, VII-IV, VII-V, VII-VI, VII-VII, VIII-I, (see tables 24–37 and FIGS. 11–17) were tested.

The clinical symptoms of a Trichophyton, Microsporum and Candida infection in guinea pigs were evaluated using the following severity scores:
0=no symptoms
1=hyperaemia of the skin at the place of fungi application
2=single spots of scaling
3=scaling of the skin at the place of fungi application
4=thin small crusts at the place of fungi application
5=scab-like crusts at the place of fungi application Example 35
Efficacy and Safety Tested in Mice A single dose of 0.2 ml of the vaccine was applied subcutaneously and a second dose after 7 days on the same day as the challenge. The observation was continued for 4 weeks after the initial injection of vaccine. Complexes IV-II, VI-I, VI-II, VI-II, VI-IV, VI-V, VI-VI were tested in this manner (see tables 23, 44).

The safety and prophylactic activity of the vaccine in different doses were tested. A single dose of 0.1, 0.2, 0.5, 1.0 and 2.0 ml of the vaccine was applied subcutaneously and a second dose after 7 days. The 0.5 ml dose of vaccine was injected in two places, 1.0 and 2.0 ml were applied in three places of the animals body. After 4 weeks the mice were challenged. The observation was continued for 4 weeks after the initial injection of vaccine and 4 weeks after challenge. Complexes VIII-I was tested in this manner (see tables 45 and 46).

Example 36
Efficacy of the Vaccines after Trichophyton Challenge in Rabbits

The challenge of *Trichophyton rubrum* microconidiae consisted of 500 thousand microconidia per $cm^2$ (1.5 million microconidia) applied topically to each animal.

A single dose of 2.0 ml of the vaccine was applied by intramuscular injection on the same day as the challenge and a second dose after 7 days. The observation was continued for 4 weeks after the initial injection of vaccine. Complexes IV-II (see tables 21, 22 and FIGS. 9, 10) were tested. The clinical symptoms of Trichophyton infections in rabbits were evaluated using the same severity score as cited in example 34.

Example 37
Efficacy of the Vaccines after Trichophyton Challenge in Guinea Pigs with Immunosuppresive Treatment The challenge of *Trichophyton rubrum* microconidiae consisted of 500 thousand microconidia per $cm^2$ (1.5 million microconidia) applied topically to each animal.

The challenge of *Trichophyton mentagrophytes* microconidiae consisted of 100–200 thousand microconidia per $cm^2$ (300–400 thousand microconidia) applied topically to each animal.

Hostacortin H was used as an immunosuppressant. 1 ml kristall suspension contained: 10 mg Prednisolon-21-acetate and 9.45 mg benzylalkohol. A single dose of 0.1 ml of Hostacortin suspension was applied by intramuscular injection on the same day as the challenge, a second dose after 3 days and a third dose after 7 days.

A single dose of 0.5 ml of the vaccine was applied through intramuscular injection on the same day as the challenge and a second dose after 7 days. The observation was continued for 4 weeks after the initial injection of the vaccine. Complexes VIII-I+H and Control+H (unvaccinated animals treated by Hostacortin H) (see tables 32–35 and FIGS. 15, 16) were tested. The clinical symptoms of a Trichophyton infection in guinea pigs were evaluated using the following severity scores:
0=no symptoms
1=hyperaemia of the skin at the place of fungi application
2=single spots of scaling
3=scaling of the skin at the place of fungi application
4=thin small crusts at the place of fungi application
5=scab-like crusts at the place of fungi application Example 38

The batch No.851 of the vaccine was produced in a factory. To produce 15 liters of vaccine cultures of the strains *Trichophyton mentagrophytes* DSM-7279, *Trichophyton rubrum* DSM-9472 and *Candida albicans* DSM-9456 were used. *Trichophyton mentagrophytes* DSM-7279 and *Trichophyton rubrum* DSM-9472 were cultivated separately on agar/wort in 10 Roux flasks for each culture for 20 days at 28° C. *Candida albicans* DSM-9456 was cultivated in 4 Roux flasks on agar Sabouraud at 28° C. for 3 days.

The fungal masses of the strains DSM-7279 and 9472 was then lifted off, separately homogenised in 500 ml of an aqueous solution containing 0.3% of pork peptone Oxoid, 5% glucose and 0.1% yeast extract. The concentration of microconidia was adjusted to 60 million per ml of each homogenate. To yield 50 to 100% germ tubes each suspension of microconidia was fermented for 1 to 2 days at 28° C.

Then the cell suspensions were washed by means of a cross flow system with a physiological solution of sodium chloride.

The blastospores of strain DSM-9456 were lifted off by washing by means of a cross flow system with a physiological solution of sodium chloride. The concentration of blastospores in suspension was adjusted to 60 million per ml. To inactivate the homogenates thiomersal in the ratio 1:20000 was added directly to the cell suspensions. 5000ml of each culture in suspension then taken and inactivated by thiomersal. For this purpose 250 mg of thiomersal were added to 5 liters of homogenate. The suspensions were then allowed to stand at room temperature for 2 days.

After inactivation the 5000 ml of each suspension was tested for sterility and inactivation. The sterile and inactivated suspensions were mixed. The resulting vaccine was bottled, checked for sterility, safety and immunogenic properties in accordance with accepted methods and kept refrigerated at 4° C.

Vaccine produced in this manner was used to immunise animals. The resulting suspension was packaged in large flasks and ready for use in mammals. Efficacy of the vaccine after *Trichophyton rubrum* and *Trichophyton mentagrophytes* challenge in guinea pigs are shown in tables 28–31 and FIGS. 13 and 14 (Complex VII-VII) and *Candida albicans* challenge is shown in table 45 and 46.

Example 39

The batch No.851/NF7522LO01 (May 28, 1997) of vaccine was produced in a factory.

To produce 15 liters vaccine cultures of the strains *Trichophyton mentagrophytes* DSM-7279, *Trichophyton rubrum* DSM-9472 and *Candida albicans* DSM-9456 were used. *Trichophyton mentagrophytes* DSM-7279 and *Trichophyton rubrum* DSM-9472 were cultivated separately on agar/wort in 10 Roux flasks for each culture for 20 days at 28° C. *Candida albicans* DSM-9456 was cultivated in 4 Roux flasks on agar Sabouraud at 28° C. for 3 days.

The fungal masses of the strains DSM-7279 and 9472 were then lifted off and separately homogenised in 500 ml of an aqueous solution containing 0.3% of pork peptone Oxoid, 5% glucose and 0.1% yeast extract. The concentration of microconidia was adjusted to 60 million per ml of each homogenate. To yield 50 to 100% of germ tubes each suspension of microconidia was fermented for 1 to 2 days at 28° C.

Then the cell suspensions were washed by means of a cross flow system with physiological solution of sodium chloride.

The blastospores of strain DSM-9456 were lifted off by washing by means of a cross flow system with a physiological solution of sodium chloride. The concentration of blastospores in suspension was adjusted to 60 million per ml. To inactivate the homogenates thiomersal in a ratio of 1:20000 was added directly to the cell suspensions. 5000 ml of each culture in suspension was then taken and inactivated by thiomersal. For this purpose 250 mg of thiomersal were added to 5 liters of homogenate. The suspensions were then allowed to stand at room temperature for 2 days.

After inactivation the 5000 ml of each suspension were tested for sterility and inactivation. The sterile and inactivated suspensions were mixed.

The resulting vaccine waste bottled, checked for sterility, safety and immunogenic properties in accordance with accepted methods and kept refrigerated at 4° C.

Vaccine produced in this manner was used to immunise animals. The 600 ml of resulting vaccine batch No.851 was packaged in 1080 flasks of 0.6 ml of vaccine each and ready for use. Efficacy of the vaccine after *Trichophyton rubrum* and *Trichophyton mentagrophytes* challenge in guinea pigs are shown in tables 32–37 and FIGS. 15, 16, 17 (Complex VIII-I).

Example 40

5.5 ml of vaccine batch No.851 (see example 38) was mixed with 0.7 ml of Immukin® (interferon gamma-1b), produced by the Dr. Karl Thomae GmbH on Dec. 12, 1996, batch No.612608, with a concentration of 0.1 mg in 0.5 ml of aquous solution. The complexes were prepared directly before application to animals. The resulting suspension was packaged in flasks and ready for use in animals. Efficacy of the vaccine after *Trichophyton rubrum* and *Trichophyton mentagrophytes* challenge in guinea pigs are shown in tables 28–31 and FIGS. 13 and 14 (Complex VII-I).

Example 41

5.5 ml of vaccine batch No.851 (see example 38) was mixed with 10 μg of rhTNF-alfa produced in Promega (USA) batch No.7186801. The complexes were prepared directly before application to animals.

The resulting suspension was packaged in flasks and ready for use in animals. Efficacies of the vaccine after *Trichophyton rubrum* and *Trichophyton mentagrophytes* challenge in guinea pigs are shown in tables 28–31 and FIGS. 13 and 14 (Complex VII-III).

Example 42

5.5 ml of vaccine batch No.851 (see example 38) was mixed with 5 μg of recombinant IL-2, Human produced in Promega (USA) batch No.5970601. The complexes were prepared directly before application to animals.

The resulting suspension was packaged in flasks and ready for use in animals. Efficacy of the vaccine after *Trichophyton rubrum* and *Trichophyton mentagrophytes* challenge in guinea pigs are shown in tables 28–31 and FIGS. 13 and 14 (Complex VII-III).

Example 43

5.5 ml of vaccine batch No.851 (see example 38) was mixed with 5 μg of recombinant IL-12, Human produced in Sigma batch No. 86H6661. The complexes were prepared directly before application in animals.

The resulting suspension was packaged in flasks and ready for use in animals. Efficacy of the vaccine after *Trichophyton rubrum* and *Trichophyton mentagrophytes* challenge in guinea pigs are shown in tables 28–31 and FIGS. 13, 14 (Complex VII-IV).

Example 44

5.5 ml of vaccine batch No.851 (see example 38) was mixed with 20 μg of recombinant hIL-8(72 Aa), produced by Boehringer Manheim, batch No.14788621. The complexes were prepared right before application to animals.

The resulting suspension was packaged in flasks and ready for use in animals. Efficacy of the vaccine after *Trichophyton rubrum* and *Trichophyton mentagrophytes* challenge in guinea pigs are shown in tables 28–31 and FIGS. 13 and 14 (Complex VII-V).

Example 45

5.5 ml of vaccine batch No.851 (see example 38) was mixed with 2.5 μg of recombinant IL-4, Human, produced in Promega batch No.7099101. The complexes were prepared directly before application to animals. The resulting suspension was packaged in flasks and ready for use in animals. Efficacy of the vaccine after *Trichophyton rubrum* and *Trichophyton mentagrophytes* challenge in guinea pigs are shown in tables 28–31 and FIGS. 13, 14 (Complex VII-VI).

Example 46

50 ml of vaccine batch No.851 (see example 38) were mixed with 25 ml of inactivated *Microsporum canis*, DSM No.7281, suspension of microconidia with 60% germs tubes and with a concentration of 50 million cells per 1 ml of physiological aquous solution of sodium chloride.

The resulting suspension was packaged in flasks and ready for use in animals. Efficacy of the vaccine after *Trichophyton rubrum, Trichophyton mentagrophytes* and *Microsporum canis* challenge in guinea pigs are shown in tables 38–43 and FIGS. 18–20 (Complex VIII-II).

Example 47

10 ml of vaccine batch No.851 (see example 38) were mixed with 25 ml of inactivated "Rotlauf" vaccine against erysipelas (standard RF-2 of Paul-Ehrlich-Institute, Germany) with 0.2 IU of activity per dose.

Another 10 ml of vaccine batch No.851 (see example 38) were mixed with 25 ml of inactivated "Rotlauf" vaccine against erysipelas (standard RF-2 of Paul-Ehrlich-Institute, Germany) with 1.0 IU of activity per dose.

Another 10 ml of vaccine batch No.851 (see example 38) were mixed with 25 ml of inactivated "Rotlauf" vaccine against erysipelas (standard RF-2 of Paul-Ehrlich-Institute, Germany) with 5.0 IU of activity in dose. The resulting suspension was packaged in flasks and ready for use in animals. Efficacies of the vaccines after erysipelas challenge in mice are shown in tables 47 (RF-2+Complex VIII-I).

Positive controls of activity were vaccines against erysipelas (standard RF-2 of Paul-Ehrlich-Institute, Germany) with 0.2 IU, 1.0 IU and 5.0 IU of activity per dose.

After 21 days all vaccinated and control animals were challenged with virulent cultures of erysipelas. The efficacy was calculated according the Paul-Ehrlich-Institute standard method, Germany.

Example 48

The efficacy of a vaccine prepared as described in Example 1 from *Candida albicans* DSM No. 9456, *Trichophyton mentagrophytes* DSM No. 7279, *Trichophyton rubrum* DSM No. 9472 was demonstrated by the vaccination of a 41 year old man with Heroes simplex labialis.

Intramuscular injection of a volume of 1.0 ml of vaccine with an interval of 14 days between each application resulted in the cure of the vaccinated patient 4 to 5 days after the first injection. All clinical symptoms including the itching disappeared. No side effects were observed.

Example 49

The efficacy of a vaccine prepared as described in Example 2 from *Candida albicans* DSM No. 9456, *Trichophyton mentagrophytes* DSM No. 7279, *Trichophyton rubrum* DSM No. 9472 was demonstrated by the vaccination of a 42 year old man with chronic follicular pyoderma.

Intramuscular injection of a volume of 1.0 ml of vaccine with an interval of 14 days between each application resulted in the cure of the vaccinated pacient 4 to 6 weeks after the last injection, as demonstrated by significant reduction of the amount of subcorneal pustules and the intensity of clinical symptoms. No severe side effects were observed.

Example 50

The efficacy of a vaccine prepared as described in Example 2 from *Candida albicans* DSM No. 9456, *Trichophyton mentagrophytes* DSM No.7279, *Trichophyton rubrum* DSM No. 9472 was demonstrated by the vaccination of 12 year old boy with Common warts (*Verucae vulgares* and paronychial warts).

The vaccine was injected two times at an interval of two month intramuscularly, resulting in a significant reduction of the amount of warts after the first injection and the warts disappeared 30 days after the second injection. No severe side effects were observed.

Results of an $LD_{50}$ *Candida albicans* Challenge in Vaccinated Mice (1st Experiment)

TABLE 1

Acute pathogenic activity
(For method see example 28)

| COMPLEXES | Number of animals | Number of died animals during acute period | % loss of animals |
|---|---|---|---|
| Complex 1-I (Example 8) | 10 | 5 | 50 |
| Complex 1-II (Example 16) | 10 | 4 | 40 |
| Control (destilled water) | 11 | 5 | 45.5 |

When using the $LD_{50}$ challenge dose there was the same death rate in mice (40–50%) in experimental and control groups of animals during the period of acute pathogenicity (3 days after injection).

TABLE 2

Development of the disease
(For method see example 28)

| COMPLEXES | Number of animals | Number of animals with symptoms *Candida albicans* infection | % of infected animals |
|---|---|---|---|
| Complex 1-I (Example 8) | 5 | 2 | 40 |
| Complex 1-II (Example 16) | 6 | 2 | 33.3 |
| Control (destilled water) | 6 | 6 | 100 |

During the follow-up period (day 4 to day 28) 100% of the survivors of the unvaccinated control group developed clinical symptoms of candidiasis while the efficacy rate in vaccinated animals was 60% (Complex 1-I) and 66.7% (Complex 1-II) respectively.

Results of an $LD_{50}$ *Candida albicans* Challenge in Vaccinated Mice (2nd Experiment)

TABLE 3

Acute pathogenic activity
(For method see example 28)

| COMPLEXES | Number of animals | Number of loss of mice during acute period | % loss of mice |
|---|---|---|---|
| Complex 2-I (Example 16) | 10 | 4 | 40 |
| Untreated control | 11 | 4 | 36 |

Using the $LD_{50}$ challenge dose 40% and 36% of the animals died in the experimental group and control group respectively during the period of acute pathogenicity (3 days after injection).

TABLE 4

Development of the disease
(For method see example 28)

| COMPLEXES | Number of animals | Number of animals with symptoms of Candida albicans infection | % of infected animals |
|---|---|---|---|
| Complex 2-I (Example 16) | 6 | 3 | 50 |
| Untreated control | 7 | 7 | 100 |

During the follow up period (day 4 to day 28) 100% of the survivors of the unvaccinated control group developed clinical symptoms of candidiasis while the efficacy rate in vaccinated animals was 50% (Complex 2-I).

Results of an $ID_{100}$ Candida albicans Challenge in Vaccinated Mice (3rd Experiment)

TABLE 5

Development of the disease
(For method see example 29)

| COMPLEXES | Number of animals | Number of animals with symptoms of Candida albicans infection | % of infected animals |
|---|---|---|---|
| Complex 3-I (Example 8) | 10 | 3 | 30 |
| Complex 3-II (Example 16) | 10 | 7 | 70 |
| Untreated control | 11 | 9 | 82 |

When using ID100 70% of the animals vaccinated by Complex 3-I and 30% of the animals vaccinated by Complex 3-II were healthy while 82% of the animals of the control group suffered from clinical symptoms of candidiasis.

Results of an $ID_{100}$ Candida albicans Challenge in Vaccinated Mice (4th Experiment)

TABLE 6

Development of disease
(For method see example 29)

| COMPLEXES | Number of animals | Number of animals with symptoms of Candida albicans infection | % of infected animals |
|---|---|---|---|
| Complex 4-I (Example 12) | 10 | 1 | 10 |
| Untreated control | 10 | 8 | 80 |

When using ID100 90% of the animals vaccinated by Complex 4-I were healthy while 80% of the mice of the control group had clinical symptoms of candidiasis.

Clinical Symptoms of *Trichophyton rubrum* Disease in Guinea Pigs (1st experiment)

TABLE 7

(For method see example 30)

| Complexes | | day 7 | day 13 | day 21 | day 28 |
|---|---|---|---|---|---|
| Complex I-I (Example 8) | mean | 0 | 3.2 | 2.4 | 0 |
| Complex I-II (Example 16) | mean | 0.6 | 2.8 | 2.8 | 0.8 |
| Untreated control | mean | 1.0 | 5.0 | 4.0 | 1.8 |

The severity of clinical symptoms of rubrophytosis in challenged guinea pigs is shown after different observation periods. Compared with vaccinated animals (Complexes I-I and I-II) unvaccinated control animals had more severe clinical symptoms (see FIG. 1).

Number of Guinea Pigs with Clinical Symptoms of *Trichophyton rubrum* Disease (1st Experiment)

TABLE 8

(For method see example 30)

| COMPLEXES | day 7 | day 13 | day 21 | day 28 |
|---|---|---|---|---|
| Complex I-I Example 8 | 0/5 | 5/5 | 5/5 | 0/5 |
| Complex I-II (Example 16) | 3/5 | 5/5 | 5/5 | 2/5 |
| Untreated control | 5/5 | 5/5 | 5/5 | 4/5 |

(Note: number of animals with clinical symptoms/number of challenged animals)

Compared with the control group there were less animals with clinical symptoms on day 7 and 28 after vaccination.

Clinical Symptoms of *Trichophyton rubrum* Disease in Guinea Pigs (2nd Experiment)

TABLE 9

(For method see example 30)

| Complexes | | day 7 | day 15 | day 21 | day 28 |
|---|---|---|---|---|---|
| Complex II-I (Example 1) | mean | 0 | 2.3 | 0.66 | 0.66 |
| Complex II-II (Example 20) | mean | 0.5 | 2.25 | 1.5 | 1.5 |
| Untreated control | mean | 3.2 | 3.4 | 3.2 | 2.6 |

The severity of clinical symptoms of rubrophytosis in challenged guinea pigs is shown after different observation periods. Compared with vaccinated animals (Complexes II-I and II-II) unvaccinated control animals had more severe clinical symptoms (see FIG. 2).

Number of Guinea Pigs with Clinical Symptoms of
*Trichophyton rubrum* Disease (2nd Experiment)

TABLE 10

(For method see example 30)

| COMPLEXES | Date of observation | | | |
|---|---|---|---|---|
|  | day 7 | day 15 | day 21 | day 28 |
| Complex II-I (Example 1) | 0/3 | 3/3 | 1/3 | 1/3 |
| Complex II-II (Example 20) | 1/4 | 4/4 | 3/4 | 3/4 |
| Untreated control | 5/5 | 5/5 | 5/5 | 5/5 |

(Note: number of animals with clinical symptoms/number of challenged animals)

Compared with the control group there were less animals with clinical symptoms in both vaccination groups at each day of observation.

Clinical Symptoms of *Trichophyton rubrum* Disease in Guinea Pigs (3rd Experiment)

TABLE 11

(For method see example 30)

| Complexes | | Date to observation | | | |
|---|---|---|---|---|---|
|  |  | day 7 | day 16 | day 21 | day 28 |
| Complex III-I (Example 1) | mean | 0.6 | 2.6 | 0 | 0 |
| Complex III-II (Example 2) | mean | 0.75 | 2.5 | 0 | 0 |
| Complex III-III (Example 3) | mean | 1.75 | 4 | 2 | 2 |
| Complex III-IV (Example 4) | mean | 2.5 | 4 | 2.25 | 1.25 |
| Complex III-V | mean | 1.8 | 3.2 | 2.6 | 1.6 |
| Untreated control | mean | 2.75 | 5 | 4 | 1.75 |

The severity of clinical symptoms of rubrophytosis in challenged guinea pigs is shown after different observation periods. Compared with vaccinated animals (Complexes II-I, III-II, III-III, III-IV, III-V) unvaccinated control animals had more severe clinical symptoms (see FIG. 3).

Number of Guinea Pigs with Clinical Symptoms of
*Trichophyton rubrum* Disease (3rd Experiment)

TABLE 12

(For method see example 30)

| COMPLEXES | Date of observation | | | |
|---|---|---|---|---|
|  | day 7 | day 16 | day 21 | day 28 |
| Complex III-I (Example 1) | 3/5 | 5/5 | 0/5 | 0/5 |
| Complex III-II (Example 2) | 3/4 | 4/4 | 0/4 | 0/4 |
| Complex III-III (Example 3) | 4/4 | 4/4 | 4/4 | 4/4 |
| Complex III-IV (Example 4) | 4/4 | 4/4 | 4/4 | 4/4 |
| Complex III-V (Example 12) | 5/5 | 5/5 | 5/5 | 5/5 |
| Untreated control | 4/4 | 4/4 | 4/4 | 4/4 |

(Note: number of animals with clinical symptoms/number of challenged animals)

Clinical Symptoms of *Trichophyton mentagrophytes* Disease in Guinea Pigs (3rd Experiment)

TABLE 13

(For method see example 30)

| Complexes | | Date of observation | | | |
|---|---|---|---|---|---|
|  |  | day 7 | day 16 | day 21 | day 28 |
| Complex III-I (Example 1) | mean | 2.0 | 4.0 | 2.25 | 1.0 |
| Complex III-II (Example 2) | mean | 1.8 | 3.8 | 2.4 | 0.8 |
| Complex III-III (Example 3) | mean | 4.0 | 4.6 | 1.6 | 1.2 |
| Complex III-IV (Example 4) | mean | 3.6 | 4.3 | 2.0 | 0.6 |
| Complex III-V (Example 12) | mean | 3.6 | 4.8 | 2.4 | 1.4 |
| Untreated control | mean | 4.0 | 4.4 | 3.6 | 2.6 |

The severity of clinical symptoms of *Trichophyton mentagrophytes* infection in challenged guinea pigs is shown after different observation periods. Compared with vaccinated animals (Complexes III-I, III-II, III-III, III-IV, III-V) unvaccinated control animals had more severe clinical symptoms (see FIG. 4).

Number of Guinea Pigs with Clinical Symptoms of
*Trichophyton mentagrophytes* Disease (3rd Experiment)

TABLE 14

(For method see example 30)

| COMPLEX | Date of observation | | | |
|---|---|---|---|---|
| | day 7 | day 16 | day 21 | day 28 |
| Complex III-I (Example 1) | 4/4 | 4/4 | 4/4 | 4/4 |
| Complex III-II (Example 2) | 5/5 | 5/5 | 5/5 | 4/5 |
| Complex III-III (Example 3) | 5/5 | 5/5 | 5/5 | 3/5 |
| Complex III-IV (Example 4) | 3/3 | 3/3 | 3/3 | 2/3 |
| Complex III-V (Example 12) | 5/5 | 5/5 | 5/5 | 2/5 |
| Untreated control | 5/5 | 5/5 | 5/5 | 5/5 |

(Note: number of animals with clinical symptoms/number of challenged animals)

Nearly all vaccinated animals displayed clinical symptoms during the observation period.

Clinical Symptoms of *Trichophyton rubrum* Disease in Rabbits (1st Experiment)

TABLE 15

(For method see example 31)

| Complex | | Date of observation | | | |
|---|---|---|---|---|---|
| | | day 7 | day 15 | day 21 | day 28 |
| Complex II-I (Example 1) | mean | 1.4 | 2.0 | 0.4 | 0 |
| Untreated control | mean | 3.0 | 3.8 | 2.6 | 2.4 |

The severity of clinical symptoms of *Trichophyton rubrum* infection in challenged rabbits is shown after different observation periods. Compared with vaccinated animals (Complex II-I) unvaccinated control animals had more severe clinical symptoms (see FIG. 5).

Number of Rabbits with Clinical Symptoms of
*Trichophyton rubrum* Disease (1st Experiment)

TABLE 16

(For method see example 31)

| COMPLEX | Date of observation | | | |
|---|---|---|---|---|
| | day 7 | day 15 | day 21 | day 28 |
| Complex II-I (Example 1) | 4/5 | 5/5 | 1/5 | 0/5 |
| Untreated control | 5/5 | 5/5 | 4/5 | 4/5 |

(Note: number of animals with clinical symptoms/number of challenged animals)

Compared with the control group almost all vaccinated animals did not display clinical symptoms on days 21 and 28.

Clinical Symptoms of *Trichophyton rubrum* Disease in Guinea Pigs (4th Experiment)

TABLE 17

(For method see example 34)

| Complexes | | Date of observation | | | |
|---|---|---|---|---|---|
| | | day 7 | day 14 | day 23 | day 28 |
| IV-I (Example 1) | mean | 1.0 | 3.4 | 0.2 | 0 |
| IV-II (Example 32) | mean | 1.8 | 3.2 | 0.2 | 0 |
| IV-III (Example 33) | mean | 2.1 | 3.3 | 0.3 | 0 |
| Untreated control | mean | 1.4 | 4.2 | 2.3 | 1.7 |

The severity of clinical symptoms of *Trichophyton rubrum* infection in challenged guinea pigs is shown after different observation periods. Compared with vaccinated animals (Complex IV-I, ComplexIV-II, Complex IV-III) unvaccinated control animals had more severe clinical symptoms (see FIG. 6)

Number of Guinea Pigs with Clinical Symptoms of
*Trichophyton rubrum* Disease

TABLE 18

(For method see example 34)

| COMPLEX/VACCINE | Date of observation | | | |
|---|---|---|---|---|
| | day 7 | day 14 | day 23 | day 28 |
| Complex IV-I (Example 1) | 2/5 | 5/5 | 1/5 | 0/5 |
| Complex IV-II (Example 32) | 4/5 | 5/5 | 1/5 | 0/5 |
| Complex IV-III (Example 33) | 5/5 | 5/5 | 2/5 | 0/5 |
| Untreated control | 11/16 | 16/16 | 15/16* | 12/16** |

Note:
number of animals with clinical symptoms/number of challenged animals
*3 animals had secondary infection;
**5 animals had secondary infection.

Compared with the control group almost all vaccinated animals did not display clinical symptoms on day 29.

Clinical Symptoms of *Trichophyton rubrum* Disease in Guinea Pigs

TABLE 19

(For method see example 34)

| Complex | | Date of observation | | | |
|---|---|---|---|---|---|
| | | Day 10 | Day 16 | Day 22 | Day 29 |
| IV-II (Example 32) | mean | 1.4 | 2.2 | 0.7 | 0.1 |
| Untreated control | mean | 2.1 | 3.5 | 2.6 | 1.7 |

The severity of clinical symptoms of *Trichophyton rubrum* infection in challenged guinea pigs is shown after different observation periods. Compared with vaccinated animals (ComplexIV-II) unvaccinated control animals had more severe clinical symptoms (see FIG. 7)

Number of Guinea Pigs with Clinical Symptoms of *Trichophyton rubrum* Disease

TABLE 20

(For method see example 34)

| Group | Complex/Vaccine | Date of observation | | | |
|---|---|---|---|---|---|
| | | Day 10 | Day 16 | Day 22 | Day 29 |
| 1 | IV-II (Example 32) | 16/17 | 15/17 | 8/17 | 1/17 |
| 2 | Untreated control | 13/16 | 15/16 | 16/16 | 12/16 |

(Note: Number of animals with clinical symptoms/number of challenged animals)

Compared with the control group almost all vaccinated animals did not display clinical symptoms on day 29 (see FIG. 8)

Clinical Symptoms of *Trichophyton rubrum* Disease in Rabbits

TABLE 21

(For method see example 36)

| Complex | | Date of observation | | | |
|---|---|---|---|---|---|
| | | Day 10 | Day 16 | Day 22 | Day 29 |
| IV-II (Example 32) | mean | 1.8 | 1.1 | 0.5 | 0.2 |
| Untreated control | mean | 2.6 | 3.2 | 2.4 | 1.8 |

The severity of clinical symptoms of *Trichophyton rubrum* infection in challenged rabbits is shown after different observation periods. Compared with vaccinated animals (ComplexIV-II) unvaccinated control animals had more severe clinical symptoms (see FIG. 9)

Number of Rabbits with Clinical Symptoms of *Trichophyton rubrum* Disease

TABLE 22

(For method see example 36)

| Group | Complex/ Vaccine | Date of observation | | | |
|---|---|---|---|---|---|
| | | Day 10 | Day 16 | Day 22 | Day 29 |
| 1 | IV-II (Example 32) | 9/10 | 6/10 | 3/10 | 1/10 |
| 2 | Untreated control | 10/10 | 10/10 | 9/10 | 7/10 |

(Note: Number of animals with clinical symptoms/number of challenged animals)

Compared with the control group almost all vaccinated animals did not display clinical symptoms on day 29 (see FIG. 10)

Results of an $ID_{100}$ *Candida albicans* Challenge in Vaccinated Mice (6th experiment)

TABLE 23

Development of the disease
(Method see example 29, 35)

| COMPLEXES | Number of animals | Number of animals with symptoms of *Candida albicans* infection | % of infected animals |
|---|---|---|---|
| Complex IV-II (Example 32) | 20 | 11 | 55 |
| Untreated control | 20 | 16 | 80 |

When using ID100 45% of the animals vaccinated by Complex IV-II were healthy while 80% of the animals of the control group suffered from clinical symptoms of candidiasis.

Clinical Symptoms of *Trichophyton rubrum* Disease in Guinea Pigs

TABLE 24

(For method see example 34)

| Complex | | Date of observation | | | | |
|---|---|---|---|---|---|---|
| | | Day 7 | Day 13 | Day 21 | Day 28 | Day 33 |
| VI-I (Example 22) | mean | 0 | 2.6 | 0.8 | 0.2 | 0.4 |
| VI-II (Example 23) | mean | 0.6 | 3.6 | 1.8 | 0 | 0 |
| VI-III (Example 6) | mean | 0.4 | 3.4 | 1.6 | 0 | 0 |
| VI-IV (Example 26) | mean | 0.8 | 3.4 | 1.75 | 0 | 0 |
| VI-V (Example 25) | mean | 0.8 | 4.0 | 2.4 | 0 | 1.0 |
| VI-VI (Example 19) | mean | 0.8 | 4.2 | 3.6 | 0 | 0.2 |
| Untreated control | mean | 2.0 | 4.8 | 3.4 | 1.4 | 0.8 |

The severity of clinical symptoms of *Trichophyton rubrum* infection in challenged guinea pigs is shown after different observation periods. Compared with vaccinated animals unvaccinated control animals had more severe clinical symptoms in day 28 and 33. Only animals vaccinated by Complex VI-V had more clinical symptoms on day 33 (see FIG. 11).

Number of Guinea Pigs with Clinical Symptoms of *Trichophyton rubrum* Disease

TABLE 25

(For method see example 34)

| Group | Complex/ Vaccine | Date of observation | | | | |
|---|---|---|---|---|---|---|
| | | Day 7 | Day 13 | Day 21 | Day 28 | Day 33 |
| 1 | VI-I (Example 22) | 0/5 | 5/5 | 2/5 | 1/5 | 1/5 |
| 2 | VI-II (Example 23) | 2/5 | 5/5 | 3/5 | 0/5 | 0/5 |

TABLE 25-continued (For method see example 34)

| Group | Complex/ Vaccine | Day 7 | Day 13 | Day 21 | Day 28 | Day 33 |
|---|---|---|---|---|---|---|
| 3 | VI-III (Example 6) | 2/5 | 5/5 | 4/5 | 0/5 | 0/5 |
| 4 | VI-IV (Example 26) | 4/5 | 5/5 | 3/4 | 0/4 | 0/4 |
| 5 | VI-V (Example 25) | 4/5 | 5/5 | 5/5 | 0/5 | 3/5 |
| 6 | VI-VI (Example 19) | 4/5 | 5/5 | 5/5 | 0/5 | 1/5 |
| 7 | Untreated control | 5/5 | 5/5 | 5/5 | 3/5 | 2/5 |

(Note: Number of animals with clinical symptoms/number of challenged animals)

Compared with the control group, a less number or none of the vaccinated animals had clinical symptoms on days 28 and 33. Compared with the control group more animals vaccinated by Complex VI-V had clinical symptoms on day 33.

Clinical Symptoms of *Trichophyton mentagrophytes* Disease in Guinea Pigs

TABLE 26

(For method see example 34)

| Complex | | Day 7 | Day 13 | Day 21 | Day 28 | Day 33 |
|---|---|---|---|---|---|---|
| VI-I (Example 22) | mean | 2.4 | 4.0 | 2.0 | 0.4 | 0.4 |
| VI-II (Example 23) | mean | 2.6 | 4.2 | 2.6 | 1.4 | 0.6 |
| VI-III (Example 6) | mean | 2.0 | 4.0 | 2.2 | 1.8 | 0.2 |
| VI-IV (Example 26) | mean | 2.4 | 4.0 | 2.4 | 1.4 | 1.0 |
| VI-V (Example 25) | mean | 2.6 | 4.0 | 2.6 | 1.2 | 0.5 |
| VI-VI (Example 19) | mean | 2.2 | 4.0 | 2.2 | 0.6 | 0.2 |
| Untreated control | mean | 3.0 | 5.0 | 3.6 | 2.6 | 2.6 |

The severity of clinical symptoms of *Trichophyton mentagrophytes* infection in challenged guinea pigs is shown after different observation periods. Compared with vaccinated animals unvaccinated control animals had more severe clinical symptoms in observation times (see FIG. 12).

Number of Guinea Pigs with Clinical Symptoms of *Trichophyton mentagrophytes* Disease

TABLE 27

(For method see example 34)

| Group | Complex/ Vaccine | Day 7 | Day 13 | Day 21 | Day 28 | Day 33 |
|---|---|---|---|---|---|---|
| 1 | VI-I (Example 22) | 5/5 | 5/5 | 4/5 | 1/5 | 1/5 |
| 2 | VI-II (Example 23) | 5/5 | 5/5 | 5/5 | 4/5 | 2/5 |

TABLE 27-continued (For method see example 34)

| Group | Complex/ Vaccine | Day 7 | Day 13 | Day 21 | Day 28 | Day 33 |
|---|---|---|---|---|---|---|
| 3 | VI-III (Example 6) | 5/5 | 5/5 | 4/5 | 4/5 | 1/5 |
| 4 | VI-IV (Example 26) | 5/5 | 5/5 | 4/5 | 2/5 | 2/5 |
| 5 | VI-V (Example 25) | 5/5 | 5/5 | 5/5 | 3/4 | 2/4 |
| 6 | VI-VI (Example 19) | 4/5 | 5/5 | 5/5 | 2/5 | 1/5 |
| 7 | Untreated control | 5/5 | 5/5 | 5/5 | 5/5 | 5/5 |

(Note: Number of animals with clinical symptoms/number of challenged animals)
Compared with the control group, a less number or none of the vaccinated animals had clinical symptoms on day 28 and 33.

Clinical Symptoms of *Trichophyton rubrum* Disease in Guinea Pigs

TABLE 28

(For method see example 34)

| Complex | | Day 7 | Day 14 | Day 23 | Day 28 |
|---|---|---|---|---|---|
| VII-I (Example 40) | mean | 1.0 | 2.8 | 1.4 | 0.6 |
| VII-II (Example 41) | mean | 0.8 | 2.6 | 1.4 | 1.0 |
| VII-III (Example 42) | mean | 1.2 | 2.4 | 0.4 | 0.4 |
| VII-IV (Example 43) | mean | 0 | 3.2 | 0.8 | 0.4 |
| VII-V (Example 44) | mean | 0.8 | 2.4 | 1.0 | 0.4 |
| VII-VI (Example 45) | mean | 0.8 | 3.0 | 0.8 | 0.4 |
| VII-VII (Example 38) | mean | 0.3 | 2.3 | 0.3 | 0.3 |
| Untreated control | mean | 1.2 | 3.6 | 2.0 | 1.0 |

The severity of clinical symptoms of *Trichophyton rubrum* infection in challenged guinea pigs is shown after different observation periods. Compared with vaccinated animals unvaccinated control animals had more severe clinical symptoms on day 23 and 28 (see FIG. 13).

Number of Guinea Pigs with Clinical Symptoms of *Trichophyton rubrum* Disease

TABLE 29

(For method see example 34)

| Group | Complex/Vaccine | Day 7 | Day 14 | Day 23 | Day 28 |
|---|---|---|---|---|---|
| 1 | VII-I (Example 40) | 4/5 | 5/5 | 4/5 | 1/5 |
| 2 | VII-II (Example 41) | 3/5 | 5/5 | 4/5 | 3/5 |
| 3 | VII-III (Example 42) | 5/5 | 5/5 | 1/5 | 2/5 |

TABLE 29-continued (For method see example 34)

| Group | Complex/Vaccine | Day 7 | Day 14 | Day 23 | Day 28 |
|---|---|---|---|---|---|
| 4 | VII-IV (Example 43) | 0/5 | 5/5 | 2/5 | 2/5 |
| 5 | VII-V (Example 44) | 3/5 | 5/5 | 3/5 | 2/5 |
| 6 | VII-VI (Example 45) | 4/5 | 5/5 | 3/5 | 2/5 |
| 7 | VII-VII (Example 38) | 2/6 | 6/6 | 2/6 | 2/6 |
| 8 | Untreated control | 5/5 | 5/5 | 5/5 | 4/5 |

(Note: Number of animals with clinical symptoms/number of challenged animals)

compared with the control group, a less number or none of the vaccinated animals had clinical symptoms on day 28.

Clinical Symptoms of *Trichophyton mentagrophytes* Disease in Guinea Pigs

TABLE 30

(For method see example 34)

| Complex | | Day 7 | Day 14 | Day 23 | Day 28 |
|---|---|---|---|---|---|
| VII-I (Example 40) | mean | 3.6 | 3.4 | 1.6 | 0.6 |
| VII-II (Example 41) | mean | 4.0 | 4.0 | 1.8 | 1.25 |
| VII-III (Example 42) | mean | 4.0 | 4.6 | 2.0 | 0.8 |
| VII-IV (Example 43) | mean | 3.4 | 4.2 | 1.0 | 0.2 |
| VII-V (Example 44) | mean | 3.4 | 4.4 | 2.2 | 1.2 |
| VII-VI (Example 45) | mean | 3.0 | 3.8 | 2.0 | 1.0 |
| VII-VII (Example 38) | mean | 3.0 | 3.6 | 1.4 | 0 |
| Untreated control | mean | 3.2 | 4.4 | 2.2 | 2.0 |

The severity of clinical symptoms of *Trichophyton mentagrophytes* infection in challenged guinea pigs is shown after different observation periods. Compared with vaccinated animals unvaccinated control animals had more severe clinical symptoms in day 28 (see FIG. 14).

Number of Guinea Pigs with Clinical Symptoms of *Trichophyton mentagrophytes* Disease

TABLE 31

(For method see example 34)

| Group | Complex/Vaccine | Day 7 | Day 14 | Day 23 | Day 28 |
|---|---|---|---|---|---|
| 1 | VII-I (Example 40) | 5/5 | 5/5 | 4/5 | 2/5 |
| 2 | VII-II (Example 41) | 4/4 | 4/4 | 4/4 | 4/4 |
| 3 | VII-III (Example 42) | 5/5 | 5/5 | 5/5 | 3/5 |

TABLE 31-continued (For method see example 34)

| Group | Complex/Vaccine | Day 7 | Day 14 | Day 23 | Day 28 |
|---|---|---|---|---|---|
| 4 | VII-IV (Example 43) | 5/5 | 5/5 | 3/5 | 1/5 |
| 5 | VII-V (Example 44) | 5/5 | 5/5 | 5/5 | 3/5 |
| 6 | VII-VI (Example 45) | 5/5 | 5/5 | 5/5 | 3/5 |
| 7 | VII-VII (Example 38) | 5/5 | 5/5 | 4/5 | 0/5 |
| 8 | Untreated control | 5/5 | 5/5 | 5/5 | 5/5 |

(Note: Number of animals with clinical symptoms/number of challenged animals)

Compared with the control group, a less number or none of the vaccinated animals had clinical symptoms on day 28.

Clinical Symptoms of *Trichophyton rubrum* disease in Guinea Pigs

TABLE 32

(for method see examples 34, 37)

| Complex | | Day 7 | Day 14 | Day 20 | Day 29 |
|---|---|---|---|---|---|
| VIII-I (Example 39) | mean | 0 | 2.6 | 1.2 | 0 |
| VIII-I (Example 39) and treated by Prednisolon-21-acetat | mean | 0.6 | 2.6 | 1.8 | 0 |
| Unvaccinated control and treated by Prednisolon-21-acetat | mean | 0.4 | 4.2 | 2.8 | 1.6 |
| Untreated control | mean | 1.0 | 3.6 | 1.8 | 0.6 |

The severity of clinical symptoms of *Trichophyton rubrum* infection in challenged guinea pigs is shown after different observation periods. Compared with unvaccinated controls treated by Prednisolon-21-acetat and untreated controls the vaccinated animals had no clinical symptoms in day 28 (see FIG. 15).

Number of Guinea Pigs with Clinical Symptoms of *Trichophyton rubrum* Disease

TABLE 33

(for method see example 34, 37)

| Group | Complex/Vaccine | Day 7 | Day 14 | Day 20 | Day 29 |
|---|---|---|---|---|---|
| 1 | VIII-I (Example 39) | 0/5 | 5/5 | 3/5 | 0/5 |
| 2 | VIII-I (Example 39) and treated by Prednisolon-21-acetat | 2/5 | 5/5 | 4/5 | 0/5 |

TABLE 33-continued (for method see example 34, 37)

| Group | Complex/Vaccine | Day 7 | Day 14 | Day 20 | Day 29 |
|---|---|---|---|---|---|
| 3 | Unvaccinated control and treated by Prednisolon-21-acetat | 2/5 | 5/5 | 5/5 | 4/5 |
| 4 | Untreated control | 5/5 | 5/5 | 5/5 | 1/3 |

(Note: Number of animals with clinical symptoms/number of challenged animals)

Compared with the control group the not vaccinated animals had clinical symptoms on day 28.

Clinical Symptoms of *Trichophyton mentagrophytes* Disease in Guinea Pigs

TABLE 34

(For method see example 34, 37)

| Complex | | Day 7 | Day 14 | Day 20 | Day 29 |
|---|---|---|---|---|---|
| VIII-I (Example 39) | mean | 3.2 | 3.6 | 2.0 | 0 |
| VIII-I (Example 39) and treated by Prednisolon-21-acetat | mean | 3.0 | 3.6 | 2.4 | 0 |
| Unvaccinated control and treated by Prednisolon-21-acetat | mean | 4.0 | 4.8 | 3.4 | 0.2 |
| Untreated control | mean | 4.0 | 4.8 | 3.6 | 2.0 |

The severity of clinical symptoms of *Trichophyton mentagrophytes* infection in challenged guinea pigs is shown after different observation periods. Compared with unvaccinated controls treated by Prednisolon-21-acetat and untreated controls the vaccinated animals had no clinical symptoms on day 28 (see FIG. 16).

Number of Guinea Pigs with Clinical Symptoms of *Trichophyton mentagrophytes* Disease

TABLE 35

(For method see example 34, 37)

| Group | Complex/Vaccine | Day 7 | Day 14 | Day 20 | Day 29 |
|---|---|---|---|---|---|
| 1 | VIII-I (Example 39) | 0/5 | 5/5 | 3/5 | 0/5 |
| 2 | VIII-I (Example 39) and treated by Prednisolon-21-acetat | 2/5 | 5/5 | 4/5 | 0/5 |
| 3 | Unvaccinated control and treated by Prednisolon-21-acetat | 2/5 | 5/5 | 5/5 | 4/5 |

TABLE 35-continued (For method see example 34, 37)

| Group | Complex/Vaccine | Day 7 | Day 14 | Day 20 | Day 29 |
|---|---|---|---|---|---|
| 4 | Untreated control | 5/5 | 5/5 | 5/5 | 1/3 |

(Note: Number of animals with clinical symptoms/number of challenged animals)

Compared with the control group the not vaccinated animals had clinical symptoms on day 28.

Clinical Symptoms of *Candida albicans* Disease in Guinea Pigs

TABLE 36

(For method see example 34)

| Complex | | Day 7 | Day 14 | Day 20 | Day 29 |
|---|---|---|---|---|---|
| VIII-I (Example 39) | mean | 3.0 | 3.2 | 0.0 | 0.0 |
| Untreated control | mean | 3.2 | 3.6 | 3.0 | 2.2 |

The severity of clinical symptoms of *Candida albicans* infection in challenged guinea pigs is shown after different observation periods. Compared with vaccinated animals (ComplexVIII-I) unvaccinated control animals had more severe clinical symptoms (see FIG. 17).

Number of Guinea Pigs with Clinical Symptoms of *Candida albicans* Disease

TABLE 37

(For method see example 34)

| Group | Complex/Vaccine | Day 7 | Day 14 | Day 20 | Day 29 |
|---|---|---|---|---|---|
| 1 | VIII-I (Example 39) | 5/5 | 5/5 | 0/5 | 0/5 |
| 2 | Untreated control | 5/5 | 5/5 | 5/5 | 4/5 |

(Note: Number of animals with clinical symptoms/number of challenged animals)

Compared with the control group the vaccinated animals did not display clinical symptoms on days 20 and 28.

Clinical Symptoms of *Microsporum canis* Disease in Guinea Pigs

TABLE 38

(For method see example 34)

| Complex | | Day 7 | Day 14 | Day 20 | Day 29 |
|---|---|---|---|---|---|
| VIII-II (Example 46) | mean | 3.0 | 3.8 | 2.4 | 0.2 |
| Untreated control | mean | 3.2 | 4.2 | 2.2 | 2.0 |

The severity of clinical symptoms of *Microsporum canis* infection in challenged guinea pigs is shown after different observation periods. Compared with vaccinated animals (ComplexVIII-II) unvaccinated control animals had more severe clinical symptoms in 29 day (see FIG. 18).

Number of Guinea Pigs with Clinical Symptoms of *Microsporum canis* Disease

TABLE 39

(For method see example 34)

| | | Date of observation | | | |
|---|---|---|---|---|---|
| Group | Complex/Vaccine | Day 7 | Day 14 | Day 20 | Day 29 |
| 1 | VIII-II (Example 46) | 5/5 | 5/5 | 5/5 | 1/5 |
| 2 | Untreated control | 5/5 | 5/5 | 4/5 | 4/5 |

(Note: Number of animals with clinical symptoms/number of challenged animals)

Compared with the control group the less vaccinated animals had clinical symptoms on day 28.

Clinical Symptoms of *Trichophyton rubrum* Disease in Guinea Pigs

TABLE 40

(For method see example 34)

| | | Date of observation | | | |
|---|---|---|---|---|---|
| Complex | | Day 7 | Day 14 | Day 20 | Day 29 |
| VIII-II (Example 46) | mean | 0.6 | 2.4 | 0.8 | 0 |
| Untreated control | mean | 1.0 | 3.6 | 1.8 | 0.6 |

The severity of clinical symptoms of *Trichophyton rubrum* infection in challenged guinea pigs is shown after different observation periods. Compared with vaccinated animals (ComplexVIII-II) unvaccinated control animals had more severe clinical symptoms on days 20 and 29 (see FIG. 19)

Number of Guinea Pigs with Clinical Symptoms of *Trichophyton rubrum* Disease

TABLE 41

(For method see example 34)

| | | Date of observation | | | |
|---|---|---|---|---|---|
| Group | Complex/Vaccine | Day 7 | Day 14 | Day 20 | Day 29 |
| 1 | VIII-II (Example 46) | 3/5 | 5/5 | 2/5 | 0/5 |
| 2 | Untreated control | 4/5 | 5/5 | 5/5 | 1/3 |

(Note: Number of animals with clinical symptoms/number of challenged animals)

Compared with the control group the less vaccinated animals had clinical symptoms on days 20 and 29.

Clinical Symptoms of *Trichophyton mentagrophytes* Disease in Guinea Pigs

TABLE 42

(for method see example 34)

| | | Date of observation | | | |
|---|---|---|---|---|---|
| Complex | | Day 7 | Day 14 | Day 20 | Day 29 |
| VIII-II (Example 46) | mean | 3.0 | 3.6 | 1.8 | 0 |
| Untreated control | mean | 4.0 | 4.8 | 3.6 | 2.0 |

The severity of clinical symptoms of *Trichophyton mentagrophytes* infection in challenged guinea pigs is shown after different observation periods. Compared with vaccinated animals (ComplexVIII-II) unvaccinated control animals had more severe clinical symptoms in 20 and 29 day (see FIG. 20).

Number of Guinea Pigs with Clinical Symptoms of *Trichophyton mentagrophytes* disease

TABLE 43

(for method see example 34)

| | | Date of observation | | | |
|---|---|---|---|---|---|
| Group | Complex/Vaccine | Day 7 | Day 14 | Day 20 | Day 29 |
| 1 | VIII-II (Example 46) | 5/5 | 5/5 | 5/5 | 0/5 |
| 2 | Untreated control | 5/5 | 5/5 | 5/5 | 4/4 |

(Note: Number of animals with clinical symptoms/number of challenged animals)

Compared with the control group the less vaccinated animals had clinical symptoms on days 20 and 29.

Results of an $ID_{100}$ *Candida albicans* Challenge in Vaccinated Mice

TABLE 44

Development of the disease
(Method see example 29, 35)

| COMPLEXES | Number of animals | Number of dead animals | Number of animals with symptoms of *Candida albicans* infection | % of dead animals/% of infected animals |
|---|---|---|---|---|
| VI-I (Example 22) | 10 | 0 | 3 | 0/30 |
| VI-II (Example 23) | 10 | 4 | 9 | 40/90 |
| VI-III (Example 6) | 10 | 2 | 5 | 20/50 |
| VI-IV (Example 26) | 10 | 3 | 6 | 30/60 |
| VI-V (Example 25) | 10 | 4 | 6 | 40/60 |
| VI-VI (Example 19) | 10 | 2 | 5 | 20/50 |
| Untreated control | 10 | 5 | 9 | 50/90 |

When using ID100 70% of the animals vaccinated by Complex VI-I 50% of animals vaccinated by Complexes VI-III and VI-VI were healthy while 90% of the animals of the control group suffered from clinical symptoms of candidiasis. The animals vaccinated by Complex VI-I were alive during the 4 weeks after challenge (duration of experiment). Also 80% of the animals vaccinated by Complexes VI-II and VI-VI were alive during the duration of the experiment.

Results of an $ID_{100}$ Candida albicans Challenge in Vaccinated Mice

TABLE 45

Development of the disease
(Method see example 29, 35)

| COMPLEXES | Dose of vaccine | Number of animals | Number of dead animals | Number of animals with symptoms of Candida albicans infection | % of dead animals/% of infected animals |
|---|---|---|---|---|---|
| VII-VII (Example 38) | 0.1 | 10 | 5 | 7 | 50/70 |
| VII-VII (Example 38) | 0.2 | 10 | 5 | 6 | 50/60 |
| VII-VII (Example 38) | 0.5 | 10 | 5 | 7 | 50/70 |
| VII-VII (Example 38) | 1.0 | 10 | 8 | 8 | 80/80 |
| VII-VII (Example 38) | 2.0 | 10 | 4 | 7 | 40/70 |
| Untreated control | — | 10 | 8 | 9 | 80/90 |

When using ID100 40% of the animals vaccinated by a dose of 0.2 ml were healthy while 90% of the animals of the control group suffered from clinical symptoms of candidiasis. 50% of animals vaccinated by a dose of 0.2 ml were alive during 4 weeks after challenge (duration of experiment). Also 80% unvaccinated animals died during the experiment. This dose of vaccine was with more prophylactic efficacy than other doses of vaccine.

Safety Test of Vaccine Batch No.851

TABLE 46

(Method see example 35)

| COMPLEXES | Dose of vaccine | Number of application | Number of animals | Number of dead animals |
|---|---|---|---|---|
| VII-VII (Example 38) | 0.1 | 2 | 10 | 0 |
| VII-VII (Example 38) | 0.2 | 2 | 10 | 0 |
| VII-VII (Example 38) | 0.5 | 2 | 10 | 0 |
| VII-VII (Example 38) | 1.0 | 2 | 10 | 0 |
| VII-VII (Example 38) | 2.0 | 2 | 10 | 0 |

The two-time injection of vaccine with different doses show the safety of tested batch No.851 factory-produced.

The Adjuvant Activity of Vaccine Batch No. 851

TABLE 47

(Method see example 47)

| COMPLEXES | Number of animals | Dose of RF-2 in IU | Days after challenge* | | | | | | | |
|---|---|---|---|---|---|---|---|---|---|---|
| | | | 1 | 2 | 3 | 4 | 5 | 6 | 7 | 8 |
| RF-2 standard (Example 47) | 14 | 0.2 | — | 5 | 8 | 1 | — | — | — | — |
| RF-2 standard (Example 47) | 14 | 1.0 | — | 1 | 10 | 1 | — | — | — | — |
| RF-2 standard (Example 47) | 14 | 5.0 | — | — | — | 1 | — | — | — | — |
| RF-2 standard with Complex VII-VII (Example 47) | 14 | 0.2 | — | 4 | 5 | 3 | 1 | 1 | — | — |
| RF-2 standard with Complex VII-VII (Example 47) | 14 | 1.0 | — | — | 4 | 3 | 1 | — | — | — |
| RF-2 standard with Complex VII-VII (Example 47) | 14 | 5.0 | — | — | — | — | — | — | — | — |
| Untreated control | 10 | — | — | 6 | 4 | — | — | — | — | — |

Note: *the challenge of animals in day 0 was done.

At that time the activity of RF-2 standard vaccine was 50.0 IU/ml and the vaccine complexes of batch No.851 had 74.0 IU/ml. The time of life of the mice vaccinated with RF-2 with a dose of 0.2 ml and Complex VII-VII compared with RF-2 alone was longer. The number of animals which died after challenge was less in the group vaccinated by RF-2 with Complex VII-VII than in RF-2 vaccinated animals.

What is claimed is:

1. A vaccine comprising homogenized inactivated dermatophyte microconidia and inactivated yeast blastospores or antigenic material thereof.

2. The vaccine of claim 1 wherein the blastospores are in a swollen condition and/or have germ tubes and/or the microconidia are in a swollen condition and/or have germ tubes.

3. The vaccine of claim 2, wherein at least 50% of the blastospores are in a swollen condition and/or have germ tubes and/or at least 50% of the microconidia are in a swollen condition and/or have germ tubes.

4. The vaccine of claim 1, wherein the yeast blastospores belong to the genus Candida and the dermatophyte microconidia belong to at least one of the genera selected from the group consisting of Trichophyton, Microsporum and mixtures thereof.

5. The vaccine of claim 4, wherein the yeast blastospores belong to the species Candida albicans and the dermatophyte microconidia belong to at least one of the species selected from the group consisting of Trichophyton rubrum, Trichophyton mentagrophytes, Microsporum canis and mixtures thereof.

6. The vaccine of claim 5, wherein the yeast blastospores belong to at least one of the strains selected from the group consisting of Candida albicans DSM-9456, Candida albicans DSM-9457, Candida albicans DSM-9458, Candida albicans DSM-9459 and mixtures thereof, and the dermatophyte microconidia belong to at least one of the strains selected from the group consisting of Trichophyton rubrum DSM-9469, Trichophyton rubrum DSM-9470, Trichophyton rubrum DSM-9471, *Trichophyton rubrum* DSM-9472, *Trichophyton mentagrophytes* DSM-7279, *Microsporum canis* DSM-7281 and mixtures thereof.

7. The vaccine of claim 1, wherein the fungal spores have been inactivated with thiomersal, formaldehyde or 2-propiolactone.

8. The vaccine of claim 7, wherein the fungal spores have been modified after inactivation.

9. The vaccine of claim 8, wherein said fungal spores have been modified by treatment with $H_2O_2$ or salts of permanganate.

10. The vaccine of claim 1, wherein said vaccine comprises no additional immunomodulatory substance.

11. The vaccine of claim 1, wherein said vaccine comprises no adjuvant.

12. The vaccine of claim 1, wherein said vaccine comprises an additional substance with immunomodulatory activity.

13. The vaccine of claim 1, wherein said vaccine comprises an adjuvant and/or at least one cytokine.

14. The vaccine of claim 1, wherein said vaccine comprises 10 to 90 million spores per ml.

15. The vaccine of claim 14, wherein said vaccine comprises about 60 million spores per ml.

16. A method for the prophylaxis or treatment of mycoses in a mammal in need thereof, comprising administering the vaccine of claim 1.

17. The method of claim 16, wherein the mammal is a human.

18. The method of claim 16, wherein the mycoses are selected from the group consisting of Dermatomycosis, Onychomycosis, Candidosis and mixtures thereof.

19. A method for modulating the immune response in a mammal in need thereof, comprising administering the vaccine of claim 1.

20. A method for stimulating the immune response in a mammal in need thereof, comprising administering the vaccine of claim 1.

21. The method of claim 20, wherein the mammal is immunocompromised.

22. A method for the preparation of a vaccine comprising:
(a) growing a dermatophyte on a suitable solid medium and harvesting and homogenizing the dermatophyte microconidia or antigenic material therof;
(b) growing a yeast on a suitable medium and harvesting and homogenizing the yeast blastopores or antigenic material therof; and
(c) combining and inactivating the homogenate obtained in steps (a) and (b).

23. The method of claim 22, wherein the dermatophyte is homogenized in aqueous solution comprising (a) 0.1–0.3% fermented hydrolyzed muscle protein, 0.1–1.0% soy peptone or 0.1–1.0% pork peptone and (b) 5–6% glucose and 0.1–1.0% yeast extract, and subsequently incubated for 1–2 days at 28° C.

24. The method of claim 22, wherein the yeast is incubated after homogenization in the presence of 5–6% $CO_2$ for about 2 to 4 hours.

25. The method of claim 22, wherein the fungi homogenates are treated with $H_2O_2$ or a permanganate salt.

26. A method for the preparation of an increased amount of swollen microconidlia and microconidia with germ tubes of dermatophytes comprising:
(a) cultivating a dermatophyte on a solid medium;
(b) harvesting and homogenizing the culture in a liquid medium;
(c) maintaining the pH of the liquid medium at 6.2 to 7.2;
(d) transferring the suspension in a separate vessel containing fresh liquid medium;
(e) monitoring the growth and morphological appearance of the dermatophyte cells; and
(f) harvesting the cells when no less than 50% of the microconidia display a swollen or germinating condition, and no more than 7–10% of the cells display a second mycelial branch.

27. The method of claim 26, wherein the culture medium is malt extract-agar or agar Sabouraud, and the liquid medium comprises (a) 0.3–1.0% crude extract or peptone from meat or soya, (b) 5–6% glucose and (c) 0.1–1% yeast extract or malt-extract broth or meat-glucose broth.

28. A method for the preparation of an increased amount of swollen blastospores and blastospores with germ tubes of yeast comprising:
(a) cultivating yeast on a solid medium;
(b) harvesting and homogenizing the yeast in a liquid medium;
(c) incubating the homogenate in a $CO_2$ atmosphere of 5–6% at 36–38° C. for 2–4 hours,
(d) monitoring the growth and morphological appearance of the yeast cells; and
(e) harvesting the cells when no less than 50% of the blastospores display germ tubes or a swollen condition.

29. The method of claim 28, wherein the liquid culture medium has a pH of 6.8–7.0.

30. The method of claim 22, wherein the yeast blastospores belong to the genus Candida and the dermatophyte belong to at least one of the genera selected from the group consisting of Trichophyton, Microsporum and mixtures thereof.

31. The method of claim 30, wherein the yeast belongs to the species *Candida albicans* and the dermatophyte belong to at least one of the species selected from the group consisting of *Trichophyton rubrum, Trichophyton mentagrophytes, Microsporum canis*, and mixtures thereof.

32. The method of claim 31, wherein the yeast belong to at least one of the strains selected from the group consisting of *Candida albicans* DSM-9456, *Candida albicans* DSM-9457, *Candida albicans* DSM-9458, *Candida albicans* DSM-9459, and mixtures thereof, and the dermatophyte belong to at least one of the strains selected from the group consisting of *Trichophyton rubrum* DSM-9469, *Trichophyton rubrum* DSM-9470, *Trichophyton rubrum* DSM-9471, *Trichophyton rubrum* DSM-9472, *Trichophyton mentagrophytes* DSM-7279, *Microsporum canis* DSM-7281, and mixtures thereof.

* * * * *